(12) United States Patent
Long

(10) Patent No.: US 11,955,109 B2
(45) Date of Patent: Apr. 9, 2024

(54) DRIVING TECHNIQUES FOR PHASED-ARRAY SYSTEMS

(71) Applicant: Ultrahaptics IP Ltd, Bristol (GB)

(72) Inventor: Benjamin John Oliver Long, Bristol (GB)

(73) Assignee: Ultrahaptics IP Ltd, Bristol (GB)

( * ) Notice: Subject to any disclaimer, the term of this patent is extended or adjusted under 35 U.S.C. 154(b) by 0 days.

(21) Appl. No.: 17/195,795

(22) Filed: Mar. 9, 2021

(65) Prior Publication Data

US 2021/0225355 A1   Jul. 22, 2021

Related U.S. Application Data

(63) Continuation of application No. 15/839,184, filed on Dec. 12, 2017, now Pat. No. 10,943,578.
(Continued)

(51) Int. Cl.
*G10K 11/34* (2006.01)
*A61B 8/00* (2006.01)
(Continued)

(52) U.S. Cl.
CPC ............ *G10K 11/34* (2013.01); *A61B 8/4488* (2013.01); *B06B 1/0622* (2013.01);
(Continued)

(58) Field of Classification Search
CPC .... G10K 11/34; G10K 11/008; G10K 11/341; G10K 11/346; G10K 11/36; G10K 15/00;
(Continued)

(56) References Cited

U.S. PATENT DOCUMENTS 4,218,921 A   8/1980 Berge
4,771,205 A   9/1988 Mequio
(Continued)

FOREIGN PATENT DOCUMENTS

CA   2470115 A1   6/2003
CN   101986787   3/2011
(Continued)

OTHER PUBLICATIONS

A. B. Vallbo, Receptive field characteristics of tactile units with myelinated afferents in hairy skin of human subjects, Journal of Physiology (1995), 483.3, pp. 783-795.
(Continued)

*Primary Examiner* — Xu Mei
(74) *Attorney, Agent, or Firm* — Koffsky Schwalb LLC; Mark I. Koffsky

(57) ABSTRACT

Various techniques for driving phased array systems are described, specifically intended for acoustic phased arrays with applications to mid-air haptics, parametric audio, acoustic levitation and acoustic imaging, including a system: 1) that is capable of mitigating the effect of the changes in the air to provide a consistent haptic experience; 2) that produces trap points in air; 3) that defines phased-array optimization in terms of vectors for the production of more consistent haptic effects; 4) that defines one or more control points or regions in space via a controlled acoustic field; 5) that uses a reduced representation method for the construction of acoustic basis functions; 6) that performs efficient evaluation of complex-valued functions for a large quantity of throughput; 7) that generates a Krylov sub-space of a matrix; and 8) that maximizes an objective described by different control points and/or regions to those used to create the acoustic basis functions.

16 Claims, 22 Drawing Sheets

Related U.S. Application Data

(60) Provisional application No. 62/594,836, filed on Dec. 5, 2017, provisional application No. 62/594,687, filed on Dec. 5, 2017, provisional application No. 62/594,874, filed on Dec. 5, 2017, provisional application No. 62/594,574, filed on Dec. 5, 2017, provisional application No. 62/438,512, filed on Dec. 23, 2016, provisional application No. 62/437,791, filed on Dec. 22, 2016, provisional application No. 62/436,457, filed on Dec. 20, 2016, provisional application No. 62/433,544, filed on Dec. 13, 2016.

(51) Int. Cl.
| | |
|---|---|
| *B06B 1/06* | (2006.01) |
| *G10K 11/00* | (2006.01) |
| *G10K 11/36* | (2006.01) |
| *G10K 15/00* | (2006.01) |

(52) U.S. Cl.
CPC .......... *G10K 11/008* (2013.01); *G10K 11/341* (2013.01); *G10K 11/346* (2013.01); *G10K 11/36* (2013.01); *G10K 15/00* (2013.01)

(58) Field of Classification Search
CPC .... A61B 8/4488; B06B 1/0622; H04R 27/00; H04R 2227/005
USPC ....................................................... 381/77, 79
See application file for complete search history.

(56) References Cited

U.S. PATENT DOCUMENTS

| | | |
|---|---|---|
| 4,881,212 A | 11/1989 | Takeuchi |
| 5,226,000 A | 7/1993 | Moses |
| 5,235,986 A | 8/1993 | Maslak |
| 5,243,344 A | 9/1993 | Koulopoulos |
| 5,329,682 A | 7/1994 | Thurn |
| 5,371,834 A | 12/1994 | Tawel |
| 5,422,431 A | 6/1995 | Ichiki |
| 5,426,388 A | 6/1995 | Flora |
| 5,477,736 A | 12/1995 | Lorraine |
| 5,511,296 A | 4/1996 | Dias |
| 5,729,694 A | 3/1998 | Holzrichter |
| 5,859,915 A | 1/1999 | Norris |
| 6,029,518 A | 2/2000 | Oeftering |
| 6,193,936 B1 | 2/2001 | Gardner |
| 6,216,538 B1 | 4/2001 | Yasuda |
| 6,436,051 B1 | 8/2002 | Morris |
| 6,503,204 B1 | 1/2003 | Sumanaweera |
| 6,647,359 B1 | 11/2003 | Verplank |
| 6,771,294 B1 | 8/2004 | Pulli |
| 6,772,490 B2 | 8/2004 | Toda |
| 6,800,987 B2 | 10/2004 | Toda |
| 7,107,159 B2 | 9/2006 | German |
| 7,109,789 B2 | 9/2006 | Spencer |
| 7,182,726 B2 | 2/2007 | Williams |
| 7,225,404 B1 | 5/2007 | Zilles |
| 7,284,027 B2 | 10/2007 | Jennings, III |
| 7,345,600 B1 | 3/2008 | Fedigan |
| 7,487,662 B2 | 2/2009 | Schabron |
| 7,497,662 B2 | 3/2009 | Mollmann |
| 7,577,260 B1 | 8/2009 | Hooley |
| 7,692,661 B2 | 4/2010 | Cook |
| RE42,192 E | 3/2011 | Schabron |
| 7,966,134 B2 | 6/2011 | German |
| 8,000,481 B2 | 8/2011 | Nishikawa |
| 8,123,502 B2 | 2/2012 | Blakey |
| 8,269,168 B1 | 9/2012 | Axelrod |
| 8,279,193 B1 | 10/2012 | Birnbaum |
| 8,351,646 B2 | 1/2013 | Fujimura |
| 8,369,973 B2 | 2/2013 | Risbo |
| 8,594,350 B2 | 11/2013 | Hooley |
| 8,607,922 B1 | 12/2013 | Werner |
| 8,782,109 B2 | 7/2014 | Tsutsui |
| 8,833,510 B2 | 9/2014 | Koh |
| 8,884,927 B1 | 11/2014 | Cheatham, III |
| 9,208,664 B1 | 12/2015 | Peters |
| 9,267,735 B2 | 2/2016 | Funayama |
| 9,421,291 B2 | 8/2016 | Robert |
| 9,612,658 B2 | 4/2017 | Subramanian |
| 9,662,680 B2 | 5/2017 | Yamamoto |
| 9,667,173 B1 | 5/2017 | Kappus |
| 9,816,757 B1 | 11/2017 | Zielinski |
| 9,841,819 B2 | 12/2017 | Carter |
| 9,863,699 B2 | 1/2018 | Corbin, III |
| 9,898,089 B2 | 2/2018 | Subramanian |
| 9,945,818 B2 | 4/2018 | Ganti |
| 9,958,943 B2 | 5/2018 | Long |
| 9,977,120 B2 | 5/2018 | Carter |
| 10,101,811 B2 | 10/2018 | Carter |
| 10,101,814 B2 | 10/2018 | Carter |
| 10,133,353 B2 | 11/2018 | Eid |
| 10,140,776 B2 | 11/2018 | Schwarz |
| 10,146,353 B1 | 12/2018 | Smith |
| 10,168,782 B1 | 1/2019 | Tchon |
| 10,268,275 B2 | 4/2019 | Carter |
| 10,281,567 B2 | 5/2019 | Carter |
| 10,318,008 B2 | 6/2019 | Sinha |
| 10,444,842 B2 | 10/2019 | Long |
| 10,469,973 B2 | 11/2019 | Hayashi |
| 10,496,175 B2 | 12/2019 | Long |
| 10,497,358 B2 | 12/2019 | Tester |
| 10,510,357 B2 | 12/2019 | Kovesi |
| 10,520,252 B2 | 12/2019 | Momen |
| 10,523,159 B2 | 12/2019 | Megretski |
| 10,531,212 B2 | 1/2020 | Long |
| 10,535,174 B1 | 1/2020 | Rigiroli |
| 10,569,300 B2 | 2/2020 | Hoshi |
| 10,593,101 B1 | 3/2020 | Han |
| 10,657,704 B1 | 5/2020 | Han |
| 10,685,538 B2 | 6/2020 | Carter |
| 10,755,538 B2 | 8/2020 | Carter |
| 10,818,162 B2 * | 10/2020 | Carter .................. G10K 11/32 |
| 10,911,861 B2 | 2/2021 | Buckland |
| 10,915,177 B2 | 2/2021 | Carter |
| 10,921,890 B2 | 2/2021 | Subramanian |
| 10,930,123 B2 | 2/2021 | Carter |
| 10,943,578 B2 | 3/2021 | Long |
| 11,048,329 B1 | 6/2021 | Lee |
| 11,098,951 B2 | 8/2021 | Kappus |
| 11,113,860 B2 | 9/2021 | Rigiroli |
| 11,169,610 B2 | 11/2021 | Sarafianou |
| 11,189,140 B2 | 11/2021 | Long |
| 11,204,644 B2 * | 12/2021 | Long ....................... G08B 6/00 |
| 11,276,281 B2 | 3/2022 | Carter |
| 11,531,395 B2 | 12/2022 | Kappus |
| 11,543,507 B2 | 1/2023 | Carter |
| 11,550,395 B2 | 1/2023 | Beattie |
| 11,550,432 B2 | 1/2023 | Carter |
| 11,553,295 B2 | 1/2023 | Kappus |
| 2001/0007591 A1 | 7/2001 | Pompei |
| 2001/0033124 A1 | 10/2001 | Norris |
| 2002/0149570 A1 | 10/2002 | Knowles |
| 2003/0024317 A1 | 2/2003 | Miller |
| 2003/0144032 A1 | 7/2003 | Brunner |
| 2003/0182647 A1 | 9/2003 | Radeskog |
| 2004/0005715 A1 | 1/2004 | Schabron |
| 2004/0014434 A1 | 1/2004 | Haardt |
| 2004/0052387 A1 | 3/2004 | Norris |
| 2004/0091119 A1 | 5/2004 | Duraiswami |
| 2004/0210158 A1 | 10/2004 | Organ |
| 2004/0226378 A1 | 11/2004 | Oda |
| 2004/0264707 A1 | 12/2004 | Yang |
| 2005/0052714 A1 | 3/2005 | Klug |
| 2005/0056851 A1 | 3/2005 | Althaus |
| 2005/0212760 A1 | 9/2005 | Marvit |
| 2005/0226437 A1 | 10/2005 | Pellegrini |
| 2005/0267695 A1 | 12/2005 | German |
| 2005/0273483 A1 | 12/2005 | Dent |
| 2006/0085049 A1 | 4/2006 | Cory |
| 2006/0090955 A1 | 5/2006 | Cardas |
| 2006/0091301 A1 | 5/2006 | Trisnadi |
| 2006/0164428 A1 | 7/2006 | Cook |

(56) References Cited

U.S. PATENT DOCUMENTS

| | | |
|---|---|---|
| 2007/0036492 A1 | 2/2007 | Lee |
| 2007/0094317 A1 | 4/2007 | Wang |
| 2007/0177681 A1 | 8/2007 | Choi |
| 2007/0214462 A1 | 9/2007 | Boillot |
| 2007/0263741 A1 | 11/2007 | Erving |
| 2008/0012647 A1 | 1/2008 | Risbo |
| 2008/0027686 A1 | 1/2008 | Mollmann |
| 2008/0084789 A1 | 4/2008 | Altman |
| 2008/0130906 A1 | 6/2008 | Goldstein |
| 2008/0152191 A1 | 6/2008 | Fujimura |
| 2008/0226088 A1 | 9/2008 | Aarts |
| 2008/0273723 A1 | 11/2008 | Hartung |
| 2008/0300055 A1 | 12/2008 | Lutnick |
| 2009/0093724 A1 | 4/2009 | Pernot |
| 2009/0116660 A1 | 5/2009 | Croft, III |
| 2009/0232684 A1 | 9/2009 | Hirata |
| 2009/0251421 A1 | 10/2009 | Bloebaum |
| 2009/0319065 A1 | 12/2009 | Risbo |
| 2010/0013613 A1 | 1/2010 | Weston |
| 2010/0016727 A1 | 1/2010 | Rosenberg |
| 2010/0030076 A1 | 2/2010 | Vortman |
| 2010/0044120 A1 | 2/2010 | Richter |
| 2010/0066512 A1 | 3/2010 | Rank |
| 2010/0085168 A1 | 4/2010 | Kyung |
| 2010/0103246 A1 | 4/2010 | Schwerdtner |
| 2010/0109481 A1 | 5/2010 | Buccafusca |
| 2010/0199232 A1 | 8/2010 | Mistry |
| 2010/0231508 A1 | 9/2010 | Cruz-Hernandez |
| 2010/0262008 A1 | 10/2010 | Roundhill |
| 2010/0302015 A1 | 12/2010 | Kipman |
| 2010/0321216 A1 | 12/2010 | Jonsson |
| 2011/0006888 A1 | 1/2011 | Bae |
| 2011/0010958 A1 | 1/2011 | Clark |
| 2011/0051554 A1 | 3/2011 | Varray |
| 2011/0066032 A1 | 3/2011 | Vitek |
| 2011/0199342 A1 | 8/2011 | Vartanian |
| 2011/0310028 A1 | 12/2011 | Camp, Jr. |
| 2012/0057733 A1 | 3/2012 | Morii |
| 2012/0063628 A1 | 3/2012 | Rizzello |
| 2012/0066280 A1 | 3/2012 | Tsutsui |
| 2012/0223880 A1 | 9/2012 | Birnbaum |
| 2012/0229400 A1 | 9/2012 | Birnbaum |
| 2012/0229401 A1 | 9/2012 | Birnbaum |
| 2012/0236689 A1 | 9/2012 | Brown |
| 2012/0243374 A1 | 9/2012 | Dahl |
| 2012/0249409 A1 | 10/2012 | Toney |
| 2012/0249474 A1 | 10/2012 | Pratt |
| 2012/0299853 A1 | 11/2012 | Dagar |
| 2012/0307649 A1 | 12/2012 | Park |
| 2012/0315605 A1 | 12/2012 | Cho |
| 2013/0035582 A1 | 2/2013 | Radulescu |
| 2013/0079621 A1 | 3/2013 | Shoham |
| 2013/0094678 A1 | 4/2013 | Scholte |
| 2013/0100008 A1 | 4/2013 | Marti |
| 2013/0101141 A1 | 4/2013 | Mcelveen |
| 2013/0173658 A1 | 7/2013 | Adelman |
| 2013/0331705 A1 | 12/2013 | Fraser |
| 2014/0027201 A1 | 1/2014 | Islam |
| 2014/0104274 A1 | 4/2014 | Hilliges |
| 2014/0139071 A1 | 5/2014 | Yamamoto |
| 2014/0168091 A1 | 6/2014 | Jones |
| 2014/0201666 A1 | 7/2014 | Bedikian |
| 2014/0204002 A1 | 7/2014 | Bennet |
| 2014/0265572 A1 | 9/2014 | Siedenburg |
| 2014/0269207 A1 | 9/2014 | Baym |
| 2014/0269208 A1 | 9/2014 | Baym |
| 2014/0269214 A1 | 9/2014 | Baym |
| 2014/0270305 A1 | 9/2014 | Baym |
| 2014/0369514 A1 | 12/2014 | Baym |
| 2015/0002477 A1 | 1/2015 | Cheatham, III |
| 2015/0005039 A1 | 1/2015 | Liu |
| 2015/0006645 A1 | 1/2015 | Oh |
| 2015/0007025 A1 | 1/2015 | Sassi |
| 2015/0013023 A1 | 1/2015 | Wang |
| 2015/0029155 A1 | 1/2015 | Lee |
| 2015/0066445 A1 | 3/2015 | Lin |
| 2015/0070147 A1* | 3/2015 | Cruz-Hernandez ..... G06F 3/165 340/407.1 |
| 2015/0070245 A1 | 3/2015 | Han |
| 2015/0078136 A1 | 3/2015 | Sun |
| 2015/0081110 A1 | 3/2015 | Houston |
| 2015/0084929 A1 | 3/2015 | Lee |
| 2015/0110310 A1 | 4/2015 | Minnaar |
| 2015/0130323 A1 | 5/2015 | Harris |
| 2015/0168205 A1 | 6/2015 | Lee |
| 2015/0192995 A1 | 7/2015 | Subramanian |
| 2015/0220199 A1 | 8/2015 | Wang |
| 2015/0226537 A1 | 8/2015 | Schorre |
| 2015/0226831 A1 | 8/2015 | Nakamura |
| 2015/0248787 A1 | 9/2015 | Abovitz |
| 2015/0258431 A1 | 9/2015 | Stafford |
| 2015/0277610 A1 | 10/2015 | Kim |
| 2015/0293592 A1 | 10/2015 | Cheong |
| 2015/0304789 A1 | 10/2015 | Babayoff |
| 2015/0323667 A1 | 11/2015 | Przybyla |
| 2015/0331576 A1 | 11/2015 | Piya |
| 2015/0332075 A1 | 11/2015 | Burch |
| 2016/0019762 A1 | 1/2016 | Levesque |
| 2016/0019879 A1 | 1/2016 | Daley |
| 2016/0026253 A1 | 1/2016 | Bradski |
| 2016/0044417 A1 | 2/2016 | Clemen, Jr. |
| 2016/0124080 A1 | 5/2016 | Carter |
| 2016/0138986 A1 | 5/2016 | Carlin |
| 2016/0175701 A1 | 6/2016 | Froy |
| 2016/0175709 A1 | 6/2016 | Idris |
| 2016/0189702 A1 | 6/2016 | Blanc |
| 2016/0242724 A1 | 8/2016 | Lavallee |
| 2016/0246374 A1 | 8/2016 | Carter |
| 2016/0249150 A1 | 8/2016 | Carter |
| 2016/0291716 A1 | 10/2016 | Boser |
| 2016/0306423 A1 | 10/2016 | Uttermann |
| 2016/0320843 A1 | 11/2016 | Long |
| 2016/0339132 A1 | 11/2016 | Cosman |
| 2016/0374562 A1 | 12/2016 | Vertikov |
| 2017/0002839 A1 | 1/2017 | Bukland |
| 2017/0004819 A1 | 1/2017 | Ochiai |
| 2017/0018171 A1 | 1/2017 | Carter |
| 2017/0024921 A1 | 1/2017 | Beeler |
| 2017/0052148 A1 | 2/2017 | Estevez |
| 2017/0123487 A1 | 5/2017 | Hazra |
| 2017/0123499 A1 | 5/2017 | Eid |
| 2017/0140552 A1 | 5/2017 | Woo |
| 2017/0144190 A1 | 5/2017 | Hoshi |
| 2017/0153707 A1 | 6/2017 | Subramanian |
| 2017/0168586 A1 | 6/2017 | Sinha |
| 2017/0181725 A1 | 6/2017 | Han |
| 2017/0193768 A1 | 7/2017 | Long |
| 2017/0193823 A1 | 7/2017 | Jiang |
| 2017/0211022 A1 | 7/2017 | Reinke |
| 2017/0236506 A1 | 8/2017 | Przybyla |
| 2017/0270356 A1 | 9/2017 | Sills |
| 2017/0279951 A1 | 9/2017 | Hwang |
| 2017/0336860 A1 | 11/2017 | Smoot |
| 2017/0366908 A1 | 12/2017 | Long |
| 2018/0035891 A1 | 2/2018 | Van Soest |
| 2018/0039333 A1 | 2/2018 | Carter |
| 2018/0047259 A1 | 2/2018 | Carter |
| 2018/0074580 A1 | 3/2018 | Hardee |
| 2018/0081439 A1 | 3/2018 | Daniels |
| 2018/0101234 A1 | 4/2018 | Carter |
| 2018/0139557 A1 | 5/2018 | Ochiai |
| 2018/0146306 A1 | 5/2018 | Benattar |
| 2018/0151035 A1 | 5/2018 | Maalouf |
| 2018/0166063 A1 | 6/2018 | Long |
| 2018/0181203 A1 | 6/2018 | Subramanian |
| 2018/0182372 A1 | 6/2018 | Tester |
| 2018/0190007 A1 | 7/2018 | Panteleev |
| 2018/0246576 A1 | 8/2018 | Long |
| 2018/0253627 A1 | 9/2018 | Baradel |
| 2018/0267156 A1 | 9/2018 | Carter |
| 2018/0304310 A1 | 10/2018 | Long |
| 2018/0309515 A1* | 10/2018 | Murakowski .......... H04B 10/69 |
| 2018/0310111 A1 | 10/2018 | Kappus |
| 2018/0350339 A1 | 12/2018 | Macours |

(56) References Cited

U.S. PATENT DOCUMENTS

| | | |
|---|---|---|
| 2018/0361174 A1 | 12/2018 | Radulescu |
| 2019/0038496 A1 | 2/2019 | Levesque |
| 2019/0091565 A1 | 3/2019 | Nelson |
| 2019/0163275 A1 | 5/2019 | Iodice |
| 2019/0175077 A1 | 6/2019 | Zhang |
| 2019/0187244 A1 | 6/2019 | Riccardi |
| 2019/0196578 A1 | 6/2019 | Iodice |
| 2019/0196591 A1 | 6/2019 | Long |
| 2019/0197840 A1 | 6/2019 | Kappus |
| 2019/0197841 A1 | 6/2019 | Carter |
| 2019/0197842 A1 | 6/2019 | Long |
| 2019/0204925 A1 | 7/2019 | Long |
| 2019/0206202 A1 | 7/2019 | Carter |
| 2019/0235628 A1 | 8/2019 | Lacroix |
| 2019/0257932 A1 | 8/2019 | Carter |
| 2019/0310710 A1 | 10/2019 | Deeley |
| 2019/0342654 A1 | 11/2019 | Buckland |
| 2020/0042091 A1 | 2/2020 | Long |
| 2020/0080776 A1 | 3/2020 | Kappus |
| 2020/0082804 A1 | 3/2020 | Kappus |
| 2020/0103974 A1 | 4/2020 | Carter |
| 2020/0117229 A1 | 4/2020 | Long |
| 2020/0193269 A1 | 6/2020 | Park |
| 2020/0218354 A1 | 7/2020 | Beattie |
| 2020/0294299 A1 | 9/2020 | Rigiroli |
| 2020/0302760 A1 | 9/2020 | Carter |
| 2020/0320347 A1 | 10/2020 | Nikolenko |
| 2020/0327418 A1 | 10/2020 | Lyons |
| 2020/0380832 A1 | 12/2020 | Carter |
| 2021/0037332 A1 | 2/2021 | Kappus |
| 2021/0043070 A1 | 2/2021 | Carter |
| 2021/0109712 A1 | 4/2021 | Long |
| 2021/0111731 A1 | 4/2021 | Long |
| 2021/0112353 A1 | 4/2021 | Kappus |
| 2021/0141458 A1 | 5/2021 | Sarafianou |
| 2021/0165491 A1 | 6/2021 | Sun |
| 2021/0170447 A1 | 6/2021 | Buckland |
| 2021/0183215 A1 | 6/2021 | Carter |
| 2021/0201884 A1 | 7/2021 | Kappus |
| 2021/0303072 A1 | 9/2021 | Carter |
| 2021/0303758 A1 | 9/2021 | Long |
| 2021/0334706 A1 | 10/2021 | Yamaguchi |
| 2021/0381765 A1 | 12/2021 | Kappus |
| 2021/0397261 A1 | 12/2021 | Kappus |
| 2022/0035479 A1 | 2/2022 | Lasater |
| 2022/0083142 A1 | 3/2022 | Brown |
| 2022/0095068 A1 | 3/2022 | Kappus |
| 2022/0113806 A1 | 4/2022 | Long |
| 2022/0155949 A1 | 5/2022 | Ring |
| 2022/0198892 A1 | 6/2022 | Carter |
| 2022/0236806 A1 | 7/2022 | Carter |
| 2022/0252550 A1 | 8/2022 | Catsis |
| 2022/0300028 A1 | 9/2022 | Long |
| 2022/0300070 A1 | 9/2022 | Iodice |
| 2022/0329250 A1 | 10/2022 | Long |
| 2022/0393095 A1 | 12/2022 | Chilles |

FOREIGN PATENT DOCUMENTS

| | | |
|---|---|---|
| CN | 102459900 | 5/2012 |
| CN | 102591512 | 7/2012 |
| CN | 103797379 | 5/2014 |
| CN | 103984414 A | 8/2014 |
| CN | 107340871 A | 11/2017 |
| EP | 0057594 A2 | 8/1982 |
| EP | 309003 | 3/1989 |
| EP | 0696670 A1 | 2/1996 |
| EP | 1875081 A1 | 1/2008 |
| EP | 1911530 | 4/2008 |
| EP | 2271129 A1 | 1/2011 |
| EP | 1461598 B1 | 4/2014 |
| EP | 3207817 A1 | 8/2017 |
| EP | 3216231 B1 | 8/2019 |
| GB | 2464117 | 4/2010 |
| GB | 2513884 | 11/2014 |
| GB | 2513884 A | 11/2014 |
| GB | 2530036 | 3/2016 |
| JP | 2008074075 | 4/2008 |
| JP | 2010109579 | 5/2010 |
| JP | 2011172074 | 9/2011 |
| JP | 2012048378 | 3/2012 |
| JP | 2012048378 A | 3/2012 |
| JP | 5477736 B2 | 4/2014 |
| JP | 2015035657 A | 2/2015 |
| JP | 2016035646 | 3/2016 |
| KR | 20120065779 | 6/2012 |
| KR | 20130055972 | 5/2013 |
| KR | 20160008280 | 1/2016 |
| KR | 20200082449 A | 7/2020 |
| WO | 9118486 | 11/1991 |
| WO | 9639754 | 12/1996 |
| WO | 03050511 A | 6/2003 |
| WO | 2005017965 | 2/2005 |
| WO | 2007144801 A2 | 12/2007 |
| WO | 2009071746 A1 | 6/2009 |
| WO | 2009112866 | 9/2009 |
| WO | 2010003836 | 1/2010 |
| WO | 2010139916 | 12/2010 |
| WO | 2011132012 A1 | 10/2011 |
| WO | 2012023864 | 2/2012 |
| WO | 2012104648 A1 | 8/2012 |
| WO | 2013179179 | 12/2013 |
| WO | 2014181084 | 11/2014 |
| WO | 2014181084 A1 | 11/2014 |
| WO | 2015006467 | 1/2015 |
| WO | 2015039622 | 3/2015 |
| WO | 2015127335 | 8/2015 |
| WO | 2016007920 | 1/2016 |
| WO | 2016073936 | 5/2016 |
| WO | 2016095033 A1 | 6/2016 |
| WO | 2016099279 | 6/2016 |
| WO | 2016132141 | 8/2016 |
| WO | 2016132144 | 8/2016 |
| WO | 2016137675 | 9/2016 |
| WO | 2016162058 | 10/2016 |
| WO | 2017172006 | 10/2017 |
| WO | 2020049321 A2 | 3/2020 |
| WO | 2021130505 A1 | 7/2021 |

OTHER PUBLICATIONS

Amanda Zimmerman, The gentle touch receptors of mammalian skin, Science, Nov. 21, 2014, vol. 346 Issue 6212, p. 950.

Corrected Notice of Allowability dated Aug. 9, 2021 for U.S. Appl. No. 15/396,851 (pp. 1-6).

Henrik Bruus, Acoustofluidics 2: Perturbation theory and ultrasound resonance modes, Lab Chip, 2012, 12, 20-28.

Hyunjae Gil, Whiskers: Exploring the Use of Ultrasonic Haptic Cues on the Face, CHI 2018, Apr. 21-26, 2018, Montréal, QC, Canada.

India Morrison, The skin as a social organ, Exp Brain Res (2010) 204:305-314.

JonasChatel-Goldman, Touch increases autonomic coupling between romantic partners, Frontiers in Behavioral Neuroscience Mar. 2014, vol. 8, Article 95.

Kai Tsumoto, Presentation of Tactile Pleasantness Using Airborne Ultrasound, 2021 IEEE World Haptics Conference (WHC) Jul. 6-9, 2021. Montreal, Canada.

Keisuke Hasegawa, Electronically steerable ultrasound-driven long narrow airstream, Applied Physics Letters 111, 064104 (2017).

Keisuke Hasegawa, Midair Ultrasound Fragrance Rendering, IEEE Transactions on Visualization and Computer Graphics, vol. 24, No. 4, Apr. 2018 1477.

Keisuke Hasegawa,,Curved acceleration path of ultrasound-driven airflow, J. Appl. Phys. 125, 054902 (2019).

Line S. Loken, Coding of pleasant touch by unmyelinated afferents in humans, Nature Neuroscience vol. 12 [ No. 5 [ May 2009 547.

Mariana von Mohr, The soothing function of touch: affective touch reduces feelings of social exclusion, Scientific Reports, 7: 13516, Oct. 18, 2017.

(56) References Cited

OTHER PUBLICATIONS

Mitsuru Nakajima, Remotely Displaying Cooling Sensation via Ultrasound-Driven Air Flow, Haptics Symposium 2018, San Francisco, USA p. 340.
Mohamed Yacine Tsalamlal, Affective Communication through Air Jet Stimulation: Evidence from Event-Related Potentials, International Journal of Human-Computer Interaction 2018.
Notice of Allowance dated Jul. 22, 2021 for U.S. Appl. No. 16/600,500 (pp. 1-9).
Office Action dated Aug. 10, 2021 for U.S. Appl. No. 16/564,016 (pp. 1-14).
Office Action dated Aug. 19, 2021 for U.S. Appl. No. 17/170,841 (pp. 1-9).
Office Action dated Aug. 9, 2021 for U.S. Appl. No. 17/068,825 (pp. 1-9).
Office Action dated Sep. 16, 2021 for U.S. Appl. No. 16/600,496 (pp. 1-8).
Office Action dated Sep. 24, 2021 for U.S. Appl. No. 17/080,840 (pp. 1-9).
Rochelle Ackerley, Human C-Tactile Afferents Are Tuned to the Temperature of a Skin-Stroking Caress, J. Neurosci., Feb. 19, 2014, 34(8):2879-2883.
Ryoko Takahashi, Tactile Stimulation by Repetitive Lateral Movement of Midair Ultrasound Focus, Journal of Latex Class Files, vol. 14, No. 8, Aug. 2015.
Stanley J. Bolanowski, Hairy Skin: Psychophysical Channels and Their Physiological Substrates, Somatosensory and Motor Research, vol. 11. No. 3, 1994, pp. 279-290.
Stefan G. Lechner, Hairy Sensation, Physiology 28: 142-150, 2013.
Supplemental Notice of Allowability dated Jul. 28, 2021 for U.S. Appl. No. 16/563,608 (pp. 1-2).
Supplemental Notice of Allowability dated Jul. 28, 2021 for U.S. Appl. No. 17/092,333 (pp. 1-2).
Takaaki Kamigaki, Noncontact Thermal and Vibrotactile Display Using Focused Airborne Ultrasound, EuroHaptics 2020, LNCS 12272, pp. 271-278, 2020.
Tomoo Kamakura, Acoustic streaming induced in focused Gaussian beams, J. Acoust. Soc. Am. 97 (5), Pt. 1, May 1995 p. 2740.
Uta Sailer, How Sensory and Affective Attributes Describe Touch Targeting C-Tactile Fibers, Experimental Psychology (2020), 67(4), 224-236.
Brian Kappus and Ben Long, Spatiotemporal Modulation for Mid-Air Haptic Feedback from an Ultrasonic Phased Array, ICSV25, Hiroshima, Jul. 8-12, 2018, 6 pages.
Hoshi et al.,Tactile Presentation by Airborne Ultrasonic Oscillator Array, Proceedings of Robotics and Mechatronics Lecture 2009, Japan Society of Mechanical Engineers; May 24, 2009 (5 pages).
ISR & WO for PCT/GB2020/052545 (Jan. 27, 2021) 14 pages.
ISR and WO for PCT/GB2020/052544 (Dec. 18, 2020) (14 pages).
ISR for PCT/GB2020/052546 (Feb. 23, 2021) (14 pages).
ISR for PCT/GB2020/053373 (Mar. 26, 2021) (16 pages).
Notice of Allowance dated Apr. 20, 2021 for U.S. Appl. No. 16/563,608 (pp. 1-5).
Notice of Allowance dated Jun. 10, 2021 for U.S. Appl. No. 17/092,333 (pp. 1-9).
Notice of Allowance dated Jun. 25, 2021 for U.S. Appl. No. 15/396,851 (pp. 1-10).
Office Action dated Jun. 25, 2021 for U.S. Appl. No. 16/899,720 (pp. 1-5).
Office Action dated Mar. 31, 2021 for U.S. Appl. No. 16/228,760 (pp. 1-21).
Office Action dated May 13, 2021 for U.S. Appl. No. 16/600,500 (pp. 1-9).
Office Action dated May 14, 2021 for U.S. Appl. No. 16/198,959 (pp. 1-6).
"Welcome to Project Soli" video, https://atap.google.com/#project-soli Accessed Nov. 30, 2018, 2 pages.
A. Sand, Head-Mounted Display with Mid-Air Tactile Feedback, Proceedings of the 21st ACM Symposium on Virtual Reality Software and Technology, Nov. 13-15, 2015 (8 pages).
Alexander, J. et al. (2011), Adding Haptic Feedback to Mobile TV (6 pages).
Aoki et al., Sound location of stero reproduction with parametric loudspeakers, Applied Acoustics 73 (2012) 1289-1295 (7 pages).
Ashish Shrivastava et al.. Learning from Simulated and Unsupervised Images through Adversarial Training, Jul. 19, 2017, pp. 1-16.
Bajard et al., BKM: A New Hardware Algorithm for Complex Elementary Functions, 8092 IEEE Transactions on Computers 43 (1994) (9 pages).
Bajard et al., Evaluation of Complex Elementary Functions / A New Version of BKM, SPIE Conference on Advanced Signal Processing, Jul. 1999 (8 pages).
Benjamin Long et al, "Rendering volumetric haptic shapes in mid-air using ultrasound", ACM Transactions on Graphics (TOG), ACM, US, (Nov. 19, 2014), vol. 33, No. 6, ISSN 0730-0301, pp. 1-10.
Bortoff et al., Pseudolinearization of the Acrobot using Spline Functions, IEEE Proceedings of the 31st Conference on Decision and Control, Sep. 10, 1992 (6 pages).
Bozena Smagowska & Małgorzata Pawlaczyk-Łuszczyńska (2013) Effects of Ultrasonic Noise on the Human Body—A Bibliographic Review, International Journal of Occupational Safety and Ergonomics, 19:2, 195-202.
Canada Application 2,909,804 Office Action dated Oct. 18, 2019, 4 pages.
Casper et al., Realtime Control of Multiple-focus Phased Array Heating Patterns Based on Noninvasive Ultrasound Thermography, IEEE Trans Biomed Eng. Jan. 2012; 59(1): 95-105.
Christoper M. Bishop, Pattern Recognition and Machine Learning, 2006, pp. 1-758.
Colgan, A., "How Does the Leap Motion Controller Work?" Leap Motion, Aug. 9, 2014, 10 pages.
Corrected Notice of Allowability dated Jan. 14, 2021 for U.S. Appl. No. 15/897,804 (pp. 1-2).
Corrected Notice of Allowability dated Jun. 21, 2019 for U.S. Appl. No. 15/966,213 (2 pages).
Corrected Notice of Allowability dated Oct. 31, 2019 for U.S. Appl. No. 15/623,516 (pp. 1-2).
Damn Geeky, "Virtual projection keyboard technology with haptic feedback on palm of your hand," May 30, 2013, 4 pages.
David Joseph Tan et al., Fits like a Glove: Rapid and Reliable Hand Shape Personalization, 2016 IEEE Conference on Computer Vision and Pattern Recognition, pp. 5610-5619.
Definition of "Interferometry"according to Wikipedia, 25 pages., Retrieved Nov. 2018.
Definition of "Multilateration" according to Wikipedia, 7 pages., Retrieved Nov. 2018.
Definition of "Trilateration"according to Wikipedia, 2 pages., Retrieved Nov. 2018.
Diederik P. Kingma et al., Adam: A Method for Stochastic Optimization, Jan. 30, 2017, pp. 1-15.
E. Bok, Metasurface for Water-to-Air Sound Transmission, Physical Review Letters 120, 044302 (2018) (6 pages).
E.S. Ebbini et al. (1991), Aspherical-section ultrasound phased array applicator for deep localized hyperthermia, Biomedical Engineering, IEEE Transactions on (vol. 38 Issue: 7), pp. 634-643.
EPO Office Action for EP16708440.9 dated Sep. 12, 2018 (7 pages).
EPSRC Grant summary EP/J004448/1 (2011) (1 page).
Eric Tzeng et al., Adversarial Discriminative Domain Adaptation, Feb. 17, 2017, pp. 1-10.
European Office Action for Application No. EP16750992.6, dated Oct. 2, 2019, 3 pages.
Ex Parte Quayle Action dated Dec. 28, 2018 for U.S. Appl. No. 15/966,213 (pp. 1-7).
Extended European Search Report for Application No. EP19169929.7, dated Aug. 6, 2019, 7 pages.
Freeman et al., Tactile Feedback for Above-Device Gesture Interfaces: Adding Touch to Touchless Interactions ICMI'14, Nov. 12-16, 2014, Istanbul, Turkey (8 pages).
Gavrilov L R et al (2000) "A theoretical assessment of the relative performance of spherical phased arrays for ultrasound surgery" Ultrasonics, Ferroelectrics, and Frequency Control, IEEE Transactions on (vol. 47, Issue: 1), pp. 125-139.

(56) References Cited

OTHER PUBLICATIONS

Gavrilov, L.R. (2008) "The Possibility of Generating Focal Regions of Complex Configurations in Application to the Problems of Stimulation of Human Receptor Structures by Focused Ultrasound" Acoustical Physics, vol. 54, No. 2, pp. 269-278.
Georgiou et al., Haptic In-Vehicle Gesture Controls, Adjunct Proceedings of the 9th International ACM Conference on Automotive User Interfaces and Interactive Vehicular Applications (AutomotiveUI '17), Sep. 24-27, 2017 (6 pages).
GitHub—danfis/libccd: Library for collision detection between two convex shapes, Mar. 26, 2020, pp. 1-6.
GitHub—IntelRealSense/hand_tracking_samples: researc codebase for depth-based hand pose estimation using dynamics based tracking and CNNs, Mar. 26, 2020, 3 pages.
Gokturk, et al., "ATime-of-Flight Depth Sensor-System Description, Issues and Solutions," Published in: 2004 Conference on Computer Vision and Pattern Recognition Workshop, Date of Conference: Jun. 27-Jul. 2, 2004, 9 pages.
Hasegawa, K. and Shinoda, H. (2013) "Aerial Display of Vibrotactile Sensation with High Spatial-Temporal Resolution using Large Aperture Airbourne Ultrasound Phased Array", University of Tokyo (6 pages).
Hilleges et al. Interactions in the air: adding further depth to interactive tabletops, UIST '09: Proceedings of the 22nd annual ACM symposium on User interface software and technologyOct. 2009 pp. 139-148.
Hoshi T et al, "Noncontact Tactile Display Based on Radiation Pressure of Airborne Ultrasound", IEEE Transactions on Haptics, IEEE, USA, (Jul. 1, 2010), vol. 3, No. 3, ISSN 1939-1412, pp. 155-165.
Hoshi, T., Development of Aerial-Input and Aerial-Tactile-Feedback System, IEEE World Haptics Conference 2011, p. 569-573.
Hoshi, T., Handwriting Transmission System Using Noncontact Tactile Display, IEEE Haptics Symposium 2012 pp. 399-401.
Hoshi, T., Non-contact Tactile Sensation Synthesized by Ultrasound Transducers, Third Joint Euro haptics Conference and Symposium on Haptic Interfaces for Virtual Environment and Teleoperator Systems 2009 (5 pages).
Hoshi, T., Touchable Holography, SIGGRAPH 2009, New Orleans, Louisiana, Aug. 3-7, 2009. (1 page).
Hua J, Qin H., Haptics-based dynamic implicit solid modeling, IEEE Trans Vis Comput Graph. Sep.-Oct. 2004;10(5):574-86.
Iddan, et al., "3D Imaging in the Studio (And Elsewhwere . . ." Apr. 2001, 3DV systems Ltd., Yokneam, Isreal, www.3dvsystems.com.il, 9 pages.
Imaginary Phone: Learning Imaginary Interfaces by Transferring Spatial Memory From a Familiar Device Sean Gustafson, Christian Holz and Patrick Baudisch. UIST 2011. (10 pages).
International Preliminary Report on Patentability and Written Opinion issued in corresponding PCT/US2017/035009, dated Dec. 4, 2018, 8 pages.
International Preliminary Report on Patentability for Application No. PCT/EP2017/069569 dated Feb. 5, 2019,11 pages.
International Search Report and Written Opinion for Application No. PCT/GB2018/053738, dated Apr. 11, 2019, 14 pages.
International Search Report and Written Opinion for Application No. PCT/GB2018/053739, dated Jun. 4, 2019, 16 pages.
International Search Report and Written Opinion for Application No. PCT/GB2019/050969, dated Jun. 13, 2019, 15 pages.
International Search Report and Written Opinion for Application No. PCT/GB2019/051223, dated Aug. 8, 2019, 15 pages.
International Search Report and Written Opinion for Application No. PCT/GB2019/052510, dated Jan. 14, 2020, 25 pages.
ISR and WO for PCT/GB2020/050013 (Jul. 13, 2020) (20 pages).
ISR and WO for PCT/GB2020/050926 (Jun. 2, 2020) (16 pages).
ISR and WO for PCT/GB2020/052545 (Jan. 27, 2021) (14 pages).
ISR and WO for PCT/GB2020/052829 (Feb. 1, 2021) (15 pages).
Iwamoto et al. (2008), Non-contact Method for Producing Tactile Sensation Using Airborne Ultrasound, EuroHaptics, pp. 504-513.
Iwamoto et al., Airborne Ultrasound Tactile Display: Supplement, The University of Tokyo 2008 (2 pages).
Iwamoto T et al, "Two-dimensional Scanning Tactile Display using Ultrasound Radiation Pressure", Haptic Interfaces for Virtual Environment and Teleoperator Systems, 20 06 14th Symposium on Alexandria, VA, USA Mar. 25-26, 2006, Piscataway, NJ, USA,IEEE, (Mar. 25, 2006), ISBN 978-1-4244-0226-7, pp. 57-61.
Jager et al., "Air-Coupled 40-KHZ Ultrasonic 2D-Phased Array Based on a 3D-Printed Waveguide Structure", 2017 IEEE, 4 pages.
Japanese Office Action (with English language translation) for Application No. 2017-514569, dated Mar. 31, 3019, 10 pages.
Jonathan Taylor et al., Articulated Distance Fields for Ultra-Fast Tracking of Hands Interacting, ACM Transactions on Graphics, vol. 36, No. 4, Article 244, Publication Date: Nov. 2017, pp. 1-12.
Jonathan Taylor et al., Efficient and Precise Interactive Hand Tracking Through Joint, Continuous Optimization of Pose and Correspondences, SIGGRAPH '16 Technical Paper, Jul. 24-28, 2016, Anaheim, CA, ISBN: 978-1-4503-4279-87/16/07, pp. 1-12.
Jonathan Tompson et al., Real-Time Continuous Pose Recovery of Human Hands Using Convolutional Networks, ACM Trans. Graph. 33, 5, Article 169, Aug. 2014, pp. 1-10.
K. Jia, Dynamic properties of micro-particles in ultrasonic transportation using phase-controlled standing waves, J. Applied Physics 116, n. 16 (2014) (12 pages).
Kaiming He et al., Deep Residual Learning for Image Recognition, http://image-net.org/challenges/LSVRC/2015/ and http://mscoco.org/dataset/#detections-challenge2015, Dec. 10, 2015, pp. 1-12.
Kamakura, T. and Aoki, K. (2006) "A Highly Directional Audio System using a Parametric Array in Air" WESPAC IX 2006 (8 pages).
Kolb, et al., "Time-of-Flight Cameras in Computer Graphics," Computer Graphics forum, vol. 29 (2010), No. 1, pp. 141-159.
Konstantinos Bousmalis et al., Domain Separation Networks, 29th Conference on Neural Information Processing Sysgtems (NIPS 2016), Barcelona, Spain. Aug. 22, 2016, pp. 1-15.
Krim, et al., "Two Decades of Array Signal Processing Research—The Parametric Approach", IEEE Signal Processing Magazine, Jul. 1996, pp. 67-94.
Lang, Robert, "3D Time-of-Flight Distance Measurement with Custom Solid-State Image Sensors in CMOS/CCD—Technology", A dissertation submitted to Department of EE and CS at Univ. of Siegen, dated Jun. 28, 2000, 223 pages.
Large et al.,Feel the noise: Mid-air ultrasound haptics as a novel human-vehicle interaction paradigm, Applied Ergonomics (2019) (10 pages).
Li, Larry, "Time-of-Flight Camera—An Introduction," Texas Instruments, Technical White Paper, SLOA190B—Jan. 2014 Revised May 2014, 10 pages.
Light, E.D., Progress in Two Dimensional Arrays for Real Time Volumetric Imaging, 1998 (17 pages).
M. Barmatz et al., "Acoustic radiation potential on a sphere in plane, cylindrical, and spherical standing wave fields", The Journal of the Acoustical Society of America, New York, NY, US, (Mar. 1, 1985), vol. 77, No. 3, pp. 928-945, XP055389249.
M. Toda, New Type of Matching Layer for Air-Coupled Ultrasonic Transducers, IEEE Transactions on Ultrasonics, Ferroelecthcs, and Frequency Control, vol. 49, No. 7, Jul. 2002 (8 pages).
Mahdi Rad et al., Feature Mapping for Learning Fast and Accurate 3D Pose Inference from Synthetic Images, Mar. 26, 2018, pp. 1-14.
Marco A B Andrade et al., "Matrix method for acoustic levitation simulation", IEEE Transactions on Ultrasonics, Ferroelectricsand Frequency Control, IEEE, US, (Aug. 1, 2011), vol. 58, No. 8, ISSN 0885-3010, pp. 1674-1683.
Marin, About LibHand, LibHand—A Hand Articulation Library, www.libhand.org/index.html, Mar. 26, 2020, pp. 1-2; www.libhand.org/download.html, 1 page; www.libhand.org/examples.html, pp. 1-2.
Markus Oberweger et al., DeepPrior++: Improving Fast and Accurate 3D Hand Pose Estimation, Aug. 28, 2017, pp. 1-10.
Markus Oberweger et al., Hands Deep in Deep Learning for Hand Pose Estimation, Dec. 2, 2016, pp. 1-10.

(56) References Cited

OTHER PUBLICATIONS

Marshall, M., Carter, T., Alexander, J., & Subramanian, S. (2012). Ultratangibles: creating movable tangible objects on interactive tables. In Proceedings of the 2012 ACM annual conference on Human Factors in Computing Systems, (pp. 2185-2188).
Marzo et al., Holographic acoustic elements for manipulation of levitated objects, Nature Communications DOI: I0.1038/ncomms9661 (2015) (7 pages).
Meijster, A., et al., "A General Algorithm for Computing Distance Transforms in Linear Time," Mathematical Morphology and its Applications to Image and Signal Processing, 2002, pp. 331-340.
Mingzhu Lu et al. (2006) Design and experiment of 256-element ultrasound phased array for noninvasive focused ultrasound surgery, Ultrasonics, vol. 44, Supplement, Dec. 22, 2006, pp. e325-e330.
Mueller, GANerated Hands for Real-Time 3D Hand Tracking from Monocular RGB, Eye in-Painting with Exemplar Generative Adversarial Networks, pp. 49-59 (Jun. 1, 2018).
Nina Gaissert, Christian Wallraven, and Heinrich H. Bulthoff, "Visual and Haptic Perceptual Spaces Show High Similarity in Humans", published to Journal of Vision in 2010, available at http://www.journalofvision.org/content/10/11/2 and retrieved on Apr. 22, 2020 (Year: 2010), 20 pages.
Notice of Allowance dated Apr. 22, 2020 for U.S. Appl. No. 15/671,107 (pp. 1-5).
Notice of Allowance dated Dec. 19, 2018 for U.S. Appl. No. 15/665,629 (pp. 1-9).
Notice of Allowance dated Dec. 21, 2018 for U.S. Appl. No. 15/983,864 (pp. 1-7).
Notice of Allowance dated Feb. 10, 2020, for U.S. Appl. No. 16/160,862 (pp. 1-9).
Notice of Allowance dated Feb. 7, 2019 for U.S. Appl. No. 15/851,214 (pp. 1-7).
Notice of Allowance dated Jul. 31, 2019 for U.S. Appl. No. 15/851,214 (pp. 1-9).
Notice of Allowance dated Jul. 31, 2019 for U.S. Appl. No. 16/296,127 (pp. 1-9).
Notice of Allowance dated Jun. 17, 2020 for U.S. Appl. No. 15/210,661 (pp. 1-9).
Notice of Allowance dated May 30, 2019 for U.S. Appl. No. 15/966,213 (pp. 1-9).
Notice of Allowance dated Oct. 1, 2020 for U.S. Appl. No. 15/897,804 (pp. 1-9).
Notice of Allowance dated Oct. 16, 2020 for U.S. Appl. No. 16/159,695 (pp. 1-7).
Notice of Allowance dated Oct. 30, 2020 for U.S. Appl. No. 15/839,184 (pp. 1-9).
Notice of Allowance dated Oct. 6, 2020 for U.S. Appl. No. 16/699,629 (pp. 1-8).
Notice of Allowance dated Sep. 30, 2020 for U.S. Appl. No. 16/401,148 (pp. 1-10).
Notice of Allowance in U.S. Appl. No. 15/210,661 dated Jun. 17, 2020 (22 pages).
Obrist et al., Emotions Mediated Through Mid-Air Haptics, CHI 2015, Apr. 18-23, 2015, Seoul, Republic of Korea. (10 pages).
Obrist et al., Talking about Tactile Experiences, CHI 2013, Apr. 27-May 2, 2013 (10 pages).
Office Action dated Apr. 8, 2020, for U.S. Appl. No. 16/198,959 (pp. 1-17).
Office Action dated Apr. 16, 2020 for U.S. Appl. No. 15/839,184 (pp. 1-8).
Office Action dated Apr. 17, 2020 for U.S. Appl. No. 16/401,148 (pp. 1-15).
Office Action dated Apr. 18, 2019 for U.S. Appl. No. 16/296,127 (pags 1-6).
Office Action dated Apr. 28, 2020 for U.S. Appl. No. 15/396,851 (pp. 1-12).
Office Action dated Apr. 29, 2020 for U.S. Appl. No. 16/374,301 (pp. 1-18).
Office Action dated Apr. 4, 2019 for U.S. Appl. No. 15/897,804 (pp. 1-10).
Office Action dated Aug. 22, 2019 for U.S. Appl. No. 16/160,862 (pp. 1-5).
Office Action dated Dec. 11, 2019 for U.S. Appl. No. 15/959,266 (pp. 1-15).
Office Action dated Dec. 7, 2020 for U.S. Appl. No. 16/563,608 (pp. 1-8).
Office Action dated Feb. 20, 2019 for U.S. Appl. No. 15/623,516 (pp. 1-8).
Office Action dated Feb. 25, 2020 for U.S. Appl. No. 15/960,113 (pp. 1-7).
Office Action dated Feb. 7, 2020 for U.S. Appl. No. 16/159,695 (pp. 1-8).
Office Action dated Jan. 10, 2020 for U.S. Appl. No. 16/228,767 (pp. 1-6).
Office Action dated Jan. 29, 2020 for U.S. Appl. No. 16/198,959 (p. 1-6).
Office Action dated Jul. 10, 2019 for U.S. Appl. No. 15/210,661 (pp. 1-12).
Office Action dated Jul. 26, 2019 for U.S. Appl. No. 16/159,695 (pp. 1-8).
Office Action dated Jul. 9, 2020 for U.S. Appl. No. 16/228,760 (pp. 1-17).
Office Action dated Jun. 19, 2020 for U.S. Appl. No. 16/699,629 (pp. 1-12).
Office Action dated Jun. 25, 2020 for U.S. Appl. No. 16/228,767 (pp. 1-27).
Office Action dated Mar. 11, 2021 for U.S. Appl. No. 16/228,767 (pp. 1-23).
Office Action dated Mar. 20, 2020 for U.S. Appl. No. 15/210,661 (pp. 1-10).
Office Action dated May 16, 2019 for U.S. Appl. No. 15/396,851 (pp. 1-7).
Office Action dated May 18, 2020 for U.S. Appl. No. 15/960,113 (pp. 1-21).
Office Action dated Oct. 17, 2019 for U.S. Appl. No. 15/897,804 (pp. 1-10).
Office Action dated Oct. 31, 2019 for U.S. Appl. No. 15/671,107 (pp. 1-6).
Office Action dated Oct. 7, 2019 for U.S. Appl. No. 15/396,851 (pp. 1-9).
Office Action dated Sep. 18, 2020 for U.S. Appl. No. 15/396,851 (pp. 1-14).
Office Action dated Sep. 21, 2020 for U.S. Appl. No. 16/198,959 (pp. 1-17).
OGRECave/ogre—GitHub: ogre/Samples/Media/materials at 7de80a7483f20b50f2b10d7ac6de9d9c6c87d364, Mar. 26, 2020, 1 page.
Optimal regularisation for acoustic source reconstruction by inverse methods, Y. Kim, P.A. Nelson, Institute of Sound and Vibration Research, University of Southampton, Southampton, SO17 1BJ, Uk; 25 pages.
Oscar Martínez-Graullera et al., "2D array design based on Fermat spiral for ultrasound imaging", Ultrasonics, (Feb. 1, 2010), vol. 50, No. 2, ISSN 0041-624X, pp. 280-289, XP055210119.
Partial International Search Report for Application No. PCT/GB2018/053735, dated Apr. 12, 2019, 14 pages.
Partial ISR for Application No. PCT/GB2020/050013 dated May 19, 2020 (16 pages).
PCT Partial International Search Report for Application No. PCT/GB2018/053404 dated Feb. 25, 2019, 13 pages.
Péter Tamás Kovács et al., "Tangible Holographic 3D Objects with Virtual Touch", Interactive Tabletops & Surfaces, ACM, 2 Penn Plaza, Suite 701 New York NY 10121-0701 USA, (Nov. 15, 2015), ISBN 978-1-4503-3899-8, pp. 319-324.
Phys.org, Touchable Hologram Becomes Reality, Aug. 6, 2009, by Lisa Zyga (2 pages).
Pompei, F.J. (2002), "Sound from Ultrasound: The Parametric Array as an Audible Sound Source", Massachusetts Institute of Technology (132 pages).
Rocchesso et al., Accessing and Selecting Menu Items by In-Air Touch, ACM CHItaly'19, Sep. 23-25, 2019, Padova, Italy (9 pages).

(56) References Cited

OTHER PUBLICATIONS

Schmidt, Ralph, "Multiple Emitter Location and Signal Parameter Estimation" IEEE Transactions of Antenna and Propagation, vol. AP-34, No. 3, Mar. 1986, pp. 276-280.
Sean Gustafson et al., "Imaginary Phone", Proceedings of the 24th Annual ACM Symposium on User Interface Software and Techology: Oct. 16-19, 2011, Santa Barbara, CA, USA, ACM, New York, NY, Oct. 16, 2011, pp. 283-292, XP058006125, DOI: 10.1145/2047196.2047233, ISBN: 978-1-4503-0716-1.
Search report and Written Opinion of ISA for PCT/GB2015/050417 dated Jul. 8, 2016 (20 pages).
Search report and Written Opinion of ISA for PCT/GB2015/050421 dated Jul. 8, 2016 (15 pages).
Search report and Written Opinion of ISA for PCT/GB2017/050012 dated Jun. 8, 2017. (18 pages).
Search Report by EPO for EP 17748466 dated Jan. 13, 2021 (16 pages).
Search Report for GB1308274.8 dated Nov. 11, 2013. (2 pages).
Search Report for GB1415923.0 dated Mar. 11, 2015. (1 page).
Search Report for PCT/GB/2017/053729 dated Mar. 15, 2018 (16 pages).
Search Report for PCT/GB/2017/053880 dated Mar. 21, 2018. (13 pages).
Search report for PCT/GB2014/051319 dated Dec. 8, 2014 (4 pages).
Search report for PCT/GB2015/052507 dated Mar. 11, 2020 (19 pages).
Search report for PCT/GB2015/052578 dated Oct. 26, 2015 (12 pages).
Search report for PCT/GB2015/052916 dated Feb. 26, 2020 (18 pages).
Search Report for PCT/GB2017/052332 dated Oct. 10, 2017 (12 pages).
Search report for PCT/GB2018/051061 dated Sep. 26, 2018 (17 pages).
Search report for PCT/US2018/028966 dated Jul. 13, 2018 (43 pages).
Sergey Ioffe et al., Batch Normalization: Accelerating Deep Network Training by Reducing Internal Covariat Shift, Mar. 2, 2015, pp. 1-11.
Seungryul, Pushing the Envelope for RGB-based Dense 3D Hand Pose Estimation for RGB-based Desne 3D Hand Pose Estimation via Neural Rendering, arXiv:1904.04196v2 [cs.CV] Apr. 9, 2019 (5 pages).
Shakeri, G., Williamson, J. H. and Brewster, S. (2018) May the Force Be with You: Ultrasound Haptic Feedback for Mid-Air Gesture Interaction in Cars. In: 10th International ACM Conference on Automotive User Interfaces and Interactive Vehicular Applications (AutomotiveUI 2018) (11 pages).
Shanxin Yuan et al., BigHand2.2M Bechmark: Hand Pose Dataset and State of the Art Analysis, Dec. 9, 2017, pp. 1-9.
Shome Subhra Das, Detectioin of Self Intersection in Synthetic Hand Pose Generators, 2017 Fifteenth IAPR International Conference on Machine Vision Applications (MVA), Nagoya University, Nagoya, Japan, May 8-12, 2017, pp. 354-357.
Sixth Sense webpage, http://www.pranavmistry.com/projects/sixthsense/Accessed Nov. 30, 2018, 7 pages.
Stan Melax et al., Dynamics Based 3D Skeletal Hand Tracking, May 22, 2017, pp. 1-8.
Steve Guest et al., "Audiotactile interactions in roughness perception", Exp. Brain Res (2002) 146:161-171, DOI 10.1007/00221-002-1164-, /Accepted: May 16, 2002/Published online: Jul. 26, 2002, Springer-Verlag 2002, (11 pages).
Sylvia Gebhardt, Ultrasonic Transducer Arrays for Particle Manipulation (date unknown) (2 pages).
Takahashi Dean: "Ultrahaptics shows off sense of touch in virtual reality", Dec. 10, 2016 (Dec. 10, 2016), XP055556416, Retrieved from the Internet: URL: https://venturebeat.com/2016/12/10/ultrahaptics-shows-off-sense-of-touch-in-virtual-reality/ [retrieved on Feb. 13, 2019] 4 pages.

Takahashi, M. et al., Large Aperture Airborne Ultrasound Tactile Display Using Distributed Array Units, SICE Annual Conference 2010 p. 359-62.
Takayuki et al., "Noncontact Tactile Display Based on Radiation Pressure of Airborne Ultrasound" IEEE Transactions on Haptics vol. 3, No. 3, p. 165 (2010).
Teixeira, et al., "A brief introduction to Microsoft's Kinect Sensor," Kinect, 26 pages, retrieved Nov. 2018.
Toby Sharp et al., Accurate, Robust, and Flexible Real-time Hand Tracking, CHI '15, Apr. 18-23, 2015, Seoul, Republic of Korea, ACM 978-1-4503-3145-6/15/04, pp. 1-10.
Tom Carter et al, "UltraHaptics: Multi-Point Mid-Air Haptic Feedback for Touch Surfaces", Proceedings of the 26th Annual ACM Symposium on User Interface Software and Technology, UIST'13, New York, New York, USA, (Jan. 1, 2013), ISBN 978-1-45-032268-3, pp. 505-514.
Tom Nelligan and Dan Kass, Intro to Ultrasonic Phased Array (date unknown) (8 pages).
Vincent Lepetit et al., Model Based Augmentation and Testing of an Annotated Hand Pose Dataset, ResearchGate, https://www.researchgate.net/publication/307910344, Sep. 2016, 13 pages.
Wang et al., Device-Free Gesture Tracking Using Acoustic Signals, ACM MobiCom '16, pp. 82-94 (13 pages).
Wilson et al., Perception of Ultrasonic Haptic Feedback on the Hand: Localisation and Apparent Motion, CHI 2014, April 26-May 1, 2014, Toronto, Ontario, Canada. (10 pages).
Wooh et al., "Optimum beam steering of linear phased arays," Wave Motion 29 (1999) pp. 245-265, 21 pages.
Xin Cheng et al, "Computation of the acoustic radiation force on a sphere based on the 3-D FDTD method", Piezoelectricity, Acoustic Waves and Device Applications (SPAWDA), 2010 Symposium On, IEEE, (Dec. 10, 2010), ISBN 978-1-4244-9822-2, pp. 236-239.
Xu Hongyi et al, "6-DoF Haptic Rendering Using Continuous Collision Detection between Points and Signed Distance Fields", IEEE Transactions on Haptics, IEEE, USA, vol. 10, No. 2, ISSN 1939-1412, (Sep. 27, 2016), pp. 151-161, (Jun. 16, 2017).
Yang Ling et al, "Phase-coded approach for controllable generation of acoustical vortices", Journal of Applied Physics, American Institute of Physics, US, vol. 113, No. 15, ISSN 0021-8979, (Apr. 21, 2013), pp. 154904-154904.
Yarin Gal et al., Dropout as a Bayesian Approximation: Representing Model Uncertainty in Deep Learning, Oct. 4, 2016, pp. 1-12, Proceedings of the 33rd International Conference on Machine Learning, New York, NY, USA, 2016, JMLR: W&CP vol. 48.
Yaroslav Ganin et al., Domain-Adversarial Training of Neural Networks, Journal of Machine Learning Research 17 (2016) 1-35, submitted May 2015; published Apr. 2016.
Yaroslav Ganin et al., Unsupervised Domain Adaptataion by Backpropagation, Skolkovo Institute of Science and Technology (Skoltech), Moscow Region, Russia, Proceedings of the 32nd International Conference on Machine Learning, Lille, France, 2015, JMLR: W&CP vol. 37, copyright 2015 by the authors), 11 pages.
Yoshino, K. and Shinoda, H. (2013), "Visio Acoustic Screen for Contactless Touch Interface with Tactile Sensation", University of Tokyo (5 pages).
Zeng, Wejun, "Microsoft Kinect Sensor and Its Effect," IEEE Multimedia, Apr.-Jun. 2012, 7 pages.
Communication Pursuant to Article 94(3) EPC for EP 19723179.8 (dated Feb. 15, 2022), 10 pages.
EPO ISR and WO for PCT/GB2022/050204 (Apr. 7, 2022) (15 pages).
https://radiopaedia.org/articles/physical-principles-of-ultrasound-1?lang=gb (Accessed May 29, 2022).
IN 202047026493 Office Action dated Mar. 8, 2022, 6 pages.
ISR & WO for PCT/GB2021/052946, 15 pages.
Office Action (Final Rejection) dated Mar. 14, 2022 for U.S. Appl. No. 16/564,016 (pp. 1-12).
Office Action (Non-Final Rejection) dated Mar. 4, 2022 for U.S. Appl. No. 16/404,660 (pp. 1-5).
Office Action (Non-Final Rejection) dated Mar. 15, 2022 for U.S. Appl. No. 16/144,474 (pp. 1-13).
Office Action (Non-Final Rejection) dated Apr. 1, 2022 for U.S. Appl. No. 16/229,091 (pp. 1-10).

(56) References Cited

OTHER PUBLICATIONS

Office Action (Non-Final Rejection) dated May 2, 2022 for U.S. Appl. No. 17/068,831 (pp. 1-10).
Office Action (Notice of Allowance and Fees Due (PTOL-85)) dated Mar. 7, 2022 for U.S. Appl. No. 16/600,496 (pp. 1-5).
ISR & WO for PCT/GB2022/051388 (Aug. 30, 2022) (15 pages).
Office Action (Final Rejection) dated Sep. 16, 2022 for U.S. Appl. No. 16/404,660 (pp. 1-6).
Office Action (Non-Final Rejection) dated Aug. 29, 2022 for U.S. Appl. No. 16/995,819 (pp. 1-6).
Office Action (Non-Final Rejection) dated Sep. 21, 2022 for U.S. Appl. No. 17/721,315 (pp. 1-10).
Office Action (Notice of Allowance and Fees Due (PTOL-85)) dated Aug. 24, 2022 for U.S. Appl. No. 16/198,959 (pp. 1-6).
Office Action (Notice of Allowance and Fees Due (PTOL-85)) dated Aug. 31, 2022 for U.S. Appl. No. 16/198,959 (pp. 1-2).
Office Action (Notice of Allowance and Fees Due (PTOL-85)) dated Sep. 7, 2022 for U.S. Appl. No. 17/068,834 (pp. 1-8).
Office Action (Notice of Allowance and Fees Due (PTOL-85)) dated Sep. 8, 2022 for U.S. Appl. No. 17/176,899 (pp. 1-8).
Office Action (Notice of Allowance and Fees Due (PTOL-85)) dated Sep. 12, 2022 for U.S. Appl. No. 16/734,479 (pp. 1-7).
EPO Examination Search Report 17 702 910.5 (dated Jun. 23, 2021).
Office Action dated Oct. 29, 2021 forU.S. Appl. No. 16/198,959 (pp. 1-7).
Notice of Allowance dated Nov. 5, 2021 for U.S. Appl. No. 16/899,720 (pp. 1-9).
Corrected Notice of Allowability dated Nov. 24, 2021 for U.S. Appl. No. 16/600,500 (pp. 1-5).
International Search Report and Written Opinion for App. No. PCT/GB2021/051590, dated Nov. 11, 2021,20 pages.
Anonymous: "How does Ultrahaptics technology work? - Ultrahaptics Developer Information", Jul. 31, 2018 (Jul. 31, 2018), XP055839320, Retrieved from the Internet: URL:https://developer.ultrahaptics.com/knowledgebase/haptics-overview/ [retrieved on Sep. 8, 2021].
Office Action (Notice of Allowance and Fees Due (PTOL-85)) dated Dec. 14, 2021 for U.S. Appl. No. 17/170,841 (pp. 1-8).
EPO Application 18 725 358.8 Examination Report dated Sep. 22, 2021.
EPO 21186570.4 Extended Search Report dated Oct. 29, 2021.
Office Action (Notice of Allowance and Fees Due (PTOL-85)) dated Jan. 18, 2022 for U.S. Appl. No. 16/899,720 (pp. 1-2).
Office Action (Non-Final Rejection) dated Jan. 24, 2022 for U.S. Appl. No. 16/228,767 (pp. 1-22).
Office Action (Non-Final Rejection) dated Jan. 21, 2022 for U.S. Appl. No. 17/068,834 (pp. 1-12).
Office Action (Notice of Allowance and Fees Due (PTOL-85)) dated Feb. 11, 2022 for U.S. Appl. No. 16/228,760 (pp. 1-8).
ISR and WO for PCT/GB2020/052829 (Feb. 10, 2021) (15 pages).
EPO Examination Report 17 748 4656.4 (dated Jan. 12, 2021) (16 pages).
Office Action (Notice of Allowance and Fees Due (PTOL-85)) dated Feb. 28, 2022 for U.S. Appl. No. 17/068,825 (pp. 1-7).
Mohamed Yacine Tsalamlal, Non-Intrusive Haptic Interfaces: State-of-the Art Survey, HAID 2013, LNCS 7989, pp. 1-9, 2013.
EPO Communication for Application 18 811 906.9 (dated Nov. 29, 2021) (15 pages).
ISR and WO for PCT/GB2021/052415 (Dec. 22, 2021) (16 pages).
Gareth Young et al.. Designing Mid-Air Haptic Gesture Controlled User Interfaces for Cars, PACM on Human-Computer Interactions, Jun. 2020 (24 pages).
Azad et al., Deep domain adaptation under deep label scarcity. arXiv preprint arXiv: 1809.08097 (2018) (Year: 2018).
Wang et al., Few-shot adaptive faster r-cnn. In Proceedings of the IEEE/CVF Conference on Computer Vision and Pattern Recognition, pp. 7173-7182. 2019. (Year: 2019).
Der et al., Inverse kinematics for reduced deformable models. ACM Transactions on graphics (TOG) 25, No. 3 (2006) 1174-1179 (Year: 2006).
Seo et al., "Improved numerical inverse kinematics for human pose estimation," Opt. Eng. 50(3 037001 (Mar. 1, 2011) https://doi.org/10.1117/1.3549255 (Year: 2011).
Boureau et al.,"A theoretical analysis of feature pooling in visual recognition." In Proceedings of the 27th international conference on machine learning (ICML-10), pp. 111-118. 2010. (Year: 2010).
Duka, "Neural network based inverse kinematics solution for trajectory tracking of a robotic arm." Procedia Technology 12 (2014) 20-27. (Year: 2014).
Almusawi et al., "A new artificial neural network approach in solving inverse kinematics of robotic arm (denso vp6242). " Computational intelligence and neuroscience 2016 (2016). (Year: 2016).
Oikonomidis et al., "Efficient model-based 3D tracking of hand articulations using Kinect." In BmVC, vol. 1, No. 2, p. 3. 2011. (Year: 2011).
Office Action (Non-Final Rejection) dated May 25, 2022 for U.S. Appl. No. 16/843,281 (pp. 1-28).
Certon, D., Felix, N., Lacaze, E., Teston, F., & Patat, F. (2001). Investigation of cross-coupling in 1-3 piezocomposite arrays. ieee transactions on ultrasonics, ferroelectrics, and frequency control, 48(1), 85-92.
Certon, D., Felix, N., Hue, P. T. H., Patat, F., & Lethiecq, M. (Oct. 1999). Evaluation of laser probe performances for measuring cross-coupling in 1-3 piezocomposite arrays. In 1999 IEEE Ultrasonics Symposium. Proceedings. International Symposium (Cat. No. 99CH37027) (vol. 2, pp. 1091-1094).
DeSilets, C. S. (1978). Transducer arrays suitable for acoustic imaging (No. GL-2833). Stanford Univ CA Edward L Ginzton Lab of Physics.
Walter, S., Nieweglowski, K., Rebenklau, L., Wolter, K. J., Lamek, B., Schubert, F., . . . & Meyendorf, N. (May 2008). Manufacturing and electrical interconnection of piezoelectric 1-3 composite materials for phased array ultrasonic transducers. In 2008 31st International Spring Seminar on Electronics Technology (pp. 255-260).
Patricio Rodrigues, E., Francisco de Oliveira, T., Yassunori Matuda, M., & Buiochi, F. (Sep. 2019). Design and Construction of a 2-D Phased Array Ultrasonic Transducer for Coupling in Water. In Inter-Noise and Noise-Con Congress and Conference Proceedings (vol. 259, No. 4, pp. 5720-5731). Institute of Noise Control Engineering.
Henneberg, J., Geriach, A., Storck, H., Cebulla, H., & Marburg, S. (2018). Reducing mechanical cross-coupling in phased array transducers using stop band material as backing Journal of Sound and Vibration, 424, 352-364.
Bybi, A., Grondel, S., Mzerd, A., Granger, C., Garoum, M., & Assaad, J. (2019). Investigation of cross-coupling in piezoelectric transducer arrays and correction. International Journal of Engineering and Technology Innovation, 9(4), 287.
Beranek, L., & Mellow, T. (2019). Acoustics: Sound Fields, Transducers and Vibration. Academic Press.
Office Action (Non-Final Rejection) dated Jun. 9, 2022 for U.S. Appl. No. 17/080,840 (pp. 1-9).
Office Action (Non-Final Rejection) dated Jun. 27, 2022 for U.S. Appl. No. 16/198,959 (pp. 1-17).
Office Action (Non-Final Rejection) dated Jun. 27, 2022 for U.S. Appl. No. 16/734,479 (pp. 1-13).
Chang Suk Lee et al., An electrically switchable visible to infra-red dual frequency cholesteric liquid crystal light shutter, J. Mater. Chem. C, 2018, 6, 4243 (7 pages).
Al-Mashhadany, "Inverse Kinematics Problem (IKP) of 6-DOF Manipulator by Locally Recurrent Neural Networks (LRNNs)," Management and Service Science (MASS), International Conference on Management and Service Science., IEEE, Aug. 24, 2010, 5 pages. (Year: 2010).
Guez, "Solution to the inverse kinematic problem in robotics by neural networks." In Proceedings of the 2nd International Conference on Neural Networks, 1988. San Diego, California. (Year: 1988).
Invitatioin to Pay Additional Fees for PCT/GB2022/051821 (dated Oct. 20, 2022).
Mahboob, "Artificial neural networks for learning inverse kinematics of humanoid robot arms." MS Thesis, 2015. (Year: 2015).

(56) References Cited

OTHER PUBLICATIONS

Office Action (Final Rejection) dated Jan. 9, 2023 for U.S. Appl. No. 16/144,474 (pp. 1-16).
Office Action (Final Rejection) dated Nov. 18, 2022 for U.S. Appl. No. 16/228,767 (pp. 1-27).
Office Action (Final Rejection) dated Nov. 18, 2022 for U.S. Appl. No. 17/068,831 (pp. 1-9).
Office Action (Final Rejection) dated Dec. 8, 2022 for U.S. Appl. No. 16/229,091 (pp. 1-9).
Office Action (Final Rejection) dated Dec. 15, 2022 for U.S. Appl. No. 16/843,281 (pp. 1-25).
Office Action (Non-Final Rejection) dated Oct. 17, 2022 for U.S. Appl. No. 17/807,730 (pp. 1-8).
Office Action (Non-Final Rejection) dated Nov. 9, 2022 for U.S. Appl. No. 17/454,823 (pp. 1-16).
Office Action (Non-Final Rejection) dated Nov. 16, 2022 for U.S. Appl. No. 17/134,505 (pp. 1-7).
Office Action (Non-Final Rejection) dated Nov. 16, 2022 for U.S. Appl. No. 17/692,852 (pp. 1-4).
Office Action (Non-Final Rejection) dated Dec. 6, 2022 for U.S. Appl. No. 17/409,783 (pp. 1-7).
Office Action (Non-Final Rejection) dated Dec. 22, 2022 for U.S. Appl. No. 17/457,663 (pp. 1-20).
Office Action (Notice of Allowance and Fees Due (PTOL-85)) dated Oct. 31, 2022 for U.S. Appl. No. 17/068,834 (pp. 1-2).
Office Action (Notice of Allowance and Fees Due (PTOL-85)) dated Oct. 31, 2022 for U.S. Appl. No. 17/176,899 (pp. 1-2).
Office Action (Notice of Allowance and Fees Due (PTOL-85)) dated Nov. 1, 2022 for U.S. Appl. No. 16/404,660 (pp. 1-5).
Office Action (Notice of Allowance and Fees Due (PTOL-85)) dated Nov. 2, 2022 for U.S. Appl. No. 16/734,479 (pp. 1-2).
Office Action (Notice of Allowance and Fees Due (PTOL-85)) dated Nov. 10, 2022 for U.S. Appl. No. 16/198,959 (pp. 1-2).
Office Action (Notice of Allowance and Fees Due (PTOL-85)) dated Nov. 16, 2022 for U.S. Appl. No. 16/404,660 (pp. 1-2).

* cited by examiner

DRIVING TECHNIQUES FOR PHASED-ARRAY SYSTEMS

RELATED APPLICATIONS

This application claims the benefit of the following eight U.S. Provisional Patent Applications, all of which are incorporated by reference in their entirety:
1. Ser. No. 62/433,544, filed on Dec. 13, 2016.
2. Ser. No. 62/436,457, filed on Dec. 20, 2016.
3. Ser. No. 62/437,791, filed on Dec. 22, 2016.
4. Ser. No. 62/438,512, filed on Dec. 23, 2016.
5. Ser. No. 62/594,574, filed on Dec. 5, 2017.
6. Ser. No. 62/594,687, filed on Dec. 5, 2017.
7. Ser. No. 62/594,836, filed on Dec. 5, 2017.
8. Ser. No. 62/594,874, filed on Dec. 5, 2017.

FIELD OF THE DISCLOSURE

The present disclosure relates generally to an improved technique for driving phased array systems, primarily to produce designed acoustic fields for the creation of mid-air haptics, parametric audio, acoustic levitation and acoustic imaging.

BACKGROUND

A continuous distribution of sound energy, which we will refer to as an "acoustic field", can be used for a range of applications including haptic feedback in mid-air.

In this acoustic field, one or more control points can be defined. These control points can be amplitude modulated with a signal and as a result produce vibrotactile feedback in mid-air. An alternative method to produce feedback is to create control points that are not modulated in amplitude and move them around spatially to create spatio-temporal modulation that can be felt.

The minimum size and maximum power of the control points created by the device are dependent on the array layout, geometry and relative location of the control point or points to be created. Due to this, it may not be possible to match the behavior of a control point in one location to the behavior in another. Further complications may arise when a control point is moved dynamically through space. The resultant changes in the haptic function of the point experienced by a user are undesirable and often counter-intuitive, resulting in confusion and loss of experiential immersion. A system that is capable of mitigating the effect of the changes in the air and that is capable of reversing it to provide a consistent haptic experience would be therefore commercially valuable.

Further, it has been shown that a general non-linear optimization system can be used to produce trap points in the air. But the mechanism used for this purpose has a number of flaws, including but not limited to, not evaluating a potential field appropriate to levitation above phased array systems, using an unnecessarily expensive and time consuming optimization process and being limited only to phase manipulation.

Addressing these issues is important, as the traps created by existing systems are not as strong as they could be and fail to scale correctly due to these drawbacks. This makes creating systems that exploit acoustic levitation to provide further visuals for furthering multi-modal approaches and alternative uses for haptic systems difficult.

Further, by defining one or more control points in space, the acoustic field can be controlled. Each point can be assigned a value equating to a desired amplitude at the control point. A physical set of transducers can then be controlled to create an acoustic field exhibiting the desired amplitude at the control points.

Due to the requirements of existing systems, the natural directional components of acoustic phased arrays have received little attention. For instance, high frequency therapeutic medical systems where the object is to focus energy into a small area is sufficiently approximated by scalar pressure (the change in the number of participating air molecules) as to determine to optimal solution to inject energy, therefore not requiring a vector solution. Since to focus a phased array vector behavior (describing the direction of motion of the air molecules) can be ignored in the majority of cases, accomplishing this efficiently has not yet been a priority.

However, creating haptic feedback in mid-air involves exchanging vibrations with human skin. This relies completely on the surface of contact with the wavefront and with the momentum carried by the wave, which is a result of engagement with the vector behaviour of the wave. Not only this, since the system is focused such that the angle of incidence differs between transducer elements more and more, the assumed linear relationship between momentum and pressure breaks down. It is not possible to ignore the vector component in this system, and so the scalar pressure is insufficient to consistently find a suitable solution to create a mid-air haptic effect. For this reason, building awareness of this momentum effect into a device is of commercial interest.

Further, by defining one or more control points in space, the acoustic field can be controlled. Each point can be assigned a value equating to a desired amplitude at the control point. A physical set of transducers can then be controlled to create an acoustic field exhibiting the desired amplitude at the control points.

It has been shown that the calculation of eigenvectors maps to the solution of some very specific purely quadratic constrained problems in matrix algebra. If a matrix could be formed whose eigenvector solved for the control coefficients of transducers given specific problems in mid-air haptics, the solution could form the basis of a device implementation that exhibits simplifications over existing techniques, and so be of value.

Further, to use a reduced representation method to describe basis functions, first a shorthand must be developed that enables a simple (low entropy) description of a useful function in terms of details of the acoustic field.

This description would ideally be something that may be accessible from the point of view of a user.

Having found such an accessible, low entropy representation, there must also be a way to convert it into its equivalent transducer basis (the transducer basis set that describes the basis of transducer acoustic fields of one of potentially many basis functions in a later solution). This would enable a prospective user to design a variety of different structures within the acoustic field, enabling them to build bespoke systems to maximally manipulate energy flow in the field leading to the creation of a system that may use a number of different effects at once, such as focus points, Bessel beams, bottle beams, bending beams etc. These will extend the concept of control points into control regions which encapsulate a richer method of acoustic field control.

It was also discovered that there are some problems that must be dealt with in order to use particle velocity as a stand-in for wave direction when considering momentum transfer in haptics.

Further, performing efficient parallel complex-valued multiplication with the same second operand was a necessity for the large quantities of throughput needed to realize a device with performance metrics in line with those outlined in the requirements documentation. Specifically, to compute in parallel one element of the summation that leads to the computation of a row of a necessary optimization matrix would be sufficient to meet requirements, but only if the subsystem were replicated enough times. For the subsystem to be useful therefore, it must be small and efficient. This pressing need for efficiency yielded a different viewpoint on an old algorithm that gave rise to a new approach to evaluating complex transcendental functions on top of simple multiplication.

In the wider world, this resulting algorithm is applicable anywhere an element of processing hardware must interact efficiently or in real-time with complex-valued data whose modulus cannot be ignored. This includes, but is not limited to, communications, including GPS, wireless, radio and satellite transmission and reception systems, audio processing, phased array systems including mid-air haptics, time-of-flight imaging and digital interferometry, computation of scattering effects and polarization, etc. This may translate to a broader scope of opportunity for this invention.

Volder's algorithm, also known as CORDIC (Voider, J. The CORDIC computing technique 1959), can multiply unit complex values, but is incapable of including the modulus in the second operand of the calculation without further computation beyond that of the basic CORDIC algorithm.

A separate algorithm, invented in 1994 that was implemented by the author some years ago for this reason, is known as BKM after the authors Bajard, Kla and Muller, and further can achieve the goal of full complex-complex multiplication (Bajard, J., Kla, S. and Muller, J.—BKM: A new hardware algorithm for complex elementary functions—1994). However, this algorithm has an involved implementation and thus does not receive as much attention as it otherwise might. The algorithm can achieve full complex-complex multiplication by reducing the complex value operands to their complex logarithm, adding them and then exponentiating to achieve the result.

There is a more efficient way to achieve this complex-valued multiplication and also complex-valued division, in both serial and parallel, with BKM and with the new algorithm in some circumstances.

A 1999 addendum to the BKM algorithm addressed an overly complicated implementation of the complex-valued logarithm, simplifying the implementation somewhat. (Bajard, J. and Imbert, L.—Evaluation of complex elementary functions: a new version of BKM—1999). This BKM method of 1994 and the 1999 addendum forms the algorithm which in this document will be simply termed as BKM.

While trying to optimize the algorithm for inclusion into real hardware, the idea of a new technique became apparent that prioritizes ease-of-integration into our, or more generally any, existing system over evaluating the mathematical functions as described. This new technique, when it was developed into a proof of concept code, turned out to have a number of further emergent properties that make it more promising for general adoption of the hardware implementation than the original algorithm. Additionally, if the exact figures requested of the original technique are required, a further scaling may be applied to retrieve these results, with the algorithm as a whole remaining competitive. In either case, the result is a technique with substantial benefits over the state-of-the-art.

It is known that a quadratic problem with unit norm may be solved by constructing an matrix whose eigenproblem is equivalent to the quadratic problem. A greater than rank-1 quadratic problem matrix may be generated by summing many rank-1 problem matrices and/or extending the null space of an existing problem matrix. By generating a Krylov sub-space of this matrix, an optimized sub-set of the implied basis functions may be generated. By using the Krylov subspace as the basis set to a linear system, a correct or approximated evaluation of the basis set using a number of test functions may be achieved.

Depending on how many eigenvectors are used and from where they are selected, graceful degradation of a complicated set of many basis functions can be achieved, as the power in each subsequent eigenvector is reduced.

Further, a complex-valued linear system for defining the result of an acoustic field shape takes n basis functions and recombines these into a resulting field that describes a desired configuration of acoustic pressure at the carrier frequency.

Up until this point, a control point basis function has only ever been used to actuate control points. Described herein is how to generalize to apply a different set of control test functions to the initial control point or region basis functions.

This is important because it breaks the link between the initial 'palette' of behaviors in the acoustic field and the objective function that the linear system uses. For instance, this may be used to create a basis set of Bessel functions, that may then be used to actuate control points.

BRIEF DESCRIPTION OF THE FIGURES

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

Figure 1:
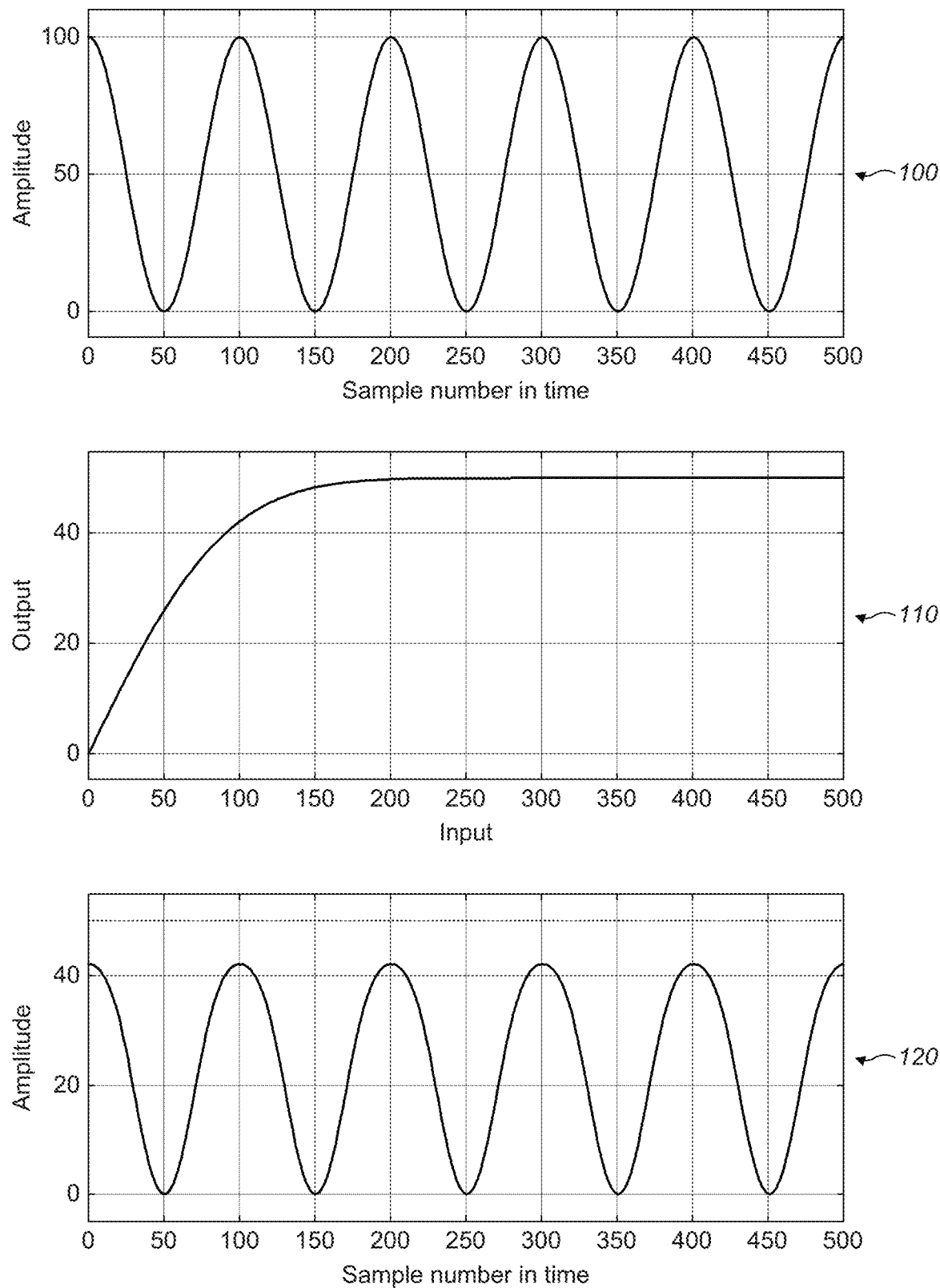
FIGS. 1 and 2 are haptic waveforms of arbitrary dynamic range that can be processed through a non-linear remapping function to create a new waveform of controlled dynamic range.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION

The foregoing techniques, apparatuses and methods may be used in mid-air haptic systems either in combination or separately.

1. DYNAMIC RANGE REDUCTION FOR MID-AIR HAPTIC DEVICES

I. Psychophysical Modelling

The behavior of the system and the haptic output must be calibrated to the way in which humans perceive touch. For instance, in cases where the control point increases in size, the haptic perception is also increased, although the physical amplitude that is created at the control point does not change. Cross-modal effects, such as from audio, serve to enhance haptic feedback if they are correlated. This leads to discrepancies between physically defined control points, necessitating the use of psychophysical modelling steps in order to achieve equivalent perceptions.

II. Remapping Using a Psychohaptic Model

Due to the physical limitations of the playback device, an exact waveform may not be reproducible as specified. The waveform may be constructed in a psychohaptically defined perceptual space. Or it may be comprised of intensities and force measurements on a substantially absolute physical scale, which may be a recording of a haptic texture or an arbitrary constructed waveform potentially expressed alongside further metadata. This waveform represents the behavior of the control point given a 'perfect' mid-air haptic device. This is then perceptually evaluated using a psychophysical model that can describe and quantify the perceptual aspects of the recreation of the control point. The control point may be moving while recreating this haptic effect. The movement may be included as part of the perceptual evaluation of the haptic effect. This can then be reinterpreted into the space of output available to the instance of a mid-air haptic system constrained by the user location, relative geometries and available power limits wherein the system is configured to create a substantially equivalent control point.

The psychohaptic model bestows upon the device the ability to determine how the modulated waveform of the control point may be modified in order to provoke substantially the same haptic response as a perfect device. The process of achieving this remapping may also include a psychoacoustic modelling step in order to prevent the resulting haptic waveform from becoming noisy or to select a more audibly acceptable modulation which is close by in terms of a perceptual haptic space, but has less noise. It is known that many waveforms may be made more haptically powerful by increasing the amount of audible noise. In some situations, this may be noisy enough to be untenable, while in others this may be desirable. A psychoacoustic model may then be used in tandem to provide an audio to haptic trade-off setting that biases the output to make it either quieter or stronger.

III. Psychohaptic Units

If the waveform is defined in a psychohaptic space, wherein amplitudes are intended to feel equivalent, then a unit must be designed that takes into account the psychohaptic effect of the produced control points in mid-air. The most notable of these is the integration of tactile sensations across the hand. The focal region involved for each control point changes size and shape again as a function of the properties of the physical device, and this must be counteracted in the construction of a psychohaptic unit. Such a psychohaptic unit will change what physical control point amplitude it will evaluate to depending of the size and shape of the focal region, counteracting the effects of the integration of touch sensation over a large area. In this way, this approach allows the same number of psychohaptic units to encode an equivalent sensation, preserving haptic equivalence across devices and physical instantiations.

IV. Dynamic Waveform Remapping

In order to achieve the best mapping into the target device, the complete waveform and its trajectory may be considered. However, due to interactivity and thus low latency being a requirement, only part or even individual samples of the waveform may be available. Although the whole waveform may be remapped into the capabilities of the target device, to do this requires that the waveform must be known beforehand and so can be considered to be a pre-processing step on known waveforms. An alternative is to remap the physical properties of each waveform sample in amplitude, because remapping amplitude samples can be achieved in real-time with interactive waveforms, making it more suitable for the provision of haptic feedback in real-time.

Figure 2:
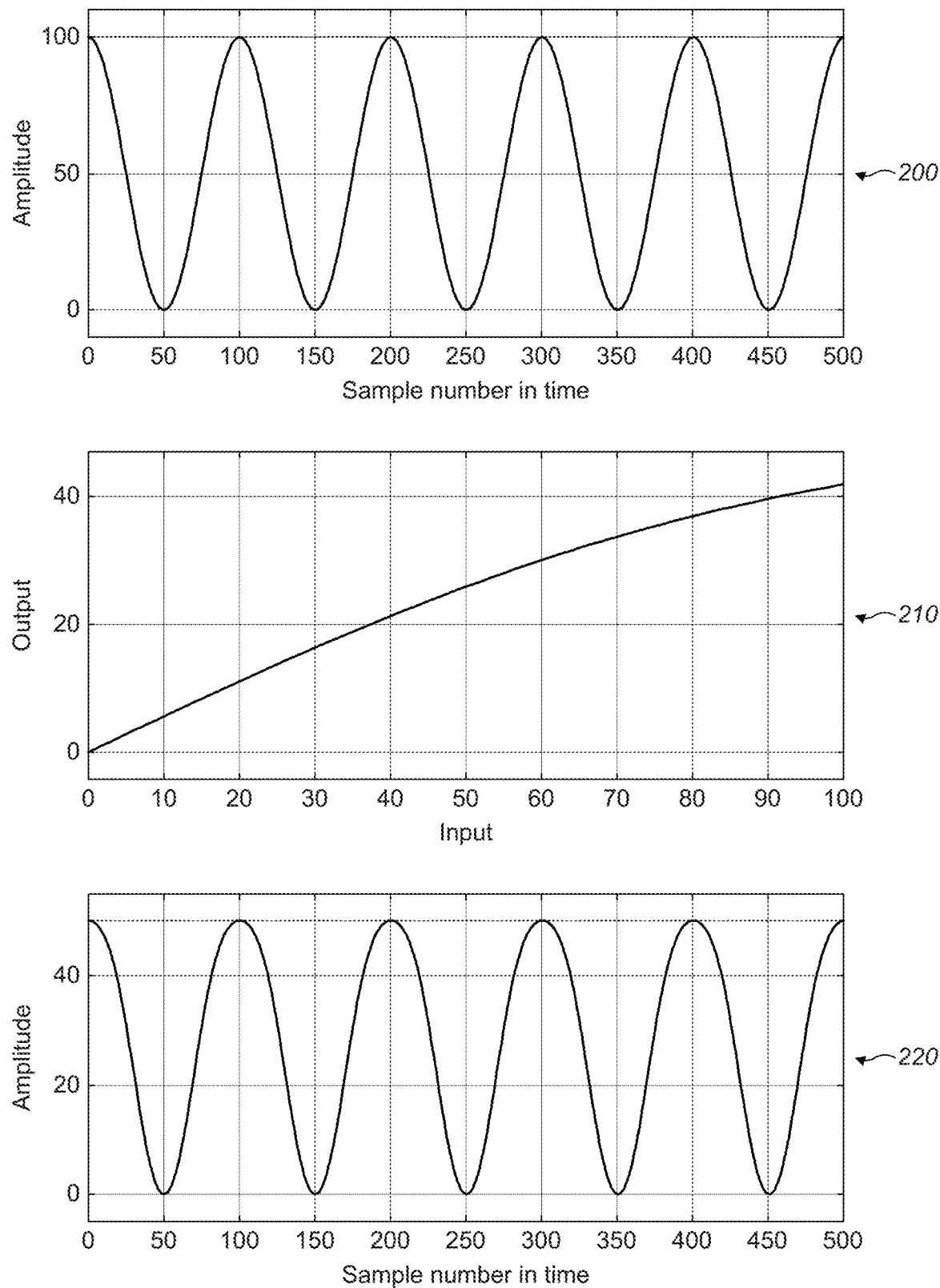

A variety of functions may be considered to be good candidates to provide a remapping for control point amplitude samples. These include log-linear curves as well as sigmoidal functions, which may convincingly reproduce perceptual sensory input on devices with low dynamic range in other modalities. While these curves have generally not required the specification of upper limits in the mapping function, the dynamic range may be more effectively used given that there is a finite quantity of power available as demonstrated in FIGS. 1 and 2. FIG. 1 shows a haptic waveform of arbitrary dynamic range 100 that can be processed through a non-linear remapping function 110 to create a new waveform of controlled dynamic range 120. This can be used to take a haptic waveform of arbitrary dynamic range and convert it into a smaller range. As the waveform can be infinite in amplitude, this does not fill the entire dynamic range of the output, resulting in unused output range. In FIG. 2, similar to FIG. 1, the non-linear function 210 remaps the amplitude waveform 200 into the amplitudes available to the target device 220. Awareness of the extent of the wave enables the remapping function to be tailored exactly to the output range specific to the device. This allows the full range of the device output to be exploited.

For illustration, a minimalist linear rescaling is used in the following examples to describe how the mappings prevent undesirable behavior in mid-air haptic devices.

Figure 3:
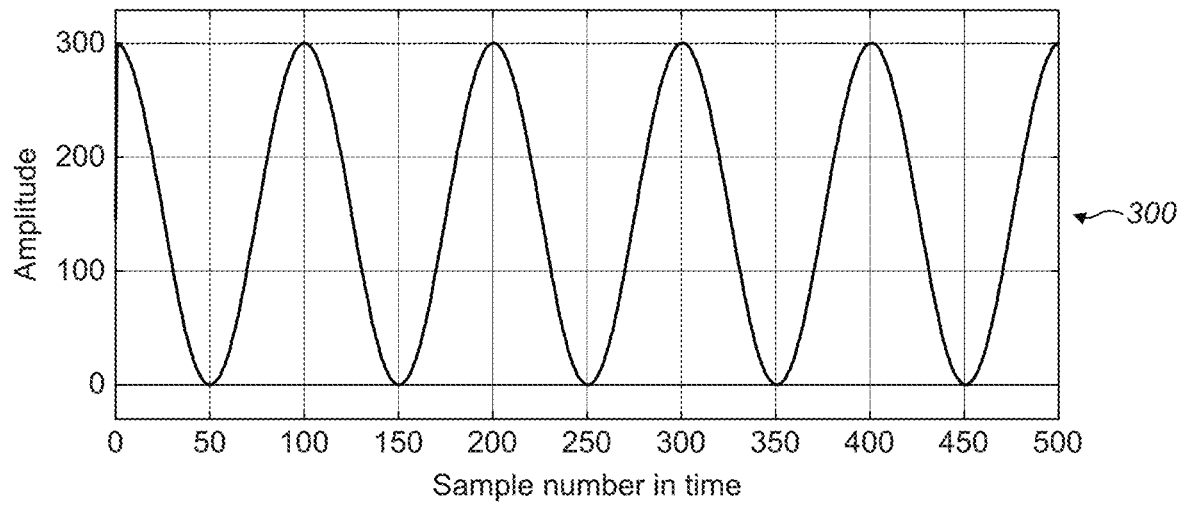
FIGS. 3-12 are the effective amplitude modulation waveforms that result from a control points in different configurations with different range control techniques applied.

Shown in FIG. 3 is a graph 300 where the first step towards achieving the remapping of the waveform into a reproducible perception is to feed data into the solver function that describes the waveform and its limits 300. In FIG. 3 the solid line is $A_1'$ and the dotted line is $A_{1,range}'$. This is the input to the simple waveform remapping function. The y-axis here is in units internal to the device.

This is achieved by defining the maximum amplitude that needs to be reproduced to emit the waveform without clipping this is denoted at each sample time to be $A_{1,range}'$. This is then fed into the solver as input alongside the input waveform amplitude, $A_1'$.

Figure 4:
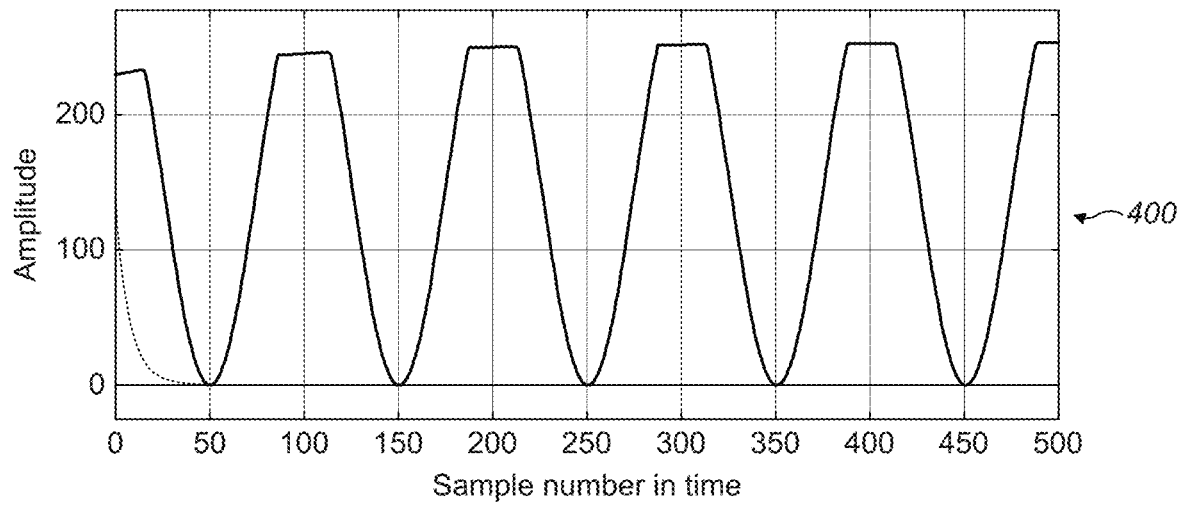

Shown in FIG. 4 is a graph 400 that shows the result of attempting to reproduce this waveform without applying any changes to the input data. The result is that the waveform becomes clipped due to a lack of available power to recreate the necessary amplitude at the control point. In FIG. 4, the solid line is $A_{1,simulated}'$, which is the result of amplitude $(A_1', \chi_1, T)$ and the result of attempting to output directly the user-specified amplitudes in FIG. 1 without regard for the dynamic range of the device.

Defining the physical configuration of active transducers in the system as T and a desired control point amplitude $A_1'$ at position $\chi_i$, auxiliary capabilities of the solver function for the mid-air haptic system can be used to define the function amplitude $(A_1', \chi_1, T)$, which yields either the desired carrier amplitude at the control point if the given device is physically capable of providing this at the given time or alternatively the closest amplitude that can be reproduced at the control point position.

Figure 5:
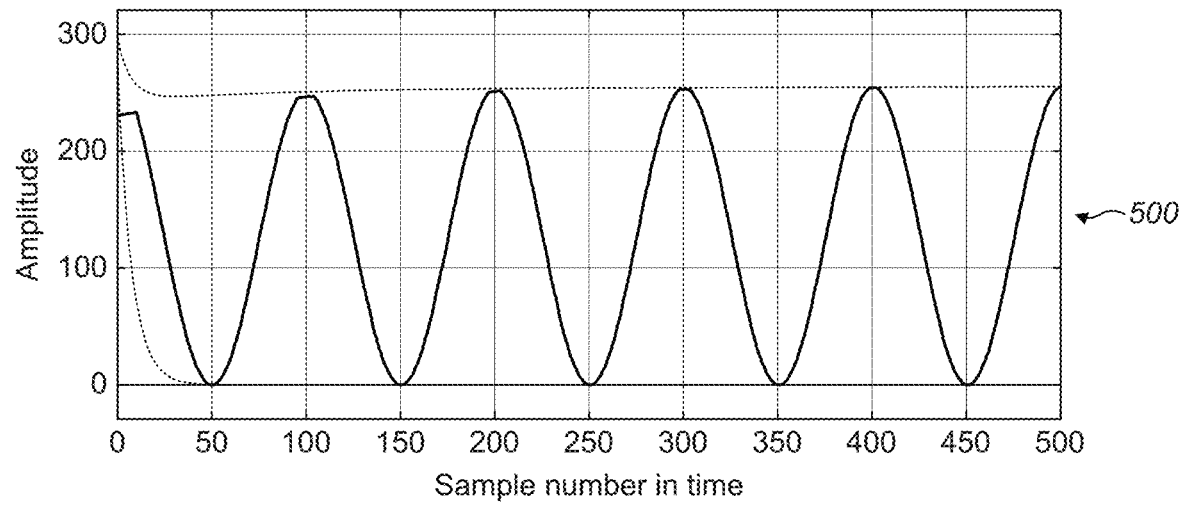

Evaluating $A_{1,limit}$:=amplitude $(A_{1,range}', \chi_1, T)$ then yields the maximum of the range to which the input amplitude can be mapped at this point in time. This does not need to be precise, as the control point does not move much from sample to sample, the value of $A_{1,limit}$ from the previous iteration of the control point may be used. This value may also be filtered in order to remove rounding errors and other sources of noise. In this case, the remapping function takes a single sample of the waveform and remaps this from the interval $[0, A_{1,range}')$ onto the interval $[0, A_{1,limit})$. Shown in FIG. 5 is a graph 500 that produces a direct map from $A_1' \in [0, A_{1,range}')$ onto $A_1 \in [0, A_{1,limit})$, going through the remapping function 500. By remapping the amplitude from $A_1'$ into the range obtained by $A_{1,limit}$:=amplitude $(A_{1,range}', \chi_1, T)$ to the value $A_1$, the clipping of the waveform is prevented and $A_{1,simulated}'=A_1$.

V. Remapping for Multiple Simultaneous Control Points

Figure 6:
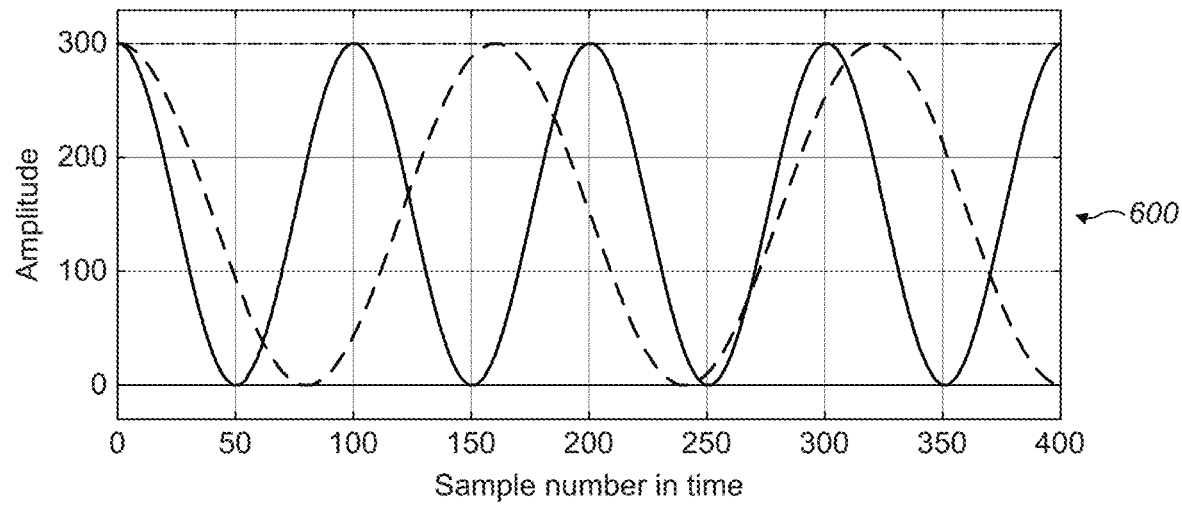

To use the system for multiple control points at once the ranges must be evaluated the same time so that the solver can provide a guarantee that the waveforms can be represented correctly, as in the two sine wave case example in FIG. 6. Shown is a graph 600 where two control points are created with different amplitudes $A_1'$ and $A_2'$ at different points in time. One is moving towards and the other moving across with respect to the transducer array. They are set up to oscillate in amplitude with two sine waves of different frequencies.

Figure 7:
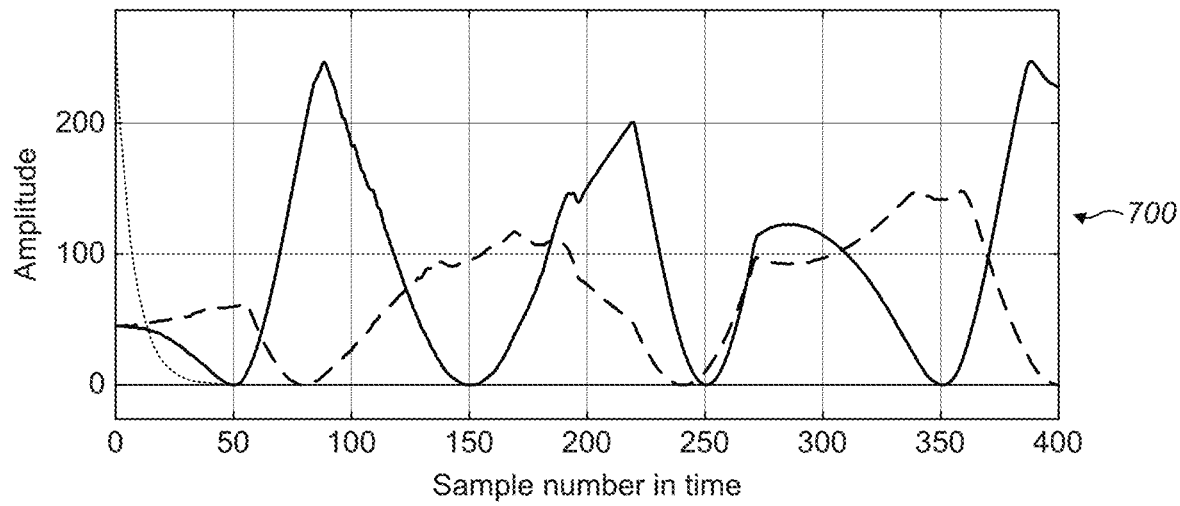

Unlike a single control point wherein violating the power limitations of the device results in underpowered, clipped waveforms, with multiple control points going over the limitations of the device promotes crosstalk between the points, muddling their haptic effects. Shown in FIG. 7 is graph 700 showing an example of two moving control points. FIG. 7 shows an attempt to recreate the two control points using the transducer array that leads to complex and unpredictable behavior as different resonances between the two points are created and replaced, but ultimately fail to reach the desired level.

Figure 8:
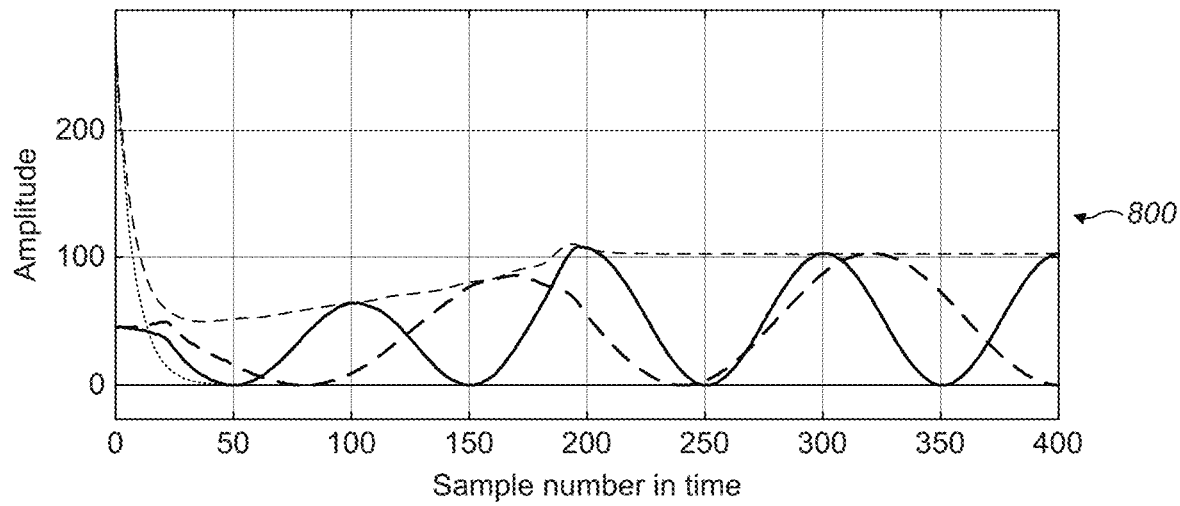

Shown in FIG. 8 is a graph 800 that uses the auxiliary solver evaluation to determine the power limitations present at both points then can be written as $\{A_{1,limit}, A_{2,limit}\}$:=amplitude $(A_{1,range}', A_{2,range}'\chi_1, T)$, leading to the shown waveform. Here. one control point is moving toward the device with the potential to become stronger and the other is moving across the face of the device and away with the potential to become weaker. As can be seen from FIG. 8, due to the dynamic range limiting generated by the solver solution, their waveforms may then be represented as intended and without crosstalk. Thus FIG. 8 shows two points that have their amplitude envelopes reduced to a level that is guaranteed by the solver to be recreated faithfully without error, or with a controlled known level of error. They are the same power because this is the configuration that minimizes the squared amplitude error with the idealized amplitude levels.

VI. Power Redistribution Across Multiple Simultaneous Control Points

The amplitude ranges may be set to different values and even be set dynamically through time in order to manage power levels. In this way, manipulating the ranges can determine the proportion of the array output that is concentrated at a given control point. This is demonstrated for a simple maneuvering of power from one control point to another in FIGS. 9 and 10, but also a more complicated out-of-phase relationship that makes behavioral dynamics between control points such as that demonstrated in FIGS. 11 and 12 possible.

Figure 9:
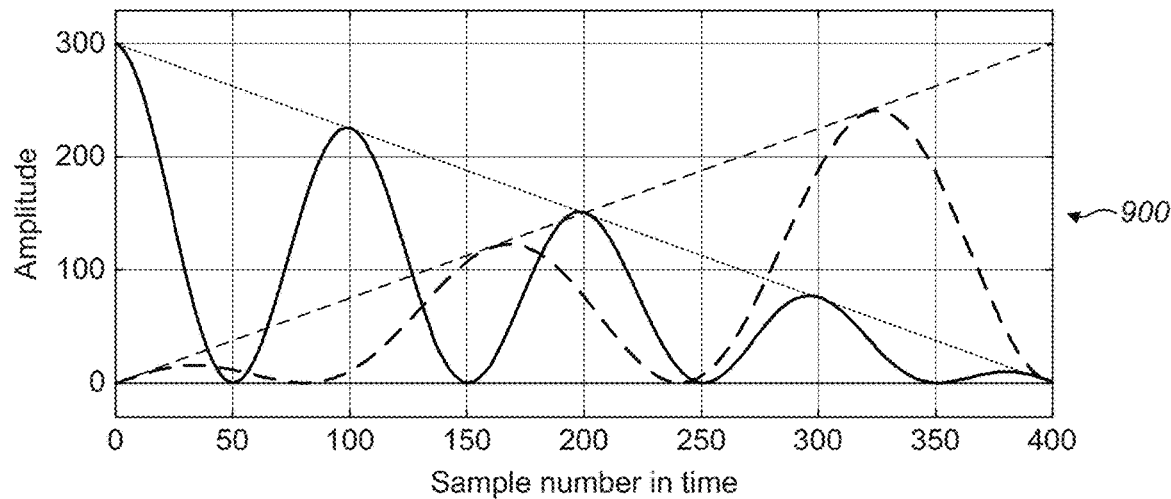
Figure 10:
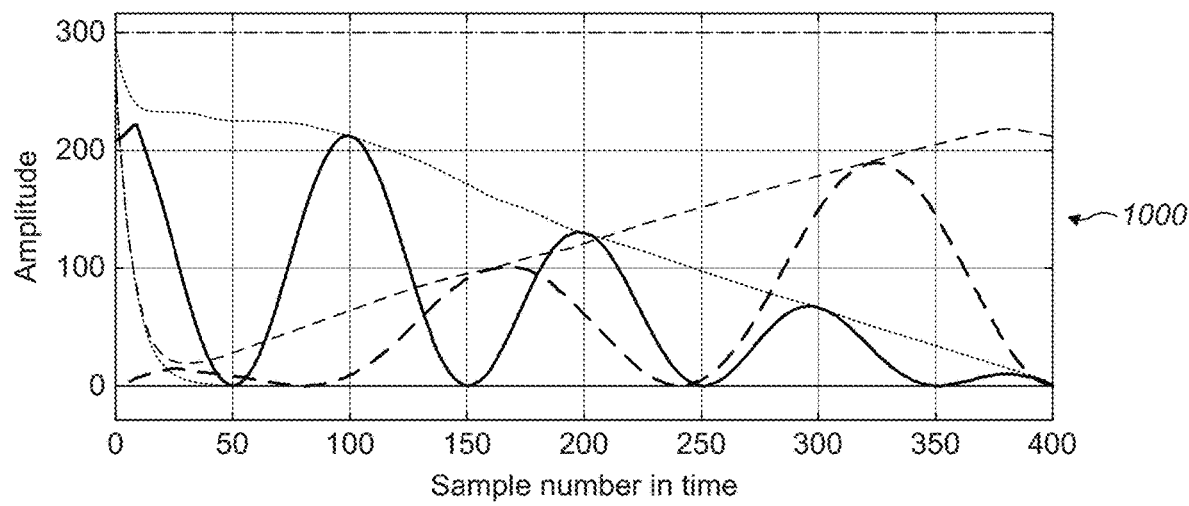

Shown in FIG. 9 is a graph 900 with input waveforms and ranges for the two input control points. These have different waveform ranges, which also double as hints to allow each point to take more or less of the available power from the device. Shown in FIG. 10 is a graph 1000 having the resulting output from the inputs in FIG. 9. In this configuration the power produced by the array is moved from one control point onto the other while they are moving away from and towards the array respectively. Due to this, more power can be used than if it were expected that the control points would be of equal amplitude, as was expected for FIGS. 6, 7 and 8.

Figure 11:
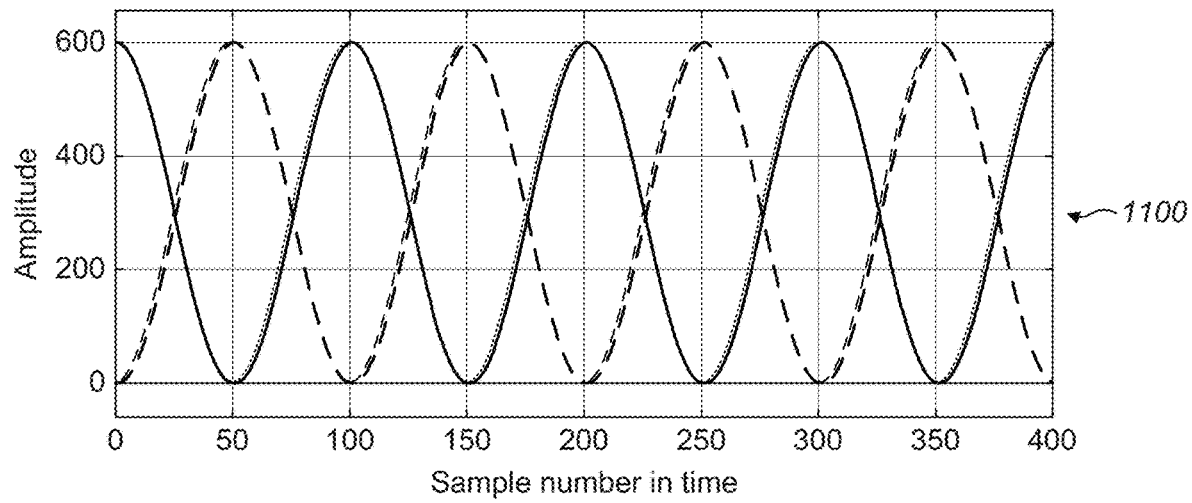
Figure 12:
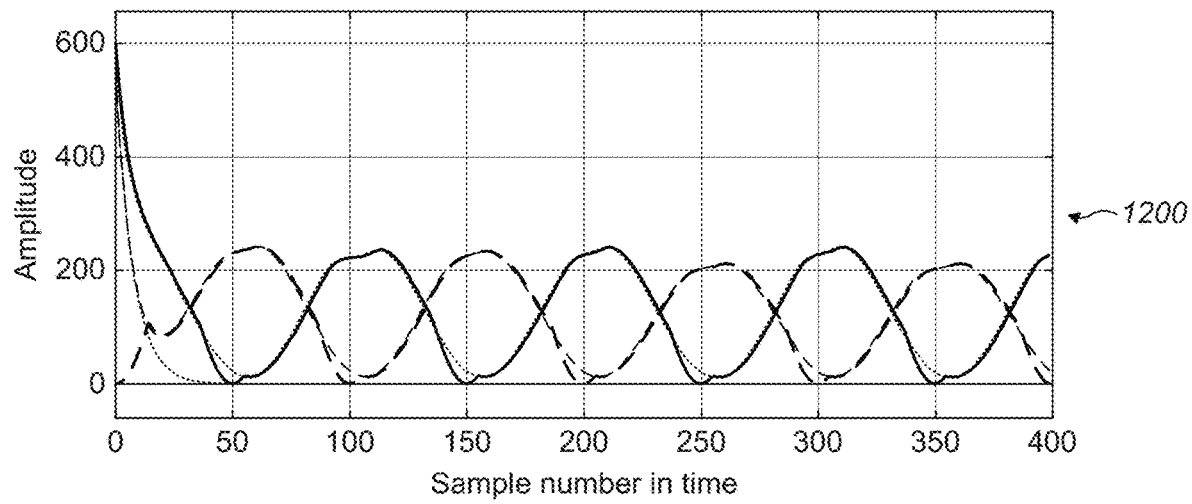

Shown in FIG. 11 is a graph 1100 with alternating functions wherein one control point or control point group ramps up where the others die away in amplitude may be modelled effectively by matching the range to the sinusoid. The result of this is that each waveform is reproduced according to the power requirement of each side of the modulated system, while guaranteeing each side of the system has access to full array power. The result is time slicing without the potential for arbitrary output clipping. Shown in FIG. 12 is a graph 1200 having the resulting output from the inputs in FIG. 11, but without the grouping described. This results in a reduction in output dynamic range because the power budget has been shared unnecessarily between all control points.

2. EFFICIENT CREATION OF TRAP POINTS FOR ACOUSTIC LEVITATION

I. Optimization Objectives for Levitating Spherical Particles

The optimization problem required for levitating particles centers around the use of the Gor'kov energy potential. This is a scalar function that evaluates the energy of each possible position of a particle in an acoustic field. Finding minima or low energy states at spatial positions corresponds to finding potentially stable trap points. However, there are acoustic effects that the Gor'kov potential does not take into account, such as acoustic streaming wherein the acoustic waves induce bulk movement in the fluid. For this reason, it is preferable to also ensure that the trap does not occur in a region of fluctuating pressure, which is often determined to be a viable minimum in the energy potential, as these fluctuations are destructive due to the other factors that are not included in the definition of the potential.

As the direction and magnitude of outside forces such as gravity and acoustic streaming effects cannot be derived from the Gor'kov potential alone, it is often preferable to calculate the Laplacian of the Gor'kov scalar potential. This gives a further degree of control over which axes to prioritize over others in order to generate a more stable arrangement of inwardly pushing forces.

II. Evaluating the Gor'Kov Potential

The Gor'kov potential field, an energy field that enables spherical particles to float due to the existence of energy minima, is described as (in Bruus 2012):

$$U = \frac{4\pi}{3}a^3 \left[ \frac{1}{2}(\kappa_0 - \kappa_p)\tilde{p}^2 - \frac{3}{4}\frac{2(\rho_p - \rho_0)\rho_0}{2\rho_p + \rho_0}\|\tilde{u}\|^2 \right],$$

$$\kappa_0 = \frac{1}{\rho_0 c_0^2},$$

$$\kappa_p = \frac{1}{\rho_p c_p^2},$$

where $c_0$ is the speed of sound through the acoustic medium, $c_p$ is the speed of sound through the spherical particle, $\rho_0$ is the density of the acoustic medium, $\rho_p$ is the density of the spherical particle, the left hand term involving time-averaged pressure $\tilde{p}$ is a representation of potential energy and the right hand term involving the particle velocity vector $\tilde{u}$ is conversely related to the potential energy. As the Gor'kov potential makes the assumption of existing in the active or far-field, these pressure and velocity terms can be exchanged for time-harmonic terms that are in phase. This suggests that the time-harmonic Gor'kov potential field can be rewritten as:

$$U = \frac{4\pi}{3}a^3 \left[ \frac{1}{2}(\kappa_0 - \kappa_p)\|\tilde{p}e^{-i\omega t}\|^2 - \frac{3}{4}\frac{2(\rho_p - \rho_0)\rho_0}{2\rho_p + \rho_0}\|\tilde{u}e^{-i\omega t}\|^2 \right],$$

Extending this to many sources yields:

$$U = \frac{4\pi}{3}a^3$$

$$\left[ \frac{1}{2}(\kappa_0 - \kappa_p)\left\|\sum_{q=1}^{n}\tilde{p}_q e^{-i(\omega t + \varphi_q)}\right\|^2 - \frac{3}{4}\frac{2(\rho_p - \rho_0)\rho_0}{2\rho_p + \rho_0}\left\|\sum_{q=1}^{n}\tilde{u}_q e^{-i(\omega t + \varphi_q)}\right\|^2 \right],$$

The problem with this is that the cross-terms effectively mean that this becomes:

$$U = \frac{4\pi}{3}a^3 \left[ \frac{1}{2}(\kappa_0 - \kappa_p)\sum_{q=1}^{n}\tilde{p}_q e^{-i(\omega t + \varphi_q)} \cdot \overline{\sum_{q=1}^{n}\tilde{p}_q e^{-i(\omega t + \varphi_q)}} - \right.$$

$$\left. \frac{3}{4}\frac{2(\rho_p - \rho_0)\rho_0}{2\rho_p + \rho_0}\sum_{q=1}^{n}\tilde{u}_q e^{-i(\omega t + \varphi_q)} \cdot \overline{\sum_{q=1}^{n}\tilde{u}_q e^{-i(\omega t + \varphi_q)}} \right]$$

resulting in terms that are quadratic and grow in the number of transducers squared.

III. Optimizing the Potential Through an Eigenproblem

The potential definition, neglecting time harmonic effects and considering the pressure and particle velocities input into each transducer, can be written as:

$$x^H = [\alpha_1 e^{-i\varphi_1} \ldots \alpha_q e^{-\varphi_q} \ldots \alpha_n e^{-i\varphi_n}],$$

$$M_{q,r} = \sum_{j=1}^{m} -\frac{4\pi}{3}$$

$$a^3 \left( \frac{1}{2}(\kappa_0 - \kappa_p)\tilde{p}_{j,q}\tilde{p}_{j,r} - \frac{3}{4}\frac{2(\rho_p - \rho_0)\rho_0}{2\rho_p + \rho_0}(\tilde{u}_{j,q,x}\tilde{u}_{j,r,x} + \tilde{u}_{j,q,y}\tilde{u}_{j,r,y} + \tilde{u}_{j,q,z}\tilde{u}_{j,r,z}) \right)$$

$$\tilde{A}_{jq}\tilde{A}_{jr}e^{+i\varphi_{j0q}}e^{-i\varphi_{j0r}},$$

$$U = x^H M x,$$

where j is the index of the trap desired, and the extra $$\tilde{A}_{jq}\tilde{A}_{jr}e^{+i\varphi_{j0q}}e^{-i\varphi_{j0r}}$$

the phase and amplitude changes when moving from transducers q and r to trap point j. Using the constraint $x^H x = 1$, to ensure that the transducers are powered to a non-zero level, the optimal complex transducer activation coefficients to achieve a potential well are given by the eigenvector of M with the maximum eigenvalue.

This choice of x maximises the objective function $x^H M x$ which because of the negative sign in the definition of $M_{q,r}$, yields a minimum in the Gor'kov potential field. This is because $x^H x = 1$ is the definition of an eigenvector, as well as $x^H M x = x^H \lambda x$, given that by definition when $\lambda$, an eigenvalue of the matrix, is maximized while $x^H x = 1$, this must yield a maximum, if it exists. The standard statement of the problem then becomes:

maximize $x^H M x$
subject to $x^H x = 1$,
and $x \in \mathbb{C}^n$.

However, as previously discussed in the literature, minimizing the energy of the Gor'kov field generates a focus and not actually a trap point. To generate a trap point, the pressure fluctuations at the trap are minimized. This is non-trivial, as the definitions of the pressure fluctuations are complex-valued and represent a fluctuating quantity that cannot be meaningfully minimized but brought instead to zero.

IV. Constructing a Null Space Inside the Eigenproblem to Generate Pressure Zeroes Zero pressure conditions can be constructed as a series of constraints that evaluate to a zero pressure at given points in the acoustic field. The pressure can only evaluate to a non-zero value at a given location if there exists part of the solution vector that is parallel to the known optimal pressure focusing solution in the high dimensional phase space. For a trap point j there is a vector $c_j^{\prime H}$ which is:

$$c_j^{\prime H} = \begin{bmatrix} \tilde{A}_{j1} e^{-i\varphi_{j01}} & \ldots & \tilde{A}_{jq} e^{-i\varphi_{j0q}} & \ldots & \tilde{A}_{jn} e^{-i\varphi_{j0n}} \end{bmatrix}$$

Therefore, the constraints for zero pressure at the trap point j may be described as the constraining equation:

$$c_j^{\prime H} x = 0.$$

As it does not matter what the amplitudes are for this and the constraints need to be unit length, so therefore:

$$c_j^H = \frac{c_j^{\prime H}}{\sqrt{c_j^{\prime H} c_j^\prime}}.$$

The standard statement of the problem is therefore:
maximize $x^H M x$
subject to $x^H x = 1$,
and $c_j^H x = 0$, $j \in 1, \ldots, m$.
and $c_j^H, x \in \mathbb{C}^n$.

Taking an eigensystem result from Golub (1973) and restating it for complex-values yields the following argument:

Given the above system with m=1, a characteristic equation can be written for the system as:

$$\varphi(x, \lambda, \mu) = x^H M x - \lambda(x^H x - 1) + 2\mu x^H c,$$

where $\lambda$ and $\mu$ are Lagrange multipliers. This can be differentiated by the conjugate of the x vector, yielding the system:

$$M x - \lambda x + \mu c = 0,$$

Multiplying through by $c^H$ yields:

$$c^H M x - c^H \lambda x + c^H \mu c = 0,$$

$$c^H M x - c^H x \lambda + c^H c \mu = 0,$$

Assuming c is unit length yields $c^H c = 1$, the earlier problem definition yields $c^H = 0$, and substituting both produces:

$$\mu = -c^H M x.$$

Substituting this back into the earlier derivative yields:

$$M x - c^H M x c = \lambda x,$$

Which is:

$$(I - c c^H) M x = \lambda x,$$

As this is the statement of the eigensystem, yet $(I - c c^H) M$ may not be symmetric making eigenvector calculation difficult. However, $I - c c^H$ can be shown to be idempotent $((I - c c^H)^2 = I - c c^H)$ and eigenvalues are unchanged by ordering, yielding:

$$(I - c c^H) M (I - c c^H) x = \lambda x,$$

Extending this to more constraint vectors, there is no problem with further multiplication of the left hand side:

$$(I - c_2 c_2^H)(I - c_1 c_1^H) M (I - c_1 c_1^H)(I - c_2 c_2^H) x = \lambda x,$$

Which finally after many multiplications yields:

$$(I - C C^\dagger) M (I - C C^\dagger) x = \lambda x,$$

$$C = [c_1 \ldots c_j \ldots c_m],$$

where $C^\dagger$ denotes the Moore-Penrose pseudoinverse.

In summary, the solution to the initial problem can be found by determining the eigenvector with greatest eigenvalue of $(I - C C^\dagger) M (I - C C^\dagger)$. The multiplies by $I - C C^\dagger$ can be viewed as adding rank-1 changes that add basis vectors to the null space of the solution matrix.

Finally, it is useful to add support for calculating the Laplacian of the Gor'kov potential in a simple way. The Gor'kov potential solution found herein yields a trap point, but there is no control over from which directions the forces are applied from, and there may even be directions from which there is no force. To achieve this, there is a need to optimize in terms of the most diverging point in the gradient of the potential field and then reweight the gradients of this field. This is then, generally speaking, the Laplacian of the Gor'kov field.

V. Modifications to Generate the Laplacian of the Gor'Kov Field

The modifications to minimize the Laplacian of the Gor'kov field are only necessarily applicable to the M matrix. If the effects of wavefront curvature from each transducer are discarded and regard them as plane waves only, then the singularities that complicate the formulation are removed and particle velocities become constants. The resulting plane waves from each transducer can be rewritten in the form:

$$\phi_q(X - O) = A e^{-i(2\pi(\hat{n}_x x + \hat{n}_y y + \hat{n}_z z)/\lambda + \varphi)}.$$

The matrix element can then, in the Gor'kov without Laplacian case, be represented as the equivalent system:

$$M_{q,r} = \sum_{j=1}^{m} A_{j,q,r} e^{-i(2\pi(\hat{n}_{jq,x} x + \hat{n}_{jq,y} y + \hat{n}_{jq,z} z)/\lambda + \varphi)} e^{+i(2\pi(\hat{n}_{jr,x} x + \hat{n}_{jr,y} y + \hat{n}_{jr,z} z)/\lambda + \varphi)}.$$

where all the constants in $M_{q,r}$ are merged into $A_{j,q,r}$. Taking the Laplacian of this formulation then yields the modified matrix formulation:

$$M_{q,r}^\prime = \sum_{j=1}^{m} A_{j,q,r} \frac{4\pi^2}{\lambda^2} \|\hat{n}_{jq} - \hat{n}_{jr}\|^2 e^{-i\left(\frac{2\pi}{\lambda} \hat{n}_{jq} \cdot X_j + \varphi_{jq}\right)} e^{+i\left(\frac{2\pi}{\lambda} \hat{n}_{jr} \cdot X_j + \varphi_{jr}\right)}.$$

Using this value in place of the corresponding components of the M matrix yields a solution in terms of optimising for the Laplacian of the Gor'kov potential. As the term $$\|\hat{n}_{jq} - \hat{n}_{jr}\|^2$$

can be rewritten as:

$$\|\hat{n}_{jq} - \hat{n}_{jr}\|^2 = (\hat{n}_{jq,x} - \hat{n}_{jr,x})^2 + (\hat{n}_{jq,y} - \hat{n}_{jr,y})^2 + (\hat{n}_{jq,z} - \hat{n}_{jr,z})^2$$

It can also be split into contributions from x, y and z directions:

$$w_x(\hat{n}_{jq,x} - \hat{n}_{jr,x})^2 + w_y(\hat{n}_{jq,y} - \hat{n}_{jr,y})^2 + w_z(\hat{n}_{jq,z} - \hat{n}_{jr,z})^2$$

In this way, weighting can be applied to generate constraint axes and bias the forces generated from each direction.

VI. Implementation in a Device

The system in this document represents a device that can be used to compute one or more levitation traps based on a simple eigensystem solver. This can potentially be implemented in a device firmware in order to create an embodiment capable of using acoustic levitation to constrain, trap and transport items.

This is illustrated in FIGS. 13-16.

Figure 13:
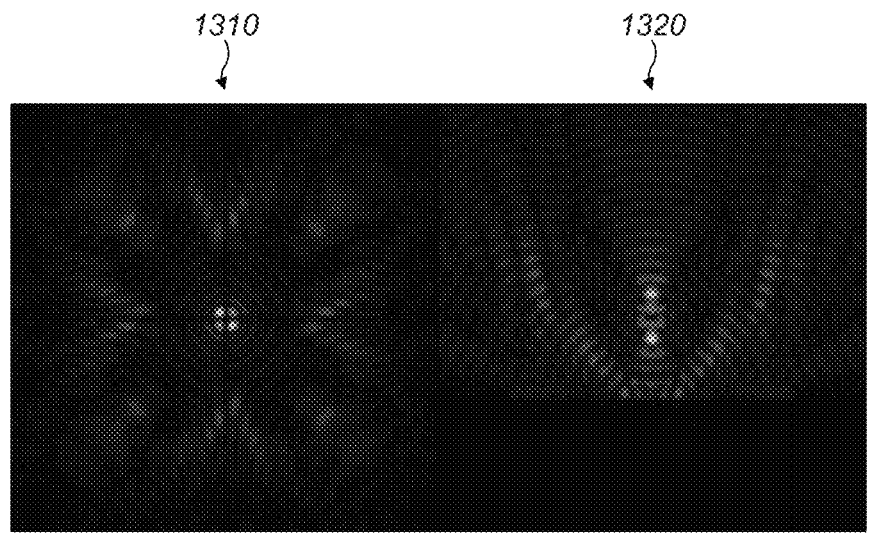
FIGS. 13-16 are projections of acoustic pressure that results from the optimization of Gor'kov-related functions.

FIG. 13 shows a Laplacian of Gor'kov with equal direction weighting. The left side 1310 is the x-y plane parallel to transducer array. The right side 1320 is the x-z plane perpendicular to and slicing through the flat transducer array.

Figure 14:
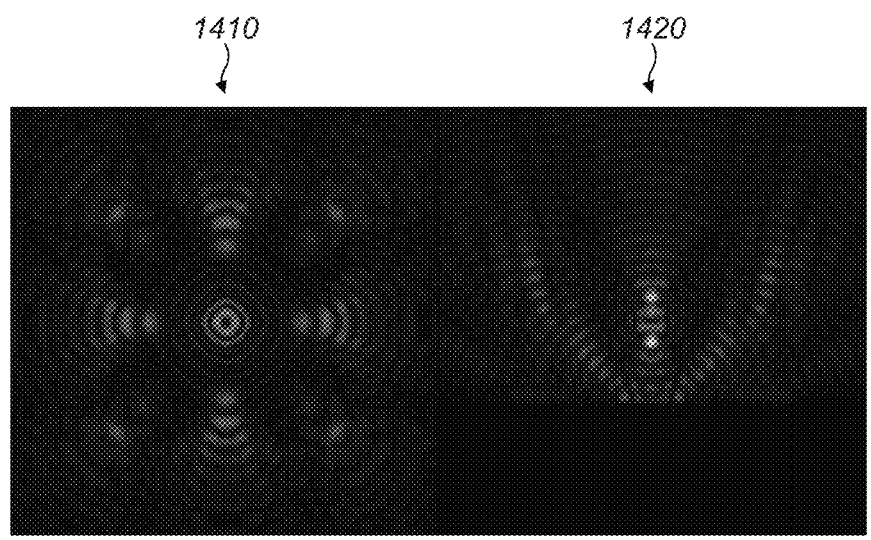

FIG. 14 shows Laplacian of Gor'kov with heavily weighted z-direction. The left side 1410 is the x-y plane parallel to transducer array. The right side 1420 is the x-z plane perpendicular to and slicing through the flat transducer array.

Figure 15:
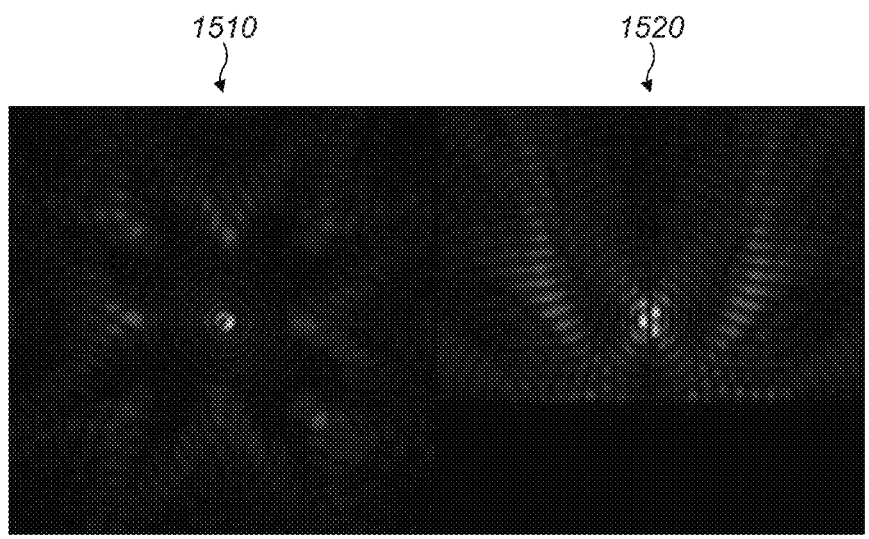

FIG. 15 shows a Gor'kov maximization with zero pressure condition. The left side 1510 is the x-y plane parallel to transducer array, which describes a helical trap as is shown by the non-uniform shade around a ring of uniform intensity. The right side 1520 is the x-z plane perpendicular to and slicing through the flat transducer array underneath.

Figure 16:
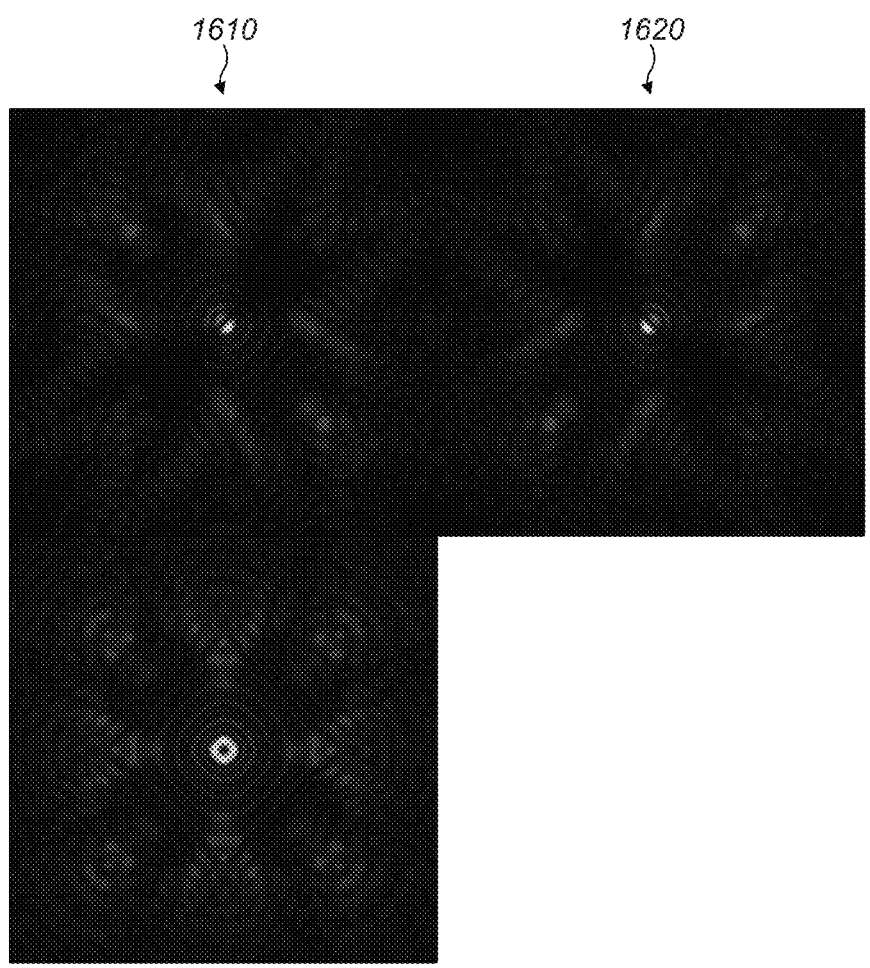

In FIG. 16 further eigenmodes 1610, 1620, 1630 correspond to trap solutions that also solve the core problem. These are less effective as they do not maximize the objective function. This is because the value of the objective function, the modified Gor'kov potential, is less for these modes that are orthogonal to the dominant eigenvector. The value of the objective function achieved is reflected in the eigenvalues associated with each eigenvector. Eigenvectors associated with smaller eigenvalues represent these alternative less effective solutions.

3. PHASED ARRAY DEVICE FOCUSING WITH VECTOR EFFECTS WITH APPLICATIONS TO MID-AIR HAPTICS

I. Active Acoustic Intensity

Active acoustic intensity $I_a$ can be defined using the pressure p and particle velocity vector u of the acoustic medium. For an acoustic wave, this can be described as:

$$I_a = \frac{1}{2}\Re(p \cdot \bar{u}),$$

where the active intensity is a purely real vector quantity. In the near field of a wave source, the reactive field dominates instead $I_r = \frac{1}{2}\Im(p \cdot \bar{u})$. However, in the far field, so beyond one or two wavelengths, $I_r \to 0$. For this reason, $I_a$ will only be considered and assumed to be guaranteed real.

Considering a monochromatic plane wave source, where:

$$p = \tilde{p}e^{-i(\omega t + \varphi)},$$

$$u = \tilde{u}e^{-i(\omega t + \varphi)},$$

results in:

$$I_a = \frac{1}{2}\left(\tilde{p}e^{-i(\omega t + \varphi)} \cdot \overline{\tilde{u}e^{-i(\omega t + \varphi)}}\right),$$

where $\tilde{p}$ is the pressure amplitude, and $\tilde{u}$ is the particle velocity amplitude in each direction.

The sound intensity and thus energy flux transmitted by the wave along a given axis is of interest so the dot product to measure the scalar contribution is:

$$I_a \cdot \hat{n} = \frac{1}{2}\left(\tilde{p}e^{-i(\omega t + \varphi)} \cdot \overline{\tilde{u}e^{-i(\omega t + \varphi)}} \cdot \hat{n}\right)$$

Due to the form of the acoustic wave equations:

$$\frac{\partial^2 p}{\partial t^2} - c_0^2 \nabla^2 p = 0,$$

$$\frac{\partial^2 u}{\partial t^2} - c_0^2 \nabla^2 u = 0,$$

the superposition principle must hold for both pressure and particle velocity vectors. Assuming n acoustic sources and approximating each as a plane wave at the point of interest, then yields the equation:

$$I_a \cdot \hat{n} = \frac{1}{2}\left(\sum_{q=1}^{n} \tilde{p}_q e^{-i(\omega t + \varphi_q)} \cdot \overline{\sum_{q=1}^{n} \tilde{u}_q e^{-i(\omega t + \varphi_q)}} \cdot \hat{n}\right),$$

which for efficiency it is desirable to solve for the appropriate variable using a linear system. This means it cannot be solved for the acoustic intensity in a given direction, as it is made up of two independent variables. Existing techniques solve for the complex-valued scalar pressures $\tilde{p}_q e^{-i\varphi_q}$ and then assume that the direction of the each of the individual waves do not matter or are roughly parallel. Instead, solve for the particle velocity vector $\tilde{u}_q e^{-i\varphi_q}$ because this directly influences the momentum (and the kinetic energy), which for the application of haptic feedback in mid-air is important.

This leads to two potential techniques to extend current solution mechanisms to harness the complex-valued particle velocity vector $\tilde{u}_q e^{-i\varphi}$ to create solutions that respect the directivity of the waves and their resulting energy transfer.

II. Solution Method for Complex-Valued Pressure

The solution method for complex-valued pressure involves using an acoustic model for pressure. This model can be queried, given a transducer location alongside a control point location, and the resultant phasor at the point in the field determined. This is a complex pressure, $\alpha_{j0q} = \tilde{p}_{j0q}e^{-i\varphi_{j0q}}$, where j corresponds to the index of the sample point in the acoustic field and q the index numbering of the actuated transducer. This enables the creation of an underdetermined linear system:

$$\begin{bmatrix} \alpha_{101} & \cdots & \alpha_{10q} & \cdots & \alpha_{10n} \\ \vdots & \ddots & \vdots & \ddots & \vdots \\ \alpha_{j01} & \cdots & \alpha_{j0q} & \cdots & \alpha_{j0n} \\ \vdots & \ddots & \vdots & \ddots & \vdots \\ \alpha_{m01} & \cdots & \alpha_{m0q} & \cdots & \alpha_{m0n} \end{bmatrix} \begin{bmatrix} x_1 \\ \vdots \\ x_q \\ \vdots \\ x_n \end{bmatrix} = \begin{bmatrix} b_1 \\ \vdots \\ b_q \\ \vdots \\ b_m \end{bmatrix},$$

where b are the intended phasors in the air at locations $1, \ldots, j, \ldots, m$ and x are the transducer activation coefficients from the transducers $1, \ldots, q, \ldots, n$, the initial phase and amplitude required to create the behaviour in the air that is specified by b.

However, as b is complex-valued and contains both phase and amplitude specification, the phase offset can be freely modified. This can be leveraged to find a phase value that opens up the largest possible subspace of amplitudes. This is achieved by finding the principal eigenvector y of the system, $Ly=\lambda y$:

$$L = \begin{bmatrix} A_{c_1} & \cdots & A_{c_j} k_j(\overline{\alpha_{j0}} \cdot \alpha_{10}) & \cdots & A_{c_m} k_m(\overline{\alpha_{m0}} \cdot \alpha_{10}) \\ \vdots & \ddots & \vdots & \ddots & \vdots \\ A_{c_1} k_1(\overline{\alpha_{10}} \cdot \alpha_{j0}) & \cdots & A_{c_j} & \cdots & A_{c_m} k_m(\overline{\alpha_{m0}} \cdot \alpha_{j0}) \\ \vdots & \ddots & \vdots & \ddots & \vdots \\ A_{c_1} k_1(\overline{\alpha_{10}} \cdot \alpha_{m0}) & \cdots & A_{c_j} k_j(\overline{\alpha_{j0}} \cdot \alpha_{m0}) & \cdots & A_{c_m} \end{bmatrix},$$

in which A represents amplitudes desired at each point in the acoustic field and k a per column normalization applied that cancels the dot product to one in each diagonal of the matrix, for each control point in the acoustic field $1, \ldots, j, \ldots, m$. The normalized components of the eigenvector y of this matrix when multiplied with the initial amplitudes A will then correspond to a phasor vector b that promotes reinforcement amongst each of the points of pressure in the field.

Least norm solutions of underdetermined problems can be solved using the form:

$$x_{leastnorm} = A^H (AA^H)^{-1} b.$$

Critical to this solution is the inverse of the matrix $C=AA^H$, which is the first step of solving the system via Cholesky decomposition, and is written:

$$C = \begin{bmatrix} \overline{\alpha_{10}} \cdot \alpha_{10} & \cdots & \overline{\alpha_{j0}} \cdot \alpha_{10} & \cdots & \overline{\alpha_{m0}} \cdot \alpha_{10} \\ \vdots & \ddots & \vdots & \ddots & \vdots \\ \overline{\alpha_{10}} \cdot \alpha_{j0} & \cdots & \overline{\alpha_{j0}} \cdot \alpha_{j0} & \cdots & \overline{\alpha_{m0}} \cdot \alpha_{j0} \\ \vdots & \ddots & \vdots & \ddots & \vdots \\ \overline{\alpha_{10}} \cdot \alpha_{m0} & \cdots & \overline{\alpha_{j0}} \cdot \alpha_{m0} & \cdots & \overline{\alpha_{m0}} \cdot \alpha_{m0} \end{bmatrix},$$

meaning it can help derive the eigensystem matrix L as well. However, also working with the system in the form:

$$w_{focus} = C^{-1} b,$$

yields a very small linear system and subsequent solution size, which can be solved with any technique (QR decomposition, Cholesky factorization, etc.) and kept in this diminutive state until emitted. Neither this C matrix nor this $w_{focus}$ vector has an index in transducers, until computing:

$$x_{leastnorm} = A^H w_{focus}.$$

It is often worth multiplying through by $A^H$ at the last possible moment to convert back into $x_{leastnorm}$ transducer activations that multiply the wave emitted from each transducer, as the transducers can be numerous.

III. Solving for One or More Anisotropic Control Points

Creating the control points in the acoustic field such that they each have a normal vector or direction specified alongside them is one way to incorporate the momentum requirement into a phased array solver. Giving each control point a normal vector effectively means solving for the x, y and z particle velocities and thus components of the wave momentum at the point of interest, rather than solving for pressure at each control point. To achieve this, we expand the linear system equation from before to include three components for each particle velocity in the place of one for pressure defined previously. These three components, then specified as, $\alpha_{x,j0q}$, $\alpha_{y,j0g}$ and $\alpha_{z,j0q}$, are defined as:

$$\alpha_{x,j0q} = \|\tilde{u}_{j0q}\| e^{-i\varphi_{j0q}} \cdot \hat{\Delta}_{x,j0q} \cdot \hat{n}_{x,y},$$
$$\alpha_{y,j0q} = \|\tilde{u}_{j0q}\| e^{-i\varphi_{j0q}} \cdot \hat{\Delta}_{y,j0q} \cdot \hat{n}_{y,j},$$
$$\alpha_{z,j0q} = \|\tilde{u}_{j0q}\| e^{-i\varphi_{j0q}} \cdot \hat{\Delta}_{z,j0q} \cdot \hat{n}_{z,j},$$

in each case, $\hat{\Delta}_{j0q}$ is the vector denoting the direction of the wave propagation from the transducer q at the control point j, and $\hat{n}_j$ is the normal vector direction of the control point j, across whose position the momentum is measured. The core linear system to solve then becomes:

$$\begin{bmatrix} \alpha_{x,101} & \cdots & \alpha_{x,10q} & \cdots & \alpha_{x,10n} \\ \alpha_{y,101} & \cdots & \alpha_{y,10q} & \cdots & \alpha_{y,10n} \\ \alpha_{z,101} & \cdots & \alpha_{z,10q} & \cdots & \alpha_{z,10n} \\ \vdots & \ddots & \vdots & \ddots & \vdots \\ \alpha_{x,j01} & \cdots & \alpha_{x,j0q} & \cdots & \alpha_{x,j0n} \\ \alpha_{y,j01} & \cdots & \alpha_{y,j0q} & \cdots & \alpha_{y,j0n} \\ \alpha_{z,j01} & \cdots & \alpha_{z,j0q} & \cdots & \alpha_{z,j0n} \\ \vdots & \ddots & \vdots & \ddots & \vdots \\ \alpha_{x,m01} & \cdots & \alpha_{x,m0q} & \cdots & \alpha_{x,m0n} \\ \alpha_{y,m01} & \cdots & \alpha_{y,m0q} & \cdots & \alpha_{y,m0n} \\ \alpha_{z,m01} & \cdots & \alpha_{z,m0q} & \cdots & \alpha_{z,m0n} \end{bmatrix} \begin{bmatrix} x_1 \\ \vdots \\ x_q \\ \vdots \\ x_n \end{bmatrix} = \begin{bmatrix} b_{x,1} \\ b_{y,1} \\ b_{z,1} \\ \vdots \\ b_{x,j} \\ b_{y,j} \\ b_{z,j} \\ \vdots \\ b_{x,m} \\ b_{y,m} \\ b_{z,m} \end{bmatrix}$$

which specifies the three components of velocity for particles of the acoustic medium for each control point. However, when using the reduced representation approach to the solution of the system, that is the specification of the C matrix to reduce the amount of effort required, the number of entries of this matrix increases by a factor of nine, making the problem significantly more intensive to compute. For each element of the matrix C previously, $$\overline{\alpha_{k0}} \cdot \alpha_{j0},$$

becomes the submatrix:

$$\begin{bmatrix} \overline{\alpha_{x,k0}} \cdot \alpha_{x,j0} & \overline{\alpha_{y,k0}} \cdot \alpha_{x,j0} & \overline{\alpha_{z,k0}} \cdot \alpha_{x,j0} \\ \overline{\alpha_{x,k0}} \cdot \alpha_{y,j0} & \overline{\alpha_{y,k0}} \cdot \alpha_{y,j0} & \overline{\alpha_{z,k0}} \cdot \alpha_{y,j0} \\ \overline{\alpha_{x,k0}} \cdot \alpha_{z,j0} & \overline{\alpha_{y,k0}} \cdot \alpha_{z,j0} & \overline{\alpha_{z,k0}} \cdot \alpha_{z,j0} \end{bmatrix}.$$

This remains well behaved when using the existing approach in the eigensystem matrix L, which can still be constructed using the same approach, although the user input amplitudes become $A_{x,j}=\tilde{u}_{x,j}$, $A_{y,j}=\tilde{u}_{y,j}$ and $A_{z,j}=\tilde{u}_{z,j}$ or $A_j=\|\tilde{u}_j\|\hat{n}_j$. The cross terms of the eigensystem matrix can be viewed as performing a measurement on one axis at the position of one control point when considering the impact of adding the wave on another axis on a further control point. While the $w_{focus}$ vector now contains three times as many elements, the multiplication by $A^H$ can take the system back to the transducer activation coefficients required to reproduce the desired momentum vectors in the air above the device.

This solution is particularly interesting for the application of mid-air haptic feedback because it opens the possibility to create waves that approach the hand from different angles. This may enable the acoustic waves to be able to induce shear waves in the skin on the boundary, which opens up an entirely new set of sensations that may be created using mid-air haptic techniques, at the expense of the extra required computation.

IV. Solving for the Particle Speed at One or More Control Points in the Acoustic Medium Another technique to achieve the conversion from a solver that targets pressure values to one that is capable of targeting momentum is to create a linear system solver that works entirely with the acoustic particle speed, which (similarly to the original pressure approach) is also complex-valued due to the monochromatic harmonic time. Further, it is scalar. This can be achieved by calculating the direction of greatest particle velocity at a control point and thus the resultant wave direction $\tilde{n}_j$, then multiplying through to make each matrix entry a single complex-valued scalar. As the dot product affects all the sampling directions by a scale factor equally across x, y and z, this can be applied as a post-process to the initial matrix construction. However, the direction of the resulting wave must be known before the solver can function and therefore cannot be influenced by the solver. When applied to the construction of mid-air haptic devices, this approach will be most suitable for small devices where mid-air but relatively close range feedback is best and is an extension to current solution mechanisms.

To achieve this, the acoustic model for each transducer is recast as a problem to determine particle speed in the acoustic medium. The alpha vector thus is redefined to yield a complex-valued particle speed as measured along the direction of greatest motion, $$\alpha_{j0q} = \tilde{u}_{j0q} e^{-i\varphi_{j0q}} \cdot \hat{n}_j,$$

as the system that needs solving for a given control point is of the form $$\left(\sum_{q=1}^{n} \tilde{u}_{j0q} e^{-i(\omega t + \varphi_{j0q})}\right).$$

$\hat{n}_j$. However, unfortunately $\hat{n}_j$ cannot be known a priori, and it is required to construct the linear system matrix:

$$\begin{bmatrix} \alpha_{101} & \cdots & \alpha_{10q} & \cdots & \alpha_{10n} \\ \vdots & \ddots & \vdots & \iddots & \vdots \\ \alpha_{j01} & \cdots & \alpha_{j0q} & \cdots & \alpha_{j0n} \\ \vdots & \iddots & \vdots & \ddots & \vdots \\ \alpha_{m01} & \cdots & \alpha_{m0q} & \cdots & \alpha_{m0n} \end{bmatrix} \begin{bmatrix} x_1 \\ \vdots \\ x_q \\ \vdots \\ x_n \end{bmatrix} = \begin{bmatrix} b_1 \\ \vdots \\ b_j \\ \vdots \\ b_m \end{bmatrix}.$$

Therefore, the acoustic model can be modified to produce the values:

$$\tilde{u}'_{x,j0q} = \|\tilde{u}_{j0q}\| \cdot \hat{\Delta}_{x,j0q},$$

$$\tilde{u}'_{y,j0q} = \|\tilde{u}_{j0q}\| \cdot \hat{\Delta}_{y,j0q},$$

$$\tilde{u}'_{z,j0q} = \|\tilde{u}_{j0q}\| \cdot \hat{\Delta}_{z,j0q},$$

where $$\alpha_{j0q} = \begin{bmatrix} \tilde{u}'_{x,j0q} \\ \tilde{u}'_{y,j0q} \\ \tilde{u}'_{z,j0q} \end{bmatrix} e^{-i\varphi_{j0q}} \cdot \hat{n}_j.$$

These values must then be used to construct the dot products of the C matrix:

$$C = \begin{bmatrix} \overline{\alpha_{10}} \cdot \alpha_{10} & \cdots & \overline{\alpha_{j0}} \cdot \alpha_{10} & \cdots & \overline{\alpha_{m0}} \cdot \alpha_{10} \\ \vdots & \ddots & \vdots & \iddots & \vdots \\ \overline{\alpha_{10}} \cdot \alpha_{j0} & \cdots & \overline{\alpha_{j0}} \cdot \alpha_{j0} & \cdots & \overline{\alpha_{m0}} \cdot \alpha_{j0} \\ \vdots & \iddots & \vdots & \ddots & \vdots \\ \overline{\alpha_{10}} \cdot \alpha_{m0} & \cdots & \overline{\alpha_{j0}} \cdot \alpha_{m0} & \cdots & \overline{\alpha_{m0}} \cdot \alpha_{m0} \end{bmatrix},$$

But there are two potential routes to achieve this. The dot product required is defined by $$\overline{\alpha_{k0}} \cdot \alpha_{j0} = \sum_{q=1}^{n} \left( \begin{bmatrix} \tilde{u}'_{x,k0q} \\ \tilde{u}'_{y,k0q} \\ \tilde{u}'_{z,k0q} \end{bmatrix} e^{i\varphi_{k0q}} \cdot \hat{n}_k \right) \left( \begin{bmatrix} \tilde{u}'_{x,j0q} \\ \tilde{u}'_{y,j0q} \\ \tilde{u}'_{z,j0q} \end{bmatrix} e^{-i\varphi_{j0q}} \cdot \hat{n}_j \right).$$

This can be written as:

$$\overline{\alpha_{k0}} \cdot \alpha_{j0} = \left( \left( \sum_{q=1}^{n} \begin{bmatrix} \tilde{u}'_{x,k0q} \\ \tilde{u}'_{y,k0q} \\ \tilde{u}'_{z,k0q} \end{bmatrix} e^{i\varphi_{k0q}} \otimes \begin{bmatrix} \tilde{u}'_{x,j0q} \\ \tilde{u}'_{y,j0q} \\ \tilde{u}'_{z,j0q} \end{bmatrix} e^{-i\varphi_{j0q}} \right) \cdot \hat{n}_k \right) \cdot \hat{n}_j$$

where $\otimes$ is the dyadic product. This requires nine separate summations to be maintained per matrix element (three for the diagonals) in order to compute the normal vectors afterwards. This is beneficial in that it results in an initial matrix configuration for C that has many similarities to that of the anisotropic control point approach, so therefore may allow for common implementation infrastructure that supports both techniques. However, in many implementations, the alternative of having a two stage modelling system instead may be more desirable than holding these nine separate summation variables. In such a system, the first stage would run a simplified model that computes only velocity amplitude and wave direction, yielding the three velocity directions per control point summations $\Sigma_{q=1}^{n}\tilde{u}_{x,j0q}'$, $\Sigma_{q=1}^{n}\tilde{u}_{y,j0q}'$ and $\Sigma_{q=1}^{n}\tilde{u}_{z,j0q}'$. As this as separated from the phase calculation this may be a simplified model. These summations each give the component of the final strongest amplitude, and so can be used to calculate the direction over which to conduct the summations in the second stage.

In summary:

$$u_j = \begin{bmatrix} \sum_{q=1}^{n} \tilde{u}_{x,j0q}' \\ \sum_{q=1}^{n} \tilde{u}_{y,j0q}' \\ \sum_{q=1}^{n} \tilde{u}_{z,j0q}' \end{bmatrix}, \hat{n}_j = \frac{u_j}{\|u_j\|}.$$

where in the second stage, the model is able to compute:

$$\alpha_{j0q} = \begin{bmatrix} \tilde{u}_{x,j0q}' \\ \tilde{u}_{y,j0q}' \\ \tilde{u}_{z,j0q}' \end{bmatrix} e^{-i\varphi j0q} \cdot \hat{n}_j,$$

inside the transducer model before commencing the other stages of the process. The remaining stages proceed in much the same way as before, only that the directions over which the velocities act are different.

This approach allows the application of mid-air haptic feedback to more directly address the momentum transfer to the hand, rather than the pressure. This leads to improvements in repeatability of sensations and therefore the measurement of perceptual behavior, which is critical to the expansion of mid-air haptics as a commercialized technology.

V. Attached Figures

Figure 17:
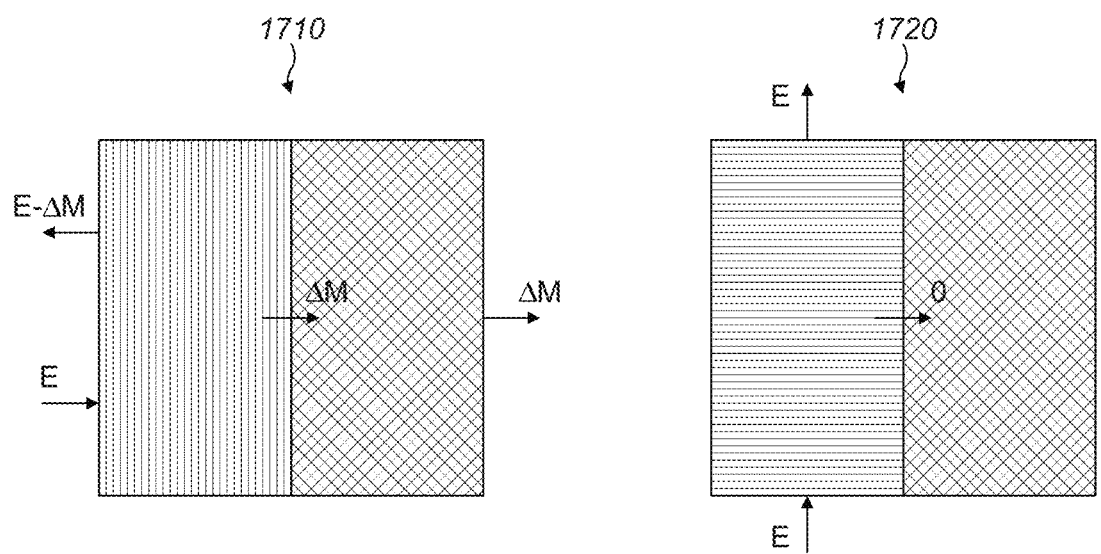
FIG. 17 is a graph of the same wave with the same sound pressure level, but scenarios in which the effect of the vector components may give rise to a maximal haptic effect, but also no haptic effect.

FIG. 17 shows the same wave with the same sound pressure level (SPL) yields different effects at a surface dependent on the angle of incidence. On the left side 1710 a wave (left) travelling parallel to a surface (right), impacts with some energy E, reflects and leaves with slightly less energy as a result of momentum exchange. On the right side 1720 a wave that travels perpendicularly to the same surface does not reflect and exchange energy, therefore leaving with the same quantity of energy. As a result, it is impossible for a haptic effect to be imparted.

Figure 18:
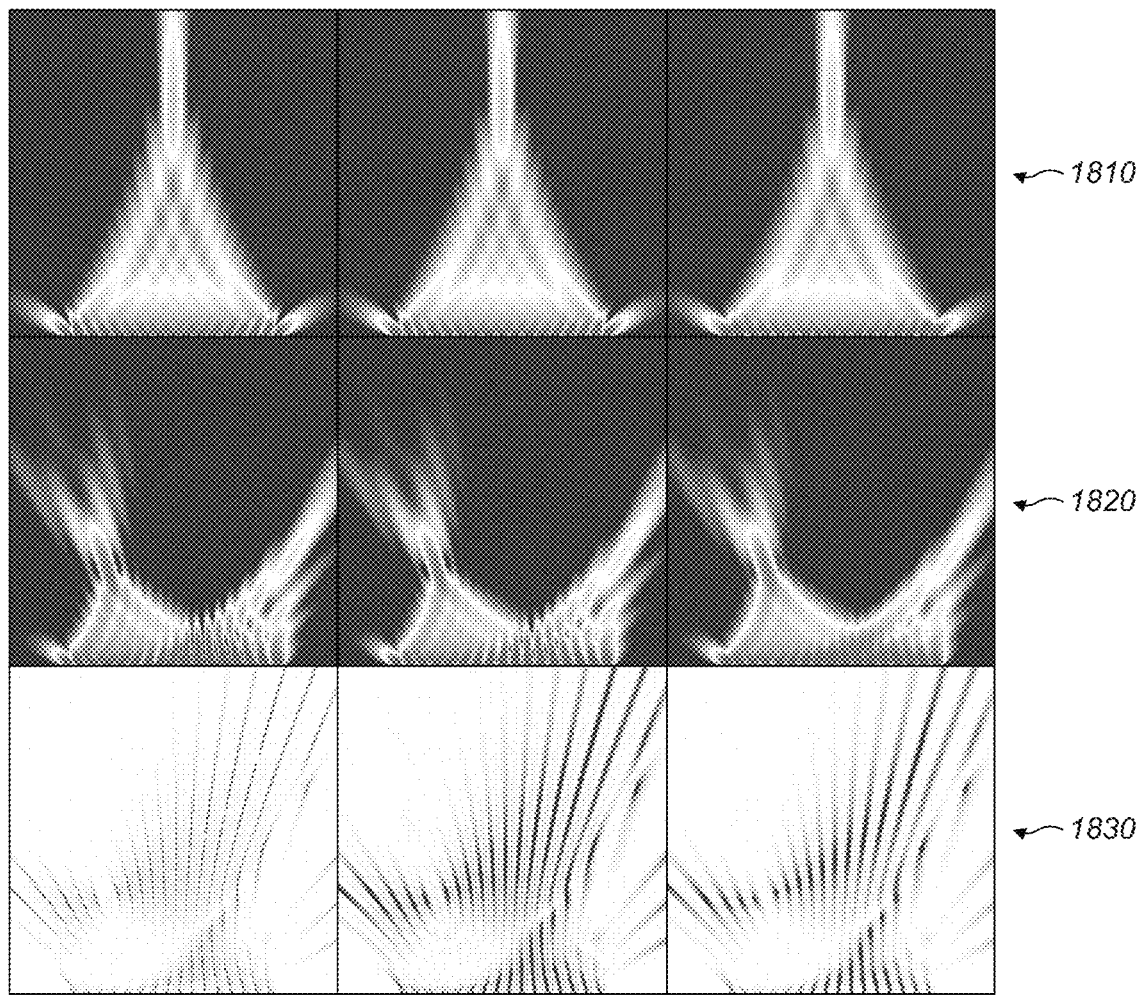
FIG. 18 are simulations of measurements of an acoustic field generated by a phased array in dB SPL, dB SIL and dB SVL.

In FIG. 18, shown in the top two rows 1810, 1820 are simulations of measurements of an acoustic field generated by a phased array in dB SPL, dB SIL and dB SVL respectively of two different focusses created by the time of flight approach, where light gray is +10 dB, white is 0 dB and dark gray is −10 db. The bottom row 1830 (dB SPL dB SIL), (dB SPL dB SVL) and (dB SIL dB SVL) respectively with the same color scheme reveals the differences between each measurement method. The SVL field measurement simulation, as it is based on the velocity of the particles of the medium, can allow waves to cancel further due to additional vector component cancellation. As a result, dB SVL is always less than dB SIL which is less than dB SPL, although they are similar distances apart in the logarithmic dB space due to the multiplication of their respective components and effective geometric mean of the SIL measurement.

4. EIGENSYSTEM SOLUTIONS FOR QUADRATIC PROBLEMS IN MID-AIR HAPTIC SYSTEMS

I. Rayleigh-Ritz Theorem for Quadratic Optimization

Suppose a matrix M is a square positive semi-definite Hermitian d×d matrix. Since the matrix is square and Hermitian, each eigenvalue must be real. Since it is positive semi-definite these eigenvalues must be positive as $x^H/Mx \geq 0$.

The eigenvalues may then be organized as:

$$\lambda_{min} \leq \lambda_1 \leq \lambda_2 \leq \ldots \leq \lambda_d \leq \lambda_{max}.$$

The $\lambda_{min}$ and $\lambda_{max}$ of the matrix can then be shown to be solutions to the optimization problems:

$$\lambda_{min} = \min_{x \neq o} \frac{x^H M x}{x^H x} = \min_{|x|^2 = 1},$$

and $$\lambda_{max} = \max_{x \neq o} \frac{x^H M x}{x^H x} = \max_{|x|^2 = 1}.$$

This is the Rayleigh-Ritz theorem. It follows that the x vector from each of these can be found as the corresponding eigenvector to the eigenvalue found.

II. Quadratic Optimization for Phased Array Systems

When considering phased array systems, it is useful to define as $x^H$ as:

$$x^H = [\alpha_1 e^{-i\varphi_1} \ldots \alpha_q e^{-i\varphi_q} \ldots \alpha_n e^{-i\varphi_n}],$$

with n the number of monochromatic sound sources, so that this vector solution can be used to drive the array of source transducers. Then define the matrix M as an n×n Hermitian matrix, such that when x is a unit norm ($|x|^2=1$) eigenvector:

$$x^H M x = \alpha_1 e^{-i\varphi_1} M_{1,1} \alpha_1 e^{+i\varphi_1} + \alpha_1 e^{-i\varphi_1} M_{1,2} \alpha_1 e^{+i\varphi_2} + \\ \ldots \alpha_n e^{-i\varphi_n} M_{n,n-1} \alpha_{n-1} e^{+i\varphi_{n-1}} + \alpha_n e^{-i\varphi_n} M_{n,n} \alpha_n e^{+i\varphi_n} = \lambda_{max}.$$

This then represents the form of the optimization. All that is left to do is to fill in the matrix M with the particular pure quadratic (as the matrix M is required to be symmetric or Hermitian) objective function that is required.

There are five potentially useful purely quadratic forms for the objective function that produce Hermitian matrices M and so can be maximized using existing eigenvector solvers to obtain a solved field that could be used to drive mid-air ultrasonic haptics:

1. Maximum pressure optimization (total SPL): a. Maximizes $p\bar{p}$, proportional to the square of the pressure; b. This is the objective function used generally for driving phased array systems.

2. Maximum particle velocity optimization (total SVL): a. Maximizes u Ft proportional to the square of the particle velocity; b. This takes into account the directionality of the waves, as this is necessary to obtain consistent haptic perception.

3. Maximum particle velocity optimization, but along a given direction (usable SVL): a. Maximizes $(u \cdot \hat{n})\overline{(u \cdot \hat{n})}$ proportional to the square of particle velocity along a given direction; b. This takes into account both the directionality of the wave and the impact normal with the (skin) surface n̂.

4. Maximum acoustic intensity (energy flux density) optimization (total SIL): a. Maximizes $$\sqrt{\frac{1}{4}(\overline{pu} \cdot u\overline{p})}$$

proportional to acoustic intensity; b. This takes into account the directionality of the waves, as this is necessary to obtain consistent haptic perception.

5. Maximum acoustic intensity (energy flux density) optimization along a given direction (usable SIL): a. Maximizes $$\frac{1}{4}(\overline{pu \cdot \hat{n}} + \overline{p}u \cdot \hat{n})$$

proportional to acoustic intensity along a given direction; b. This takes into account both the directionality of the wave and the impact normal with the (skin) surface n̂.

III. Optimize to Maximize Pressure

The quadratic form optimizer capable of maximizing pressure at each control point would be modeling the quantity:

$$\left(\sum_{q=1}^{n} \tilde{p}_{jq}\alpha_q e^{-i(\omega t + \varphi_{j0q} + \varphi_q)}\right)\left(\sum_{r=1}^{n} \tilde{p}_{jr}\alpha_r e^{+i(\omega t + \varphi_{j0r} + \varphi_r)}\right),$$

at each control point j, yielding the summation of the objective function $$\sum_{j=1}^{m} w_j \left(\sum_{q=1}^{n} \tilde{p}_{jq}\alpha_q e^{-i(\varphi_{j0q} + \varphi_q)}\right)\left(\sum_{r=1}^{n} \tilde{p}_{jr}\alpha_r e^{+i(\varphi_{j0r} + \varphi_r)}\right),$$

which makes each element of the n×n matrix whose dominant eigenvector is to be solved for:

$$M_{q,r} = \sum_{j=1}^{m} w_j \tilde{p}_{jq}\tilde{p}_{jr} e^{-i\varphi_{j0q}} e^{+i\varphi_{j0r}},$$

where $\tilde{p}_{jq}$ is the positive and real amplitude of the wave pressure and $e^{-i\varphi_{j0q}}$ the complex phase offset, on the wave travelling from transducer q at control point j from the initial emission. The weight $w_j$ is used to reweight the quadratic p $\overline{p}$ term to provide relative amplitude control among the control points. The global amplitude scaling is provided by the unit norm condition on the input power, $x^H x = 1$. This, combined with the quadratic reweighting factor and a control loop can be used to address individual pressure amplitudes precisely.

IV. Optimize to Maximize Particle Velocity

The quadratic form optimizer capable of maximizing particle velocity would be modelling the quantity:

$$\left(\sum_{q=1}^{n} \tilde{u}_{xjq}\alpha_q e^{-i(\omega t + \varphi_{j0q} + \varphi_q)}\right)\left(\sum_{r=1}^{n} \tilde{u}_{xjr}\alpha_r e^{+i(\omega t + \varphi_{j0r} + \varphi_r)}\right) +$$

$$\left(\sum_{q=1}^{n} \tilde{u}_{yjq}\alpha_q e^{-i(\omega t + \varphi_{j0q} + \varphi_q)}\right)\left(\sum_{r=1}^{n} \tilde{u}_{yjr}\alpha_r e^{+i(\omega t + \varphi_{j0r} + \varphi_r)}\right) +$$

$$\left(\sum_{q=1}^{n} \tilde{u}_{zjq}\alpha_q e^{-i(\omega t + \varphi_{j0q} + \varphi_q)}\right)\left(\sum_{r=1}^{n} \tilde{u}_{zjr}\alpha_r e^{+i(\omega t + \varphi_{j0r} + \varphi_r)}\right)$$

for each control point j. This would yield the summation of the objective function as:

$$\sum_{j=1}^{m} \left[\left(\sum_{q=1}^{n} \tilde{u}_{xjq}\alpha_q e^{-i(\varphi_{j0q} + \varphi_q)}\right)\left(\sum_{r=1}^{n} \tilde{u}_{xjr}\alpha_r e^{+i(\varphi_{j0r} + \varphi_r)}\right) + \right.$$

$$\left(\sum_{q=1}^{n} \tilde{u}_{yjq}\alpha_q e^{-i(\varphi_{j0q} + \varphi_q)}\right)\left(\sum_{r=1}^{n} \tilde{u}_{yjr}\alpha_r e^{+i(\varphi_{j0r} + \varphi_r)}\right) +$$

$$\left.\left(\sum_{q=1}^{n} \tilde{u}_{zjq}\alpha_q e^{-i(\varphi_{j0q} + \varphi_q)}\right)\left(\sum_{r=1}^{n} \tilde{u}_{zjr}\alpha_r e^{+i(\varphi_{j0r} + \varphi_r)}\right)\right],$$

which makes each element of the n×n matrix whose dominant eigenvector is to be solved for:

$$M_{q,r} = \sum_{j=1}^{m} w_j (\tilde{u}_{xjq}\tilde{u}_{xjr} + \tilde{u}_{yjq}\tilde{u}_{yjr} + \tilde{u}_{zjq}\tilde{u}_{zjr}) e^{-i\varphi_{j0q}} e^{+i\varphi_{j0r}},$$

where $u_{xjq}$ is the x direction part of the induced particle velocity amplitude (which is real and positive) and $e^{-i\varphi_{j0q}}$ the complex phase offset, on the wave travelling from transducer q at control point j from the initial emission. The weight $w_j$ is used to reweight the quadratic u·ū term to provide relative particle velocity amplitude control among the control points. The global amplitude scaling is provided by the unit norm condition on the input power, $x^H x = 1$. This, combined with the quadratic reweighting factor and a control loop can be used to address individual velocity amplitudes precisely.

V. Optimize to Maximize Particle Velocity in a Set of Given Directions

The quadratic form optimizer capable of maximizing particle velocity in a set of given directions would be modeling the quantity:

$$\left(\sum_{q=1}^{n} \tilde{u}_{xjq}\hat{n}_{xj}\alpha_q e^{-i(\omega t + \varphi_{j0q} + \varphi_q)}\right)\left(\sum_{r=1}^{n} \tilde{u}_{xjr}\hat{n}_{xj}\alpha_r e^{+i(\omega t + \varphi_{j0r} + \varphi_r)}\right) +$$

$$\left(\sum_{q=1}^{n} \tilde{u}_{yjq}\hat{n}_{yj}\alpha_q e^{-i(\omega t + \varphi_{j0q} + \varphi_q)}\right)\left(\sum_{r=1}^{n} \tilde{u}_{yjr}\hat{n}_{yj}\alpha_r e^{+i(\omega t + \varphi_{j0r} + \varphi_r)}\right) +$$

$$\left(\sum_{q=1}^{n} \tilde{u}_{zjq}\hat{n}_{zj}\alpha_q e^{-i(\omega t + \varphi_{j0q} + \varphi_q)}\right)\left(\sum_{r=1}^{n} \tilde{u}_{zjr}\hat{n}_{zj}\alpha_r e^{+i(\omega t + \varphi_{j0r} + \varphi_r)}\right)$$

for each control point j. This would yield the summation of the objective function as:

$$\sum_{j=1}^{m}\left(\left(\sum_{q=1}^{n}\tilde{u}_{xjq}\hat{n}_{xj}\alpha_q e^{-i(\varphi_{j0q}+\varphi_q)}\right)\left(\sum_{r=1}^{n}\tilde{u}_{xjr}\hat{n}_{xj}\alpha_r e^{+i(\varphi_{j0r}+\varphi_r)}\right)+\right.$$
$$\left(\sum_{q=1}^{n}\tilde{u}_{yjq}\hat{n}_{yj}\alpha_q e^{-i(\varphi_{j0q}+\varphi_q)}\right)\left(\sum_{r=1}^{n}\tilde{u}_{yjr}\hat{n}_{yj}\alpha_r e^{+i(\varphi_{j0r}+\varphi_r)}\right)+$$
$$\left.\left(\sum_{q=1}^{n}\tilde{u}_{zjq}\hat{n}_{zj}\alpha_q e^{-i(\varphi_{j0q}+\varphi_q)}\right)\left(\sum_{r=1}^{n}\tilde{u}_{zjr}\hat{n}_{zj}\alpha_r e^{+i(\varphi_{j0r}+\varphi_r)}\right)\right),$$

which makes each element of the n×n matrix whose dominant eigenvector is to be solved for:

$$M_{q,r}=\sum_{j=1}^{m}w_j\left(\tilde{u}_{xjq}\tilde{u}_{xjr}\hat{n}_{xj}^2+\tilde{u}_{yjq}\tilde{u}_{yjr}\hat{n}_{yj}^2+\tilde{u}_{zjq}\tilde{u}_{zjr}\hat{n}_{zj}^2\right)e^{-i\varphi_{j0q}}e^{+i\varphi_{j0r}},$$

where $\tilde{u}_{xjq}$ is the x direction part of the induced particle velocity amplitude (which is real and positive) and $e^{-i\varphi_{j0q}}$ the complex phase offset, on the wave travelling from transducer q at control point j from the initial emission. The weight $w_j$ is used to reweight the quadratic $(u\cdot\hat{n})\overline{(u\cdot\hat{n})}$ term to provide relative amplitude control among the control points. The global amplitude scaling is provided by the unit norm condition on the input power, $x^H x=1$. This, combined with the quadratic reweighting factor and a control loop can be used to address individual amplitudes precisely.

VI. Active Acoustic Intensity

Active acoustic intensity $I_a$ can be defined using the pressure p and particle velocity vector u of the acoustic medium. For an acoustic wave, this can be described as:

$$I_a=\frac{1}{2}\Re(p\cdot\overline{u}),$$

where the active intensity is a purely real vector quantity. In the near field of a wave source, the reactive field dominates instead $I_r=\frac{1}{2}\Im(p\cdot\overline{u})$. However, in the far field, so beyond one or two wavelengths, $I_r\to 0$. For this reason, only $I_a$ is considered and assumed to be guaranteed real. Considering a monochromatic plane wave source, where:

$p=\tilde{p}e^{-i(\omega t+\varphi)}$, $u=\tilde{u}e^{-i(\omega t+\varphi)}$, we have:

$$I_a=\frac{1}{2}\left(\tilde{p}e^{-i(\omega t+\varphi)}\cdot\overline{\tilde{u}e^{-i(\omega t+\varphi)}}\right),$$

where $\tilde{p}$ is the pressure amplitude, and $\tilde{u}$ is the particle velocity amplitude in each direction.

The sound intensity and thus energy flux transmitted by the wave along a given axis is also of interest so the dot product to measure the scalar contribution is formed:

$$I_a\cdot\hat{n}=\frac{1}{2}\left(\tilde{p}e^{-i(\omega t+\varphi)}\cdot\overline{\tilde{u}e^{-i(\omega t+\varphi)}}\cdot\hat{n}\right)$$

Due to the form of the acoustic wave equations:

$$\frac{\partial^2 p}{\partial t^2}-c_0^2\nabla^2 p=0,$$

$$\frac{\partial^2 u}{\partial t^2}-c_0^2\nabla^2 u=0,$$

the superposition principle must hold for both pressure and particle velocity vectors. Assuming n acoustic sources and approximating each as a plane wave at the point of interest, then yields the equations:

$$I_a=\frac{1}{2}\left(\sum_{q=1}^{n}\tilde{p}_q e^{-i(\omega t+\varphi_q)}\cdot\overline{\sum_{r=1}^{n}\tilde{u}_r e^{-i(\omega t+\varphi_r)}}\right).$$

$$I_a\cdot\hat{n}=\frac{1}{2}\left(\sum_{q=1}^{n}\tilde{p}_q e^{-i(\omega t+\varphi_q)}\cdot\overline{\sum_{r=1}^{n}\tilde{u}_r e^{-i(\omega t+\varphi_r)}}\cdot\hat{n}\right).$$

It is known that in a regime in question $\Im(p\cdot\overline{u})\to 0$, and p and $\overline{u}$ are in phase, then it is known that the placement of the conjugation does not matter and it is possible to reverse order of the conjugations to conjugate pressure instead of particle velocity (this can be verified by expanding the above equations and using commutativity to reverse the order of the complex exponentials in each term). From inference, this can be written in a way that generates a Hermitian matrix M:

$$I_a=\frac{1}{4}\left(\sum_{q=1}^{n}\tilde{p}_q e^{-i(\omega t+\varphi_q)}\cdot\overline{\sum_{r=1}^{n}\tilde{u}_r e^{-i(\omega t+\varphi_r)}}+\sum_{q=1}^{n}\tilde{u}_q e^{-i(\omega t+\varphi_q)}\cdot\overline{\sum_{r=1}^{n}\tilde{p}_r e^{-i(\omega t+\varphi_r)}}\right),$$

$$I_a\cdot\hat{n}=$$
$$\frac{1}{4}\left(\sum_{q=1}^{n}\tilde{p}_q e^{-i(\omega t+\varphi_q)}\cdot\overline{\sum_{r=1}^{n}\tilde{u}_r e^{-i(\omega t+\varphi_r)}}\cdot\hat{n}+\sum_{q=1}^{n}\tilde{u}_q e^{-i(\omega t+\varphi_q)}\cdot\hat{n}\cdot\overline{\sum_{r=1}^{n}\tilde{p}_r e^{-i(\omega t+\varphi_r)}}\right).$$

VII. Optimize to Maximize Acoustic Intensity

The first quantity that generates a scalar value is:

$$\frac{1}{4}\sum_{q=1}^{n}\tilde{p}_{jq}\alpha_q e^{-i(\omega t+\varphi_{j0q}+\varphi_q)}\cdot\sum_{r=1}^{n}[\tilde{u}_{xjr},\tilde{u}_{yjr},\tilde{u}_{zjr}]\alpha_r$$
$$e^{+i(\omega t+\varphi_{j0r}+\varphi_r)}\cdot\sum_{s=1}^{n}[\tilde{u}_{xjs},\tilde{u}_{yjs},\tilde{u}_{zjs}]\alpha_s e^{-i(\omega t+\varphi_{j0s}+\varphi_s)}\cdot\sum_{v=1}^{n}\tilde{p}_{jv}\alpha_v e^{+i(\omega t+\varphi_{j0v}+\varphi_v)}$$

but then assuming it is in the far field, this may also be written as:

$$\frac{1}{4}\sum_{q=1}^{n}\tilde{p}_{jq}\alpha_q e^{-i(\omega t+\varphi_{j0q}+\varphi_q)}\cdot\sum_{r=1}^{n}\tilde{p}_{jr}\cdot[\hat{a}_{xjr},\hat{a}_{yjr},\hat{a}_{zjr}]\alpha_r e^{+i(\omega t+\varphi_{j0r}+\varphi_r)}\cdot$$
$$\sum_{s=1}^{n}\tilde{p}_{js}\cdot[\hat{a}_{xjs},\hat{a}_{yjs},\hat{a}_{zjs}]\alpha_s e^{-i(\omega t+\varphi_{j0s}+\varphi_s)}\cdot\sum_{v=1}^{n}\tilde{p}_{jv}\alpha_v e^{+i(\omega t+\varphi_{j0v}+\varphi_v)}$$

this is a fourth power of the pressure summation, but due to the structure of the complex exponentials two of these are the same and so can be removed through a square root.

The quadratic form optimizer capable of maximizing acoustic intensity would therefore be modelling the quantity:

$$\frac{1}{2}\sum_{q=1}^{n}\sum_{r=1}^{n}\tilde{p}_{jq}\alpha_q e^{-i(\omega t + \varphi_{j0q} + \varphi_q)}\tilde{p}_{jr}\alpha_r e^{+i(\omega t + \varphi_{j0r} + \varphi_r)}$$

$$\sqrt{[\hat{d}_{xjq}, \hat{d}_{yjq}, \hat{d}_{zjq}] \cdot [\hat{d}_{xjr}, \hat{d}_{yjr}, \hat{d}_{zjr}]}$$

for each control point j. This would yield the summation of the objective function as:

$$\frac{1}{2}\sum_{j=1}^{m}\left(\left(\sum_{q=1}^{n}\tilde{p}_{jq}\alpha_q e^{-i(\varphi_{j0q}+\varphi_q)}\right)\right.$$

$$\left.\left(\sum_{r=1}^{n}\tilde{p}_{jr}\alpha_r e^{+i(\varphi_{j0r}+\varphi_r)}\right)\left(\sum_{q=1}^{n}\sum_{r=1}^{n}\sqrt{[\hat{d}_{xjq}, \hat{d}_{yjq}, \hat{d}_{zjq}] \cdot [\hat{d}_{xjr}, \hat{d}_{yjr}, \hat{d}_{zjr}]}\right)\right),$$

which makes each element of the n×n matrix whose dominant eigenvector is to be solved for:

$$M_{q,r} = \frac{1}{2}\sum_{j=1}^{m}w_j\left(\tilde{p}_{jq}\tilde{p}_{jr}\sqrt{[\hat{d}_{xjq}, \hat{d}_{yjq}, \hat{d}_{zjq}] \cdot [\hat{d}_{xjr}, \hat{d}_{yjr}, \hat{d}_{zjr}]}\right)e^{-i\varphi_{j0q}}e^{+i\varphi_{j0r}}$$

where $\hat{d}_{xjq}$ is the x direction part of the wavefront normal vector, $\tilde{p}_{jg}$ is the positive and real amplitude of the wave pressure and $e^{-i\varphi_{j0q}}$ the complex phase offset, on the wave travelling from transducer q at control point j from the initial emission. The weight $w_j$ is used to reweight the quadratic term which really remains the square root of the function involving a fourth power of pressure, $$\sqrt{\frac{1}{4}(p\overline{u}\cdot u\overline{p})}$$

to provide relative particle velocity amplitude control among the control points. The global amplitude scaling is provided by the unit norm condition on the input power, $x^H x=1$. This, combined with the quadratic reweighting factor and a control loop can be used to address individual velocity amplitudes precisely.

VIII. Optimize to Maximize Acoustic Intensity in a Set of Given Directions

The quadratic form optimizer capable of maximizing acoustic intensity along a given direction would be modelling the quantity:

$$\frac{1}{4}\sum_{q=1}^{n}\tilde{p}_{jq}\alpha_q e^{-i(\omega t + \varphi_{j0q} + \varphi_q)} \cdot \sum_{r=1}^{n}(\tilde{u}_{xjr}\hat{n}_{xj} + \tilde{u}_{yjr}\hat{n}_{yj} + \tilde{u}_{zjr}\hat{n}_{zj})\alpha_r e^{+i(\omega t + \varphi_{j0r} + \varphi_r)} +$$

$$\frac{1}{4}\sum_{q=1}^{n}(\tilde{u}_{xjq}\hat{n}_{xj} + \tilde{u}_{yjq}\hat{n}_{yj} + \tilde{u}_{zjq}\hat{n}_{zj})\alpha_q e^{-i(\omega t + \varphi_{j0q} + \varphi_q)} \cdot \sum_{r=1}^{n}\tilde{p}_{jr}\alpha_r e^{+i(\omega t + \varphi_{j0r} + \varphi_r)}$$

but then assuming it is in the far field, this may also be written as:

$$\frac{1}{4}\sum_{q=1}^{n}\tilde{p}_{jq}\alpha_q$$

$$e^{-i(\omega t + \varphi_{j0q} + \varphi_q)} \cdot \sum_{r=1}^{n}\tilde{p}_{jr}[\hat{d}_{xjr}, \hat{d}_{yjr}, \hat{d}_{zjr}] \cdot [\hat{n}_{xj}, \hat{n}_{yj}, \hat{n}_{zj}]\alpha_r e^{+i(\omega t + \varphi_{j0r} + \varphi_r)} + \frac{1}{4}$$

$$\sum_{q=1}^{n}\tilde{p}_{jq}[\hat{d}_{xjq}, \hat{d}_{yjq}, \hat{d}_{zjq}] \cdot [\hat{n}_{xj}, \hat{n}_{yj}, \hat{n}_{zj}]\alpha_q e^{-i(\omega t + \varphi_{j0r} + \varphi_r)} \cdot \sum_{r=1}^{n}\tilde{p}_{jr}\alpha_r e^{+i(\omega t + \varphi_{j0q} + \varphi_r)}$$

for each control point j. This would yield the summation of the objective function as:

$$\frac{1}{4}\sum_{j=1}^{m}\left(\left(\sum_{q=1}^{n}\tilde{p}_{jq}\alpha_q e^{-i(\varphi_{j0q}+\varphi_q)}\right)\right.$$

$$\left(\sum_{r=1}^{n}\tilde{p}_{jr}[\hat{d}_{xjr}, \hat{d}_{yjr}, \hat{d}_{zjr}] \cdot [\hat{n}_{xj}, \hat{n}_{yj}, \hat{n}_{zj}]\alpha_r e^{+i(\varphi_{j0r}+\varphi_r)}\right) +$$

$$\left.\left(\sum_{q=1}^{n}\tilde{p}_{jq}[\hat{d}_{xjq}, \hat{d}_{yjq}, \hat{d}_{zjq}] \cdot [\hat{n}_{xj}, \hat{n}_{yj}, \hat{n}_{zj}]\alpha_q e^{-i(\varphi_{j0q}+\varphi_q)}\right)\left(\sum_{r=1}^{n}\tilde{p}_{jr}\alpha_r e^{+i(\varphi_{j0r}+\varphi_r)}\right)\right),$$

which makes each element of the n×n matrix whose dominant eigenvector is to be solved for:

$$M_{q,r} =$$

$$\frac{1}{4}\sum_{j=1}^{m}w_j\left(\tilde{p}_{jq}\tilde{p}_{jr}(\hat{d}_{xjq}\hat{n}_{xj} + \hat{d}_{yjq}\hat{n}_{yj} + \hat{d}_{zjq}\hat{n}_{zj} + \hat{d}_{xjr}\hat{n}_{xj} + \hat{d}_{yjr}\hat{n}_{yj} + \hat{d}_{zjr}\hat{n}_{zj})\right)e^{-i\varphi_{j0q}}$$

$$e^{+i\varphi_{j0r}},$$

where $\tilde{u}_{xjq}$ is the x direction part of the induced particle velocity amplitude (which is real and positive), $\tilde{p}_{jg}$ is the positive and real amplitude of the wave pressure and $e^{-i\varphi_{j0q}}$ the complex phase offset, on the wave travelling from transducer q at control point j from the initial emission. The weight $w_j$ is used to reweight the quadratic $\frac{1}{4}(p\overline{u}\cdot\hat{n}+\overline{p}u\cdot\hat{n})$ term to provide relative particle velocity amplitude control among the control points. The global amplitude scaling is provided by the unit norm condition on the input power, $x^H x=1$. This, combined with the quadratic reweighting factor and a control loop can be used to address individual velocity amplitudes precisely.

IX. Finding the Weighting Factors

The Rayleigh-Ritz theorem shows that any of the above matrices can be maximized by finding the dominant eigenvector and allowing the power to increase up to the physical limitations of the transducers. This can be achieved through the power iteration. By constructing the matrix M while individually defining each of the sum of control points separately, when multiplying through by the vector x the evaluation of the objective function can be performed as an additional side effect. This can be used to find appropriate values for the weights $w_j$ such that they allow the maximization to find amplitudes that when scaled are appropriate to the solution of the system.

As the power iteration describes:

$$x_a = \frac{Mx_{a-1}}{\|Mx_{a-1}\|},$$

where:

$$x = \lim_{a \to \infty} x_a.$$

We can use the power iteration to determine the objective function at each control point.
Defining:

$$M_{q,r} = \sum_{j=1}^{m} M_{q,r,j},$$

and:

$$M = \sum_{j=1}^{m} M_j.$$

On each iteration it can instead compute:

$$x_{a,j} = M_j x_{a-1})$$

so, the objective function at each control point can be evaluated as:

$$o_j(x_{a-1}) = x_{a-1}^H x_{a,j}.$$

Finally, as before $x_a$ can be computed:

$$x_a = \frac{\sum_{j=1}^{m} x_{a,j}}{\left\|\sum_{j=1}^{m} x_{a,j}\right\|},$$

where the final eigenvector solution is as above. However, calculating it in this way allows $o_j(x_{a-1})$ to yield an intermediate result for the control point j. To fix the level at which this is representative of the desired control point output, the average objective function value is taken in order to allow the set of values $o_j(x_{a-1})$ to be directly compared to the objective values given by the user. In this case, the weighting factors can be updated for the next iteration using any derivative-free method meant for the optimization of expensive functions, such as the Nelder-Mead algorithm for example.

After some number of iterations of the power method and coupled derivative-free optimization, the intermediate result $x_a$ should be used to drive the transducers. This will therefore allow the system to track the desired values of the objective functions through time, while allowing for some error. The advantage of this system is that it is a very simple way to drive a transducer array. The largest disadvantage is that many calculations are required, but the calculations are effectively only complex multiplications which with sufficient hardware are straightforwardly implemented.

X. Attached Figure

Figure 19:
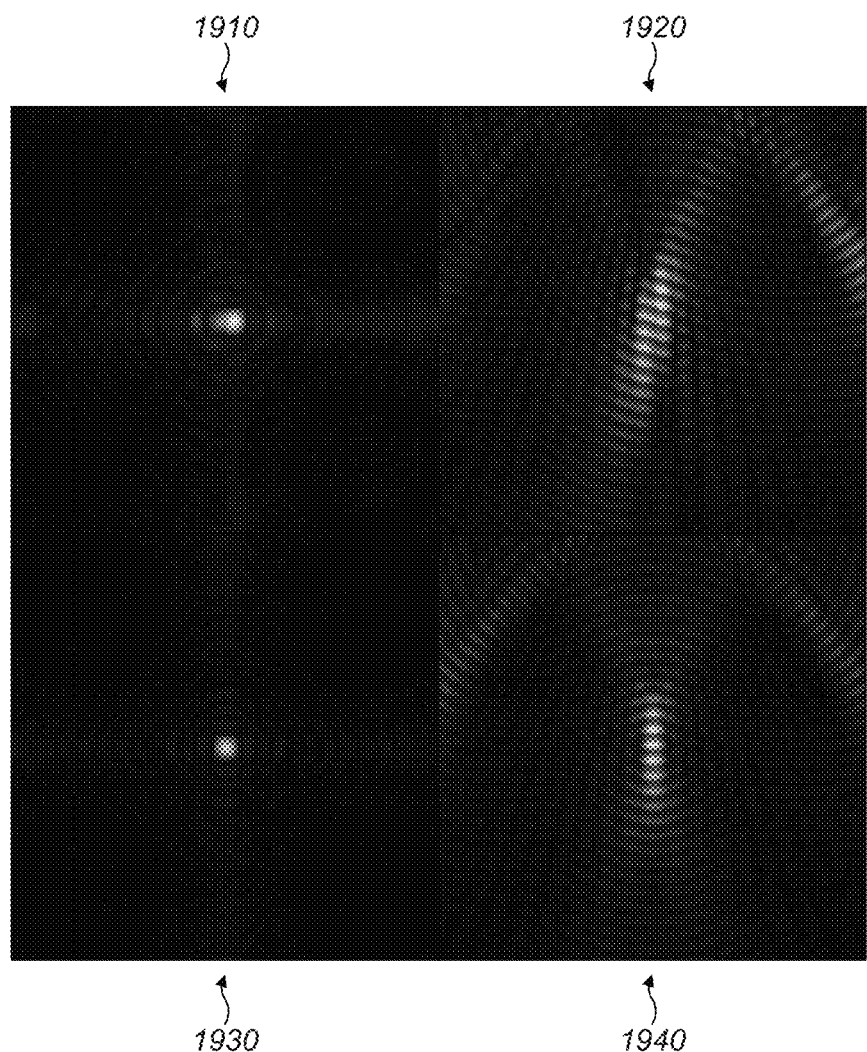
FIG. 19 shows control point plots created by solving the quadratic problems.

Shown in FIG. 19 are: Top left 1910: Control point created by solving the quadratic particle velocity problem with a non-perpendicular vector, shown as a cut through the x-y plane. Top right 1920: The same control point displayed as a cut through the x-z plane. Bottom left 1930: For comparison, a control point created by solving the quadratic pressure problem, shown as a cut through the x-y plane. Bottom right 1940: A cut through the solution to the pressure problem across the x-z plane.

5. CONTROL REGIONS FOR PHASED ARRAYS SPECIFIED THROUGH QUADRATIC PROBLEMS

This disclosure describes a method to automatically generate basis functions using user supplied design parameters. These are input to an efficient optimization over a quadratic function in the space of a given transducer basis set in an online manner. This gives the user a design space, accessible through an online optimization that may generate a variety of different effects. Using a linear operator, termed a 'quadratic control region' as it is a control region for a quadratic problem, a matrix may be constructed by evaluating the dyadic product over the transducer effects. The dominant eigenvector of this matrix may be chosen as the best solution from a set of orthonormal solutions which are identically the eigenvectors of this matrix. The optimization produces as output the transducer activation coefficients the raw complex values needed to drive the individual transducer elements to recreate the acoustic field or phenomena with the desired properties.

These raw complex values may then be used to further comprise the basis functions of a later linear system whose solution enables the user to produce all the desired effects simultaneously whilst reweighting the output power available to each.

I. Linear Control Region

A linear control region, which is defined as an operator that performs an integral with an linear acoustic quantity, such as pressure, with a complex valued weighting function, w(x,y,z):

$$f_p(x, y, z) = \iiint_\Omega \overline{w(x, y, z)} \cdot p(x, y, z)\, dx\, dy\, dz$$

may be used to evaluate an acoustic field. It should be noted that the complex conjugate is used to maximize function evaluation when w(x, y, z) is paired with similar phase distributions in the acoustic quantity. Any approximation to this integral (such as sampling) can be used or indeed this may be used to approximate any linear operator over the field of acoustic pressure. A further integral may be constructed to optimize a control region using a vector particle velocity, given it is also linear, wherein:

$$f_v(x, y, z) = \iiint_\Omega \overline{w(x, y, z)} \cdot u(x, y, z)\, dx\, dy\, dz,$$

with u the particle velocity of the medium, and w a three-dimensional vector field in which each dimension is complex-valued, which serves as a weighting function with the same purpose as above. In this way, different patterns of acoustic quantities may be evaluated in a linear fashion, maximizing a particular phase of the result when phases align with the 'template' created by the scalar or vector function in w.

It also should be noted that w(x, y, z) may be largely zero (or comprised of zero vectors) to create a single evaluation of multiple seemingly disjoint regions. Any integral approximation (such as sampling) can be used as this formulation can extend to any linear operator over the field of a linear acoustic quantity.

A phased array may be described by a series of complex valued coefficients that controls each transducer. Driving an array of acoustic transducers at a fixed frequency with such an input x vector to maximise an acoustic quantity encoded in a matrix M may be expressed as a linear algebra problem, so that the intention is to:

maximize $x^H M x$
subject to $x^H x = 1$,
and $x \in \mathbb{C}^n$.

This may be solved by taking the dominant eigenvector of the matrix M, as the statement of the problem is also the definition of an eigenvector, here x. Building the matrix M may be achieved by first considering the linear acoustic quantities emitted by each transducer as a basis function in the global space of the acoustic quantity in question. This is a way to achieve the maximization of pressure and other acoustic quantities at a single point, described by an absolute position in x, y and z. However, using the described control region integral, the q(x, y, z) that governs the acoustic quantities emitted into the field of each individual transducing element may be exchanged for $f(x, y, z)$, yielding the column vector:

$$f = \begin{bmatrix} f_1(x, y, z) \\ \vdots \\ f_n(x, y, z) \end{bmatrix},$$

By invoking linearity, the complex activation values driving each of the transducers may be multiplied leading to the vector:

$$m = \begin{bmatrix} x_1 \cdot f_1(x, y, z) \\ \vdots \\ x_n \cdot f_n(x, y, z) \end{bmatrix},$$

where n is the number of transducers. Given that this m is the result of a linear operator operating on a linear field, it may be Hermitian transposed and multiplied by itself to generate a quadratic form. Finally, $$m^H m = x^H M x = x^H f f^H x.$$

By modifying the weighting function w(x, y, z) and solving for the eigenvectors of the matrix M, a variety of different beams, surfaces and other acoustic phenomenon may be created and maximized, producing optimally actuated regions in the acoustic field.

The null space generation technique discussed previously ("Eigensystem solutions for quadratic problems in mid-air haptic systems") may also be used to extend this method to describe acoustic levitation, as well as allowing for null steering and the formation of mid-air texture by introducing null points into the field at positions to describe structure. It should be noted that this process increases the rank of the matrix, so simplification is not possible should this be used.

Equally, multiple optimizations may be carried out by adding together M matrices for a number of control regions. This may also include matrices that represent control points. This generates a matrix that has increased rank, so some simplification methods are not possible in the case that this is used.

By considering the result and reweighting each of the points in an iterative manner, the system may be modified so as to converge to the required geometric configuration of an acoustic quantity. This may be generally needed when the amplitudes are not consistent in the output.

This may be achieved by summing the acoustic quantities produced and reweighting the system to in the next iteration progress more closely to the result. For instance, the iterative reweighting for any sub-split volume of integral or single point of pressure becomes:

$$w_{t+1,i}(x, y, z) := w_{t,i}(x, y, z) \cdot \frac{p_{r,i}(x, y, z)}{p_{t,i}(x, y, z)},$$

where t+1 refers to the next coarse iteration of the technique, t the current iteration, $p_r$ the desired pressure (which may be complex) and the denominator the total pressure obtained by the current iteration. The fraction may be rendered as only real magnitudes in order to only affect the amplitudes of the resulting region and not the phases.

A Bessel beam may be created by expressing a weighting function, w(x, y, z), in the direction of beam travel and creating unit pressure while modifying the phase angle forward as the beam moves forward. This may be sampled with point samples, so long as the angle traversed by each subsequent point is small enough to sufficiently sample the phase along the beam axis.

The sampling of the phase must importantly have more than two phase samples for every $2\pi$ in angle that it moves. This is because if the increment along the path is $\pi$, the direction of the wave travel is undecidable. This also means in the majority of cases, the phase must increment forward such that it completes a $2\pi$ radian rotation for every wavelength of the monochromatic frequency distance it covers. This is an approximation to a path integral of the form described in the control region definition.

Figure 20:
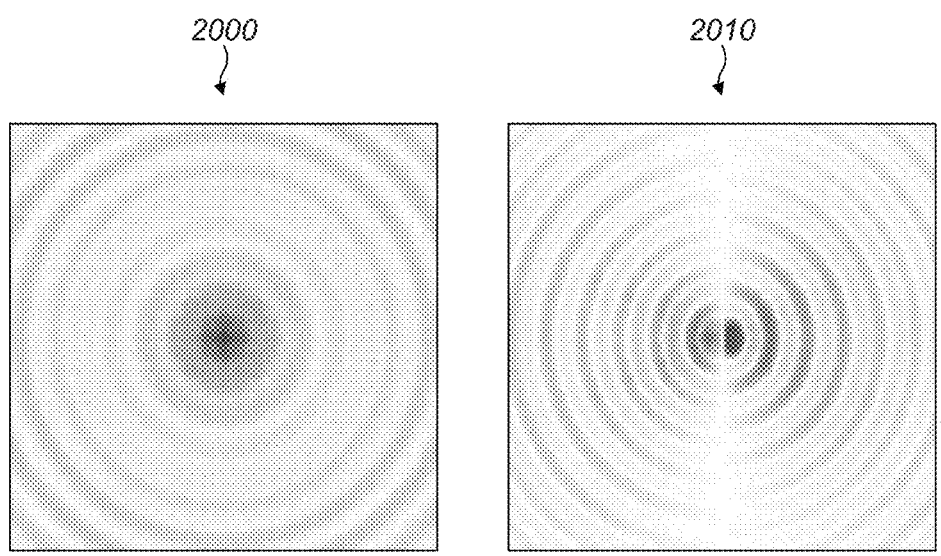
FIG. 20 shows cuts through an acoustic field at the edge of the near field region parallel to the flat rectilinear transducer array.
Figure 21:
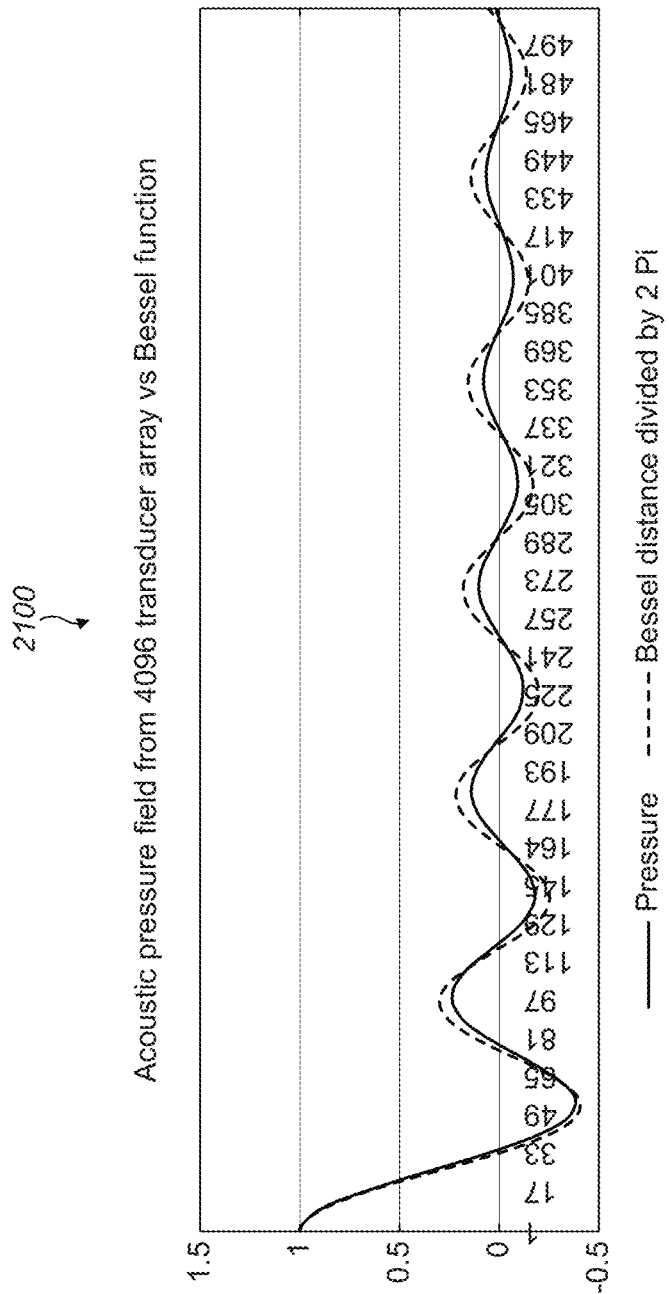
FIG. 21 shows a graph of a Bessel function.

The transducers, as a result of maximizing the integral written in this way, will in the case of a simple beam progressively defined in a straight line moving away from the array, generate an optimal Bessel-like beam due to its theoretical ability to generate optimal pressure in this configuration. Shown in FIG. 20 are cuts through the field at the edge of the near field region parallel to the flat rectilinear transducer array, revealing the structure of the complex-valued transducer activation coefficients. A simple progressive phase beam results in a Bessel function approximation (left 2000) and an under-sampled helical beam results in a Bessel-like function with dipole behavior (right 2010), where the dipole creates two structures that activate in a manner wherein each opposes the other in phase. The beam may not be an exact Bessel beam due to the effects of limited transducer resolution, finite array size and other physical considerations which the optimization will need to work around, but may perform more effectively than a simple evaluation of a Bessel beam function due to the optimization taking into account the physical limitations of a real transducer array. On a large array, it follows the Bessel function closely, FIG. 21 shows a graph 2100 of a Bessel function plotted alongside pressure when considered radially from the center of the array in FIG. 20.

A further property of this system is that transducers in any position and orientation, with any generated monochromatic field function may be used. This is a significant advantage in Bessel beam generation over a sampling method, which would by definition function only in the planar array case.

Figure 22:
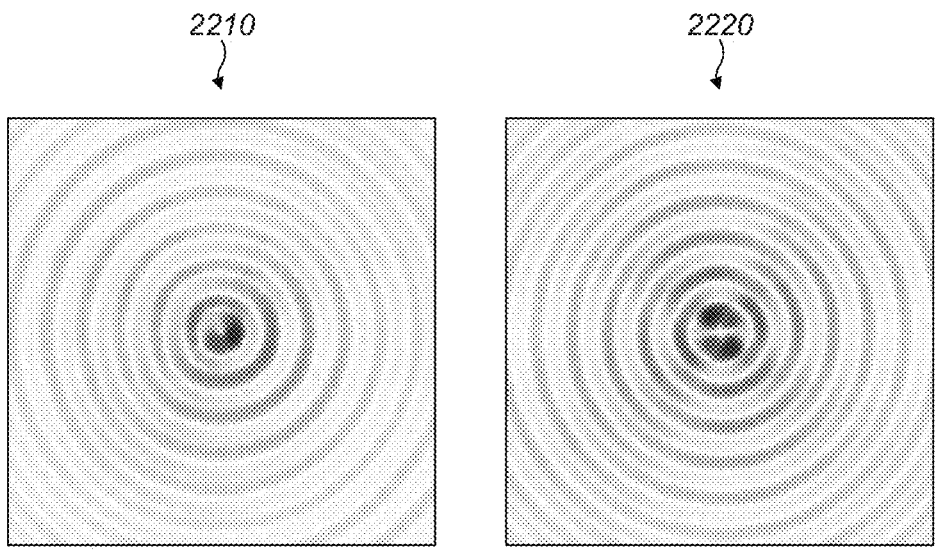
FIGS. 22-23 show cross-sections of approximations to high order Bessel and Mathieu beams.

By creating multiple out-of-phase paths, phase shifts and phase singularities may be created implicitly by winding helical waves around a path. This path may also be curved, yielding a large degree of configurability, while using the simple quadratic optimization embedded in the eigensystem approach. This is achieved by inducing rotations in the beam through the definition of separate phase windings in many parallel beam lines that are closer than the beam width but differ in phase between each other. Then, by setting the nearby phases to cancel each other in the central line of the beam, a high-order Bessel beam may be formed, as shown in FIG. 22. In FIG. 22 more than two samples of the progressive phases around a circle (thus, phases in a helical arrangement) causes the formation of Bessel function with angular momentum as seen on the left 2210. By using more than $2\pi$ radians for specifying the phases around the helix, higher order Bessel beams may be generated such as the $4\pi$ beam on the right 2220.

Figure 23:
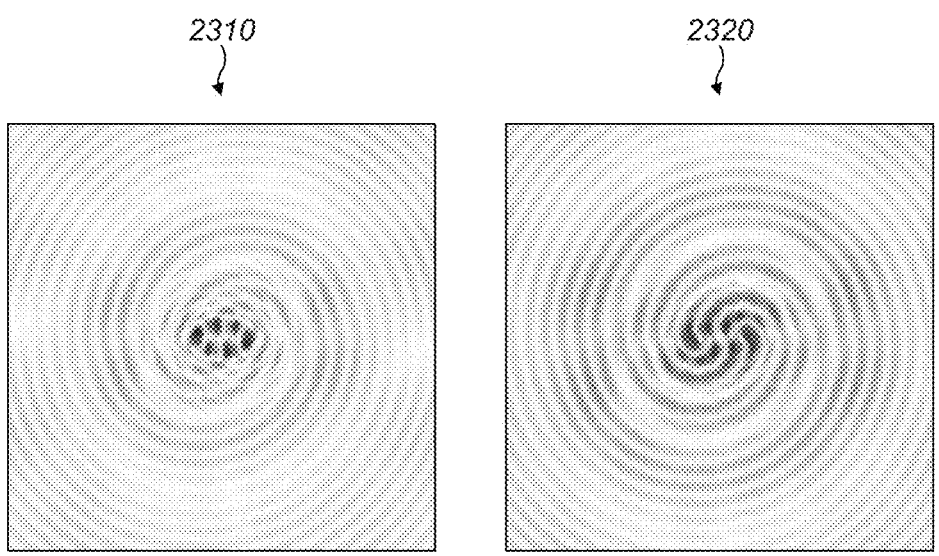

These lines of phase may be sampled using points or any other integral approximation as before, as these are examples of how disjoint regions may be defined as a single regional optimization, wherein each may be added to the optimization region by setting the weighting function to non-zero only in the volume to be optimized. High-order Mathieu-type elliptic helical beams may be created by introducing incremental phase beams incremental in phase and spaced around an ellipse. As shown in FIG. 23, elliptical helical beams that have similar properties to high-order Bessel beams, such as Matheiu-type beams, may be created by parametrizing the circumference of an ellipse in phase. Determining a proportion of the $2n\pi$ radians and allocating a phase angle proportional to the ellipse chord circumference generates the appropriate configuration for the optimisation of the beam. The left image 2310 shows a high order Bessel reshaped into an ellipse, nearing a Matheiu beam. The right image 2320 shows an approximate Matheiu beam with cross-linked helical structures beginning to form in the central region. Both are based on a phase circle of $12\pi$ radians, creating a helical wavefront.

The Bessel family of beams that are created in this manner may be modified to produce more exotic beams that exist in more restrictive forms in the literature. By creating arbitrary paths in the field traversed by physically plausible phase functions that move forward in a way appropriate to the traversal of waves, a variety of results may be reproduced, but due to the optimization implied by the eigensystem in a form that is more general and lower in initial bandwidth cost than before, as the beam need only be expressed by the integral.

Figure 24:
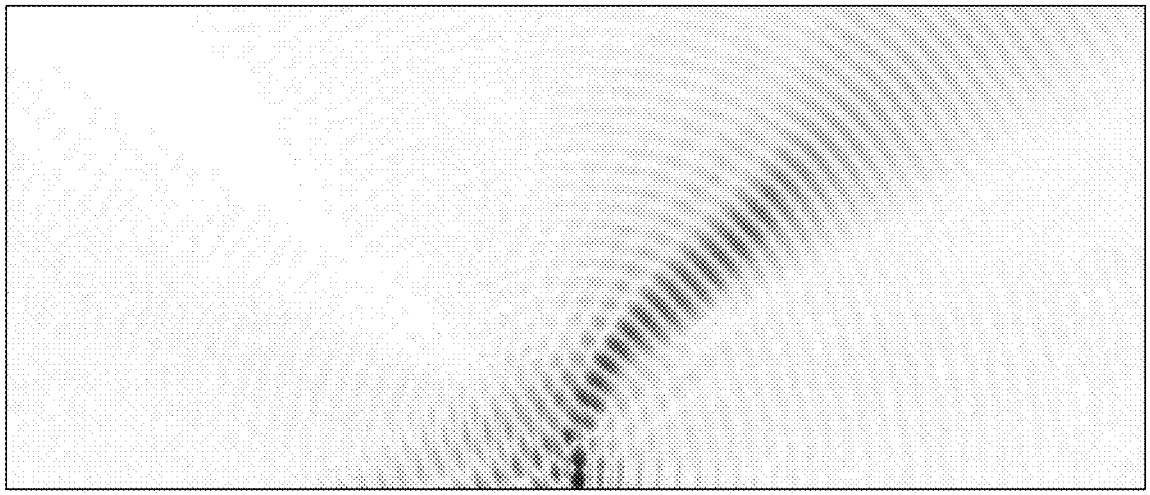
FIGS. 24-26 show a bending beam, a bottle beam and a partial section of a bottle beam.

Taking a curved path and moving the phase forward may produce a curved beam, generally used to maneuver beams around obstacles produced by a 45° circle segment followed by a path that pushes the beam formed out to infinity. Shown in FIG. 24 is an image 2400 of a bending beam, formed from a phase function that follows a 45 degree segment of a circle connected to a continuation along a line, using the coarse iteration method to equalize acoustic pressures along the beam. The transducer array is situated along the lower edge of the image.

Figure 25:
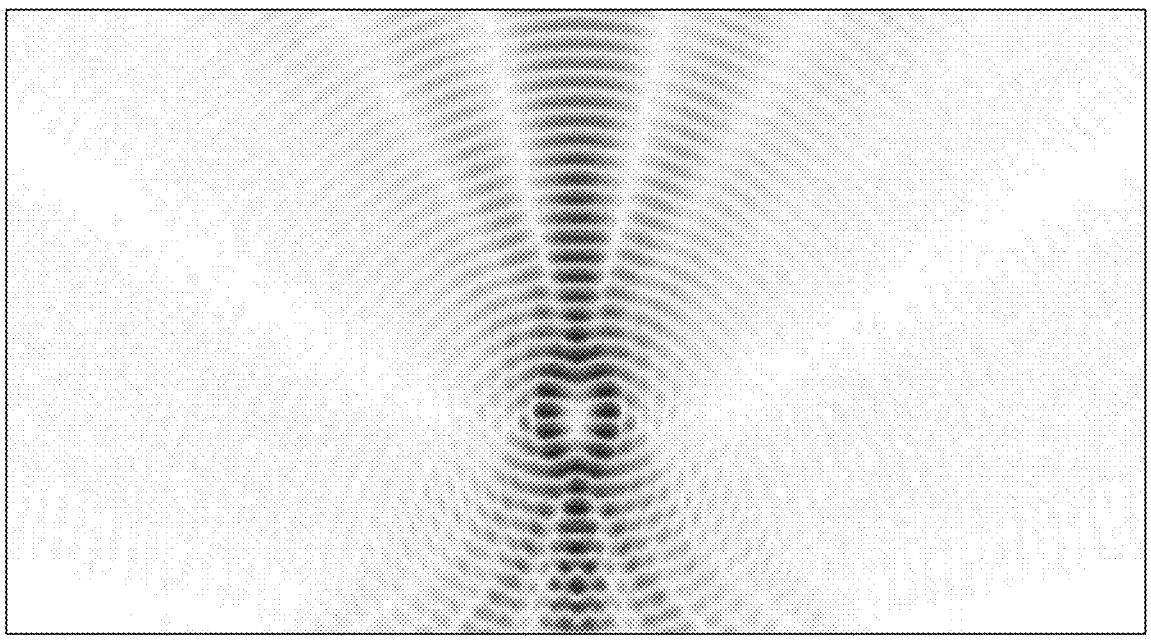
Figure 26:
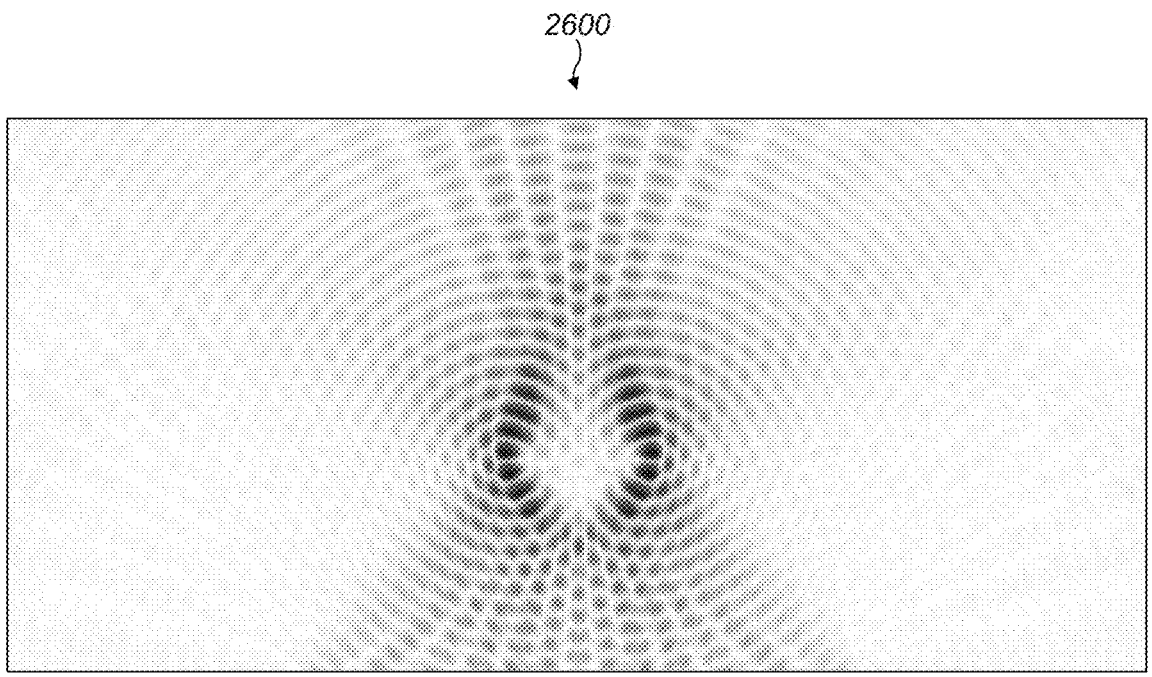

A further approach involving multiple phase paths may create a "bottle beam", a beam with a portion cut from the center, which can facilitate the levitation of large objects. This has been generated in FIG. 25 which shows an image 2500 of twinning two Gaussian curves along which the phase has been made to follow. The bottle beam produced by creating phase functions follow Gaussian curves using the coarse iteration method to equalize acoustic pressures along the beam. The transducer array is situated along the lower edge of the image. The dotted nature of the lower region suggests that the phase velocity input to the optimization is too slow, and that the beam may be improved by using a faster phase velocity for the initial section. Portions of curves may also be used, such as in FIG. 26, since if the object is sufficiently rigid, only some sections of the space need to be made high acoustic pressure regions. FIG. 26 shows an image 2600 of an incomplete bottle beam formed form portions of a circle defined in progressive phase that may be used to levitate even larger objects by optimizing the region of high acoustic pressure in a non-uniform manner. It is not necessary to spread the forces exerted on the large object evenly if the object or matter to be levitated is assumed to have enough cohesion to not flow, extrude or leak through the low acoustic pressure regions.

Figure 27:
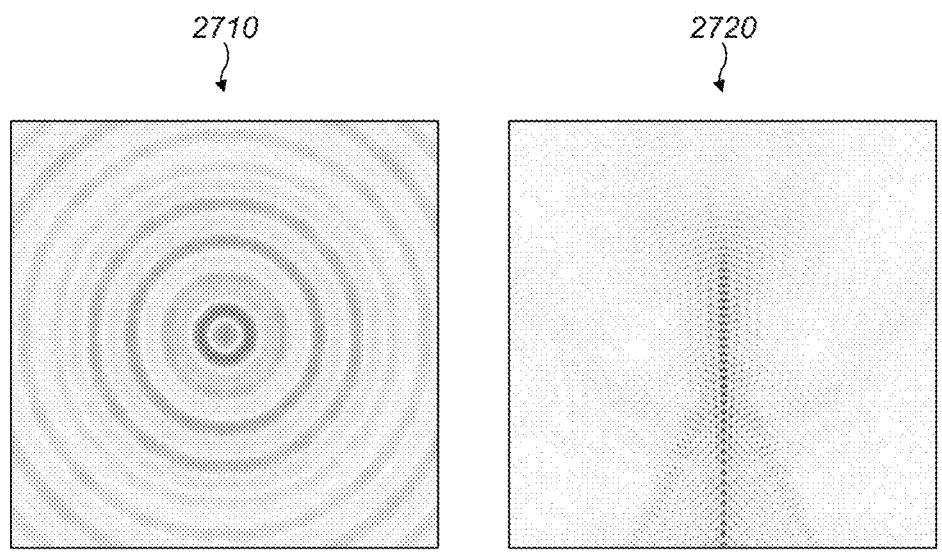
FIG. 27-29 show a beam with increased wavelength, a snaking beam and a helical beam.
Figure 28:
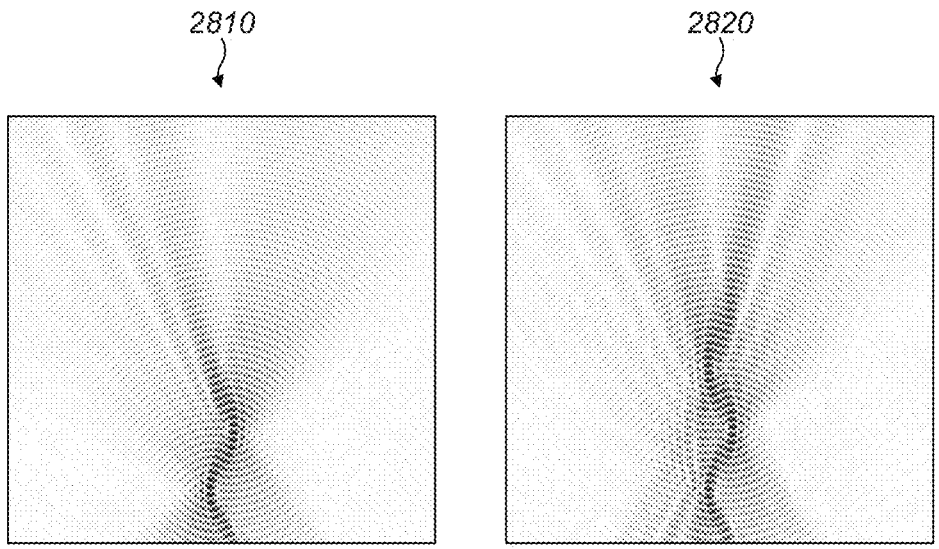
Figure 29:
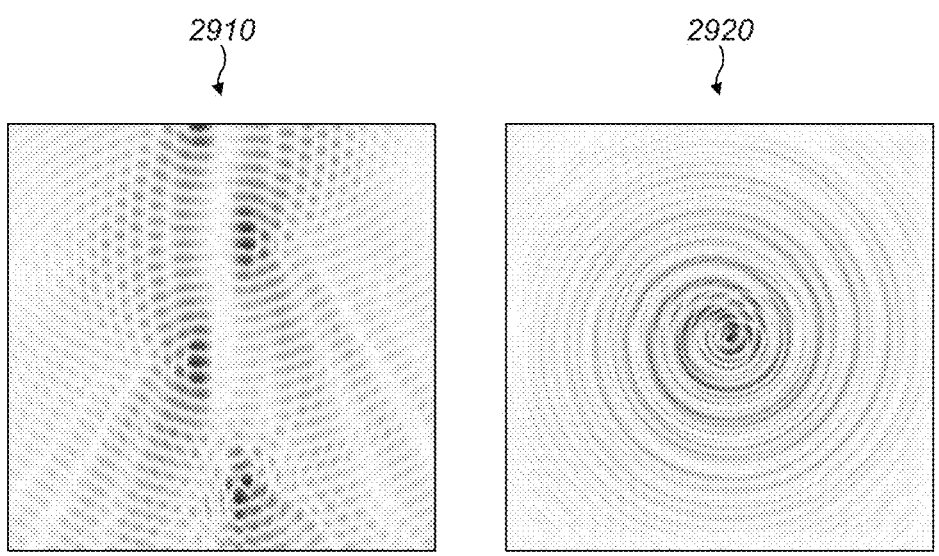

A Bessel-like beam may be created by moving a path forward faster than the phase velocity. In this way, a beam will be optimized for with a faster phase velocity than usual, creating a beam that appears to have longer wavelength and by virtue of the phase velocity travel faster than the speed of sound, as shown in FIG. 27. Shown in FIG. 27 is an image 2710 of a wave front that travels faster than the speed of sound, which may be created by implementing a phase path that moves through angle in a way that paradoxically generates a longer wavelength with the same frequency. The implicit optimization infers that the main beam is composed of intersecting beams, giving rise to the specified increase in phase velocity. This can be seen from the image 2720 on the right, where the wavelength is manipulated to be approximately 40% longer at the same frequency for the initial section of the beam. A snaking beam may be constructed by sampling progressive phases along a sine curve. Shown in FIG. 28 are examples 2810 wherein a short section of the sine curve is defined, followed by 2820 of a longer two-dimensional snaking beam constructed from progressive phases of pressure following a sine curve above a phased array. These show that the extension of the snaking sine wave beam by simply adding further sections of progressive phase causes the beam to be naturally extended as far as required (and allowed by the physical arrangement of transducers). By creating the snaking beam in all three dimensions to make a helically snaking beam, a beam can be produced that may be used in a manner similar to an Archimedes screw system to apply forces, potentially in the direction perpendicular or opposite to the emission of the waves, to solid objects in the field that are much larger than a wavelength. This gives a different mechanism whereby a beam may be used to levitate objects. FIG. 29 shows a left image 2910 detailing a section in the x-z plane and a right image 2920 showing a section of the beam in the x-y plane. Using this technique of following a path in a circle winding in the x and y directions, but which is also progressive in z, a true helical formation can be created. This could be used to levitate and apply forces in a tractor beam-like manner to objects much larger than a wavelength.

If the eigensystem matrix is defined by a single control region, then the matrix is of rank 1 and formed by the dyadic product of the complex-valued vector m with itself only, defining the matrix as $f^H f$. In this specific case, the single eigenvector of the system is known immediately and is $f$, meaning $f = x$. By evaluating the objective function in this case, the objective function specifies itself the coefficients of the complex-valued transducer activations needed. This is defined by simply evaluating the control region function for each transducer, which becomes the activation coefficient.

As before, due to the quadratic form, evaluating the effectiveness through a reweighting on each iteration may also be pursued. This is achieved by evaluating the pressure at each point or the integral of pressure over each sub-region and dividing through by the desired pressure, generating a new function value to update $w_{t,i}(x, y, z)$, the weight for the sub-region i. The single eigenvector which is also $f$ may then be re-evaluated, generating an equivalent approach to the repeated iteration over the eigensystem from before, but at a greatly reduced computational cost.

To achieve this with the particle velocity of the medium, we can use a test of the particle velocity, which amounts to changing the direction until a maximum is reached:

$$w_{t+1,i}(x, y, z) := w_{t,x,i}(x, y, z) \cdot \frac{u_{r,x,i}(x, y, z)}{u_{t,x,i}(x, y, z)},$$

although the pressure may also be monitored using the previous technique to create a hybrid method. This hybrid technique involves specifying the weighting function and update in pressure as before, but with a control region that is effectively:

$$f_{v'}(x, y, z) = \int\int\int_\Omega \overline{w(x, y, z)} \cdot v(x, y, z) \cdot u(x, y, z) \, dx \, dy \, dz,$$

yielding a scalar but changeable and complex-valued $w(x, y, z)$ paired with a unchanging weighting normal vector v and particle velocity u. This approach can optimise to find a satisfactory pressure but without changing the direction of the wave that is sought. This is shown, alongside specific corrections described in the next section, in FIG. 28.

II. Wavefront Filtering for Directional Control Points and Regions

A further technique necessary to the creation of directional output is to discard transducer data, set it to zero, in the case where the transducer output wavefront S and the normal vector or particle velocity vector u are opposite, so satisfy:

$$\begin{bmatrix} \hat{\delta}_{x,i}(x, y, z) \\ \hat{\delta}_{y,i}(x, y, z) \\ \hat{\delta}_{z,i}(x, y, z) \end{bmatrix} \cdot \begin{bmatrix} u_{x,i}(x, y, z) \\ u_{y,i}(x, y, z) \\ u_{z,i}(x, y, z) \end{bmatrix} < 0,$$

for the point of the region under consideration.

Figure 30:
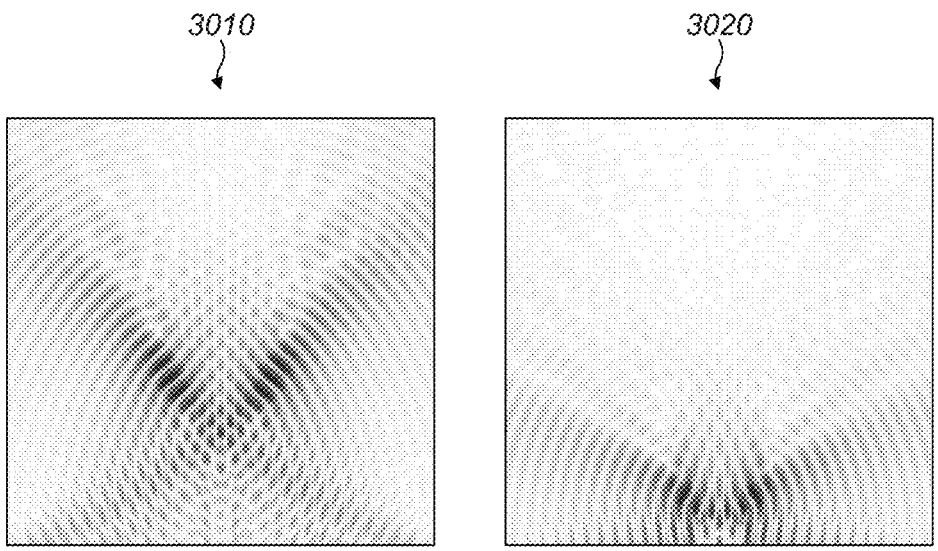
FIG. 30-31 shows the effect of removing transducers that contribute waves from the direction that is opposite to that of the desired wave.

FIG. 30 shows a left image 3010 of two velocity vector samples defined further from the transducer array and a right image 3020 of two velocity vector samples defined close to the array that have had transducers whose wavefronts are in the direction opposite to the defined control direction removed. Using the velocity weighting function specified in these two disjoint regions makes up a single region in each case, wherein the region is optimizing for directional vectors representing particle velocity of the medium in two separate points.

Note that in trying to find the maximum amount of velocity in the x direction does not necessarily mean that the resulting particle velocity direction will be in entirely in x.

Figure 31:
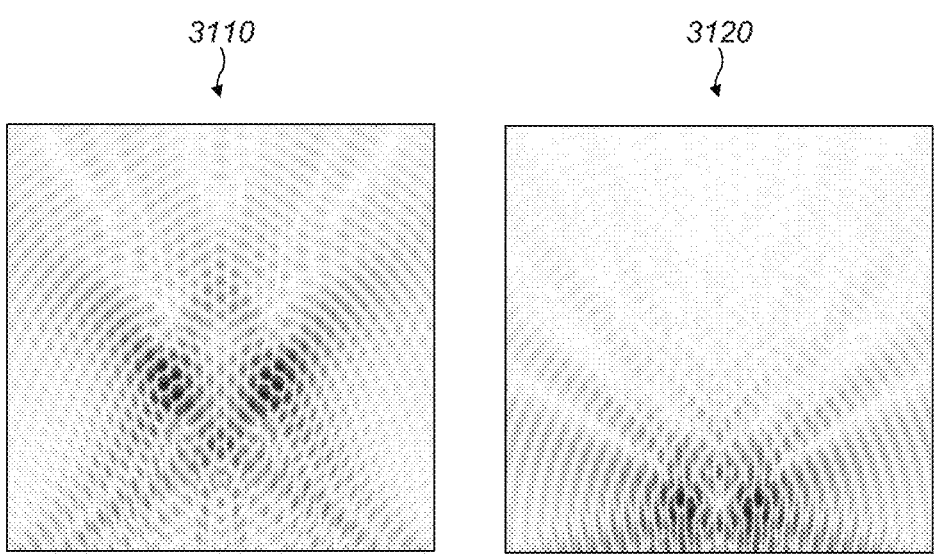

Whereas FIG. 30 shows the result of filtering out conflicting transducers that offer wavefronts that are opposed to the desired direction, shown in FIG. 31 is a left image 3110 and a right image 3120 that are the result in which the transducer wavefront directions have not been filtered using the wavefront criterion. Conflicting transducers are in the case of FIG. 31 free to interfere, whose pathology is apparent in the form of a standing wave structure horizontally. This is because the wavefront direction conveys directional information that is missing from the particle velocity, the particle velocity does not yield information pertaining to which direction the wave originated from, enabling unwanted interference.

This is also important for the simple case of a control point with normal and not just a control region. The case of a control point is effectively a simplified control region wherein it is approximated with a single point sample of particle velocity and no weighting factor. In either case, not filtering out 'unhelpful' transducers yields a similar result with elements of the effects of a 'standing wave' phenomenon. This is because a particle velocity vector with complex components cannot determine the difference between waves travelling in different directions: a wave travelling left-to-right with phase 0 is in this model for a point sample mathematically identical to a right-to-left travelling wave with phase $\pi$. As a result, if this is not dealt with correctly in the generation of the control point or region basis, the optimization will attempt to use both, generating a solution with standing wave components that do not contribute meaningfully, creating extra nulls, regions with no field, that are unwanted. This is an important point, as control points entered as basis functions into linear optimizations, eigensystems or even simple formula without this filtering step will exhibit these artefacts.

These techniques described may be integrated into a device to create an acoustic phased array system that is capable of producing arbitrarily configured regions and beams by iterating a single eigensystem as defined here or in the simple case creating a single point or region. In the single point or region case an optimization may be applied to generate a simple formula which shows that the amplitudes and phases needed to drive the transducer elements are the amplitudes and phases expressed by evaluating the point or region. The iteration of the global method and repeated application through time may be changed and modified in a time dependent manner to produce a variety of haptic effects. This may be applied to both the desired field and the transducer coefficients derived, as they are functionally related.

III. Potential claims

1. A method of, on a monochromatic acoustic field:
    Evaluating a distribution of acoustic pressure to a single value by integrating the product of the acoustic pressure field function with a weighting function, either of which function may be complex-valued and are derived from physical transducer properties.
    Applying zero or more null points to be added to the null space of the matrix.
    Using this as the objective function to be maximised in an optimisation, where the optimisation result takes the form of the eigenvectors of a matrix formed from cross-multiplied terms of the objective function for each transducer.
    Summing one or more such matrices to generate an eigensystem where one or more eigenvectors produces the specified field.

2. A method of, on a monochromatic acoustic field:
   Evaluating a distribution of acoustic particle velocity to a single vector value by integrating the dot product of a real three-dimensional weighting vector field with a particle velocity field with a weighting function, where either of which functions may have complex-valued components and are derived from physical transducer properties.
   Applying zero or more null points to be added to the null space of the matrix.
   Using this as the objective function to be maximised in an optimisation, where the optimisation result takes the form of the eigenvectors of a matrix formed from cross-multiplied terms of the objective function for each transducer.
   Summing one or more such matrices to generate an eigensystem where one or more eigenvectors produces the specified field.
3. A method of, on a monochromatic acoustic field:
   Evaluating a distribution of acoustic particle velocity to a single vector value by integrating the dot product of a real three-dimensional weighting vector field with a particle velocity field with a weighting function, where either of which functions may have complex-valued components and are derived from physical transducer properties.
   Setting to zero the contribution of transducers whose wavefronts at the point have an opposing direction to the normal specified at each evaluated sub-region of the integral.
   Applying zero or more null points to be added to the null space of the matrix.
   Using this as the objective function to be maximised in an optimisation, where the optimisation result takes the form of the eigenvectors of a matrix formed from cross-multiplied terms of the objective function for each transducer.
   Summing one or more such matrices to generate an eigensystem where one or more eigenvectors produces the specified field.
4. A method of, on a monochromatic acoustic field:
   Evaluating a distribution of acoustic pressure to a single value by integrating the product of the acoustic pressure field function with a weighting function, either of which function may be complex-valued and are derived from physical transducer properties.
   Applying zero or more null points to be added to the null space of the matrix.
   Using this as the objective function to be maximised in an optimisation, where the optimisation result takes the form of the eigenvectors of a matrix formed from cross-multiplied terms of the objective function for each transducer.
   Using the contribution of each transducer to describe the optimal phases and amplitudes for the transducer input signal.
5. A method of, on a monochromatic acoustic field:
   Evaluating a distribution of acoustic particle velocity to a single vector value by integrating the dot product of a real three-dimensional weighting vector field with a particle velocity field with a weighting function, where either of which functions may have complex-valued components and are derived from physical transducer properties.
   Applying zero or more null points to be added to the null space of the matrix.
   Using this as the objective function to be maximised in an optimisation, where the optimisation result takes the form of the eigenvectors of a matrix formed from cross-multiplied terms of the objective function for each transducer.
   Using the contribution of each transducer to describe the optimal phases and amplitudes for the transducer input signal.
6. A method of, on a monochromatic acoustic field:
   Evaluating a distribution of acoustic particle velocity to a single vector value by integrating the dot product of a real three-dimensional weighting vector field with a particle velocity field with a weighting function, where either of which functions may have complex-valued components and are derived from physical transducer properties.
   Setting to zero the contribution of transducers whose wavefronts at the point have an opposing direction to the normal specified at each evaluated sub-region of the integral.
   Applying zero or more null points to be added to the null space of the matrix.
   Using this as the objective function to be maximised in an optimisation, where the optimisation result takes the form of the eigenvectors of a matrix formed from cross-multiplied terms of the objective function for each transducer.
   Using the contribution of each transducer to describe the optimal phases and amplitudes for the transducer input signal.
7. The method of claims 1 to 6, where further a device implements the method and uses the result to drive acoustic transducers.
8. The method of claims 1 to 6, where further a device implements the method and uses the result as a portion of a linear basis set which is used to drive acoustic transducers.
9. The method of claims 1 to 6 where an acoustic beam is produced
10. The method of claims 1 to 6 where an acoustic volume is produced
11. The method of claims 1 to 6 where an acoustic surface is produced
12. A method of, on an acoustic field:
    Evaluating an acoustic particle velocity to a single value at a point using the linear combination of fields derived from physical transducer properties.
    Setting to zero the contribution of transducers whose wavefronts at the point have an opposing direction to the normal at the control point.
    Using this as a basis function in an optimisation problem for finding the phases and amplitudes for the transducer input signal.
13. A method of, on an acoustic field:
    Evaluating an acoustic particle velocity to a single value at a point using the linear combination of fields derived from physical transducer properties.
    Setting to zero the contribution of transducers whose wavefronts at the point have an opposing direction to the normal at the control point.
    Using this as the objective function to be maximised in an optimisation, where the optimisation result takes the form of the eigenvectors of a matrix formed from cross-multiplied terms of the objective function for each transducer, which is then finding the phases and amplitudes for the transducer input signal.

14. A method of, on an acoustic field:
   Evaluating an acoustic particle velocity to a single value at a point using the linear combination of fields derived from physical transducer properties.
   Setting to zero the contribution of transducers whose wavefronts at the point have an opposing direction to the normal at the control point.
   Using the contribution of each transducer to describe the optimal phases and amplitudes for the transducer input signal.

15. The method of claims 1 to 14, wherein the transducers produce a haptic effect when the resulting structure is applied as an input signal and modulated.

16. The method of claims 1 to 14, wherein the transducers produce a haptic effect when the resulting structure is applied as an input signal and is modified through time.

6. EVALUATION OF COMPLEX-VALUED TRANSCENDENTAL FUNCTIONS, MULTIPLICATION AND DIVISION IN HARDWARE

By aiming to convert between $r+i\theta \leftrightarrow 2^r(e^{\pi/2})^{i\theta}$ instead of $r+i\theta \leftrightarrow e^{r+i\theta}$, the BKM algorithm may be reengineered to yield a greatly simplified technique which is more useful in physical hardware implementations.

I. Introduction

There exist many techniques for the computation of trigonometric and other special functions in hardware. One such method is the BKM method, which exchanges complex logarithms for complex exponentiations and vice versa, generating these special functions as a side effect of moving from one representation to another. Of special interest are those dealing with complex-valued functions as situations in which such functions are found to be necessary are encountered often.

An efficient method to move between logarithm and exponential forms enables multiplication and division to be carried out in the logarithmic space as simple addition and subtraction. Due to the nature of the process this can also be exploited to produce transcendental functions related to the exponential easily. Since this can be generated from a single algorithm, this results in reduced implementation size, since only one element requires implementation, and reduced development time, as only one method need be implemented and optimized.

An existing algorithm, BKM, implements this approach, but includes three disadvantageous requirements which are almost or completely removed in the proposed method:

Hardware division among other difficult to implement functions to pre- and post-processing steps on the data input and output.

Irrational values and factors that create rounding issues for efficient implementations.

Extra operations that are required to integrate with floating point types.

The next section will describe how the proposed method has been designed to be free of these drawbacks.

II. Motivation and Comparative Range Reduction

The process is centered on Euler's formula, $e^{i\theta}=\cos\theta+i\sin\theta$, but where $e^r$ is a further coefficient as the formula has a complex generalization which yields, $e^{r+i\theta}=e^r(\cos\theta+i\sin\theta)$. The complex function which the BKM algorithm embodies is exactly this, making the implemented process $r+i\theta \leftrightarrow e^{r+i\theta}$. The algorithm heavily uses range reduction techniques to fit the complex value $r+i\theta$ into a range where convergence may be guaranteed. This is not a function that has a neat implementation, to the extent that it is likely easier to evaluate using the proposed method by pre- or post-processing with an irrational scaling factor to achieve $r+i\theta \leftrightarrow e^{r+i\theta}$. In many cases, this irrational scaling factor may be eliminated to provide a workflow whose inputs and outputs are intended to be multiples of physically or computationally meaningful rational numbers.

When processing a complex exponentiation, the exponentiation may be split into a real part and an imaginary part, which use the same input data but produce different results. This is in some ways similar to a Cartesian-to-polar transform.

Considering just the real part of the logarithm to be exponentiated, this contains all the modulus information, similar to the r component of the Cartesian-to-polar transform. This is traditionally the irrational constant e raised to the power of the real part. To feed it into the algorithm this first has to undergo range reduction, meaning that we must find the remainder, dividing modulo the irrational value ln 2 such that it fits inside the convergence domain. This involves a hardware division (the 1994 paper recommends the SRT division technique), and so this adds a highly expensive technique in terms of the logic required to implement a division alongside the algorithm.

The premise of the proposed algorithm is that powers of two should be used to make the range reduction straightforward. With this motivation, the real part should be interpreted as two raised to the given power which is the real part, so an exponentiation with base two. The whole number of the real logarithm input then may refer to bit shifts on the output and only the fractional part of the relative binary logarithm input needs to fit in the domain of convergence. The integer part of the real component of the complex logarithm is then taken by round-to-nearest and exponentiated separately in this way.

Considering just the imaginary part of the logarithm to be exponentiated, this contains all the argument or angle information, similar to the θ component of the Cartesian-to-polar transform. This is also traditionally raised to the power e, but e is not the problem here. The problem is π this time, as the imaginary logarithm part can be construed as an angle, but to restrict the domain of convergence we again have to find the remainder from an integer fraction of 2π so that rotational symmetry may be exploited. This involves yet more division processes that are expensive in terms of logic size.

If instead of the base e logarithm, base two could be used. This obtains the expansion $2^{i\theta}=\cos(\theta \ln 2)+i\sin(\theta \ln 2)$. This is yet more unwanted irrational values, however, if we specifically use the base $e^{2\pi}$ we can use θ to express the number of rotations. Unfortunately, using this base leads to a method that does not converge. The best trade-off between technique and convergence range yields base $e^{\pi/2}$. This means each integer value represents a quadrant. Each multiple of four is a whole rotation. Bitwise operations may then be used to extract the number of rotations. The number of quadrants may be applied to the output as a switching of real and imaginary numbers and signs. Again, this yields a technique wherein the integer part of the imaginary component of the complex logarithm is taken by round-to-nearest and processed separately in this way.

Figure 32:
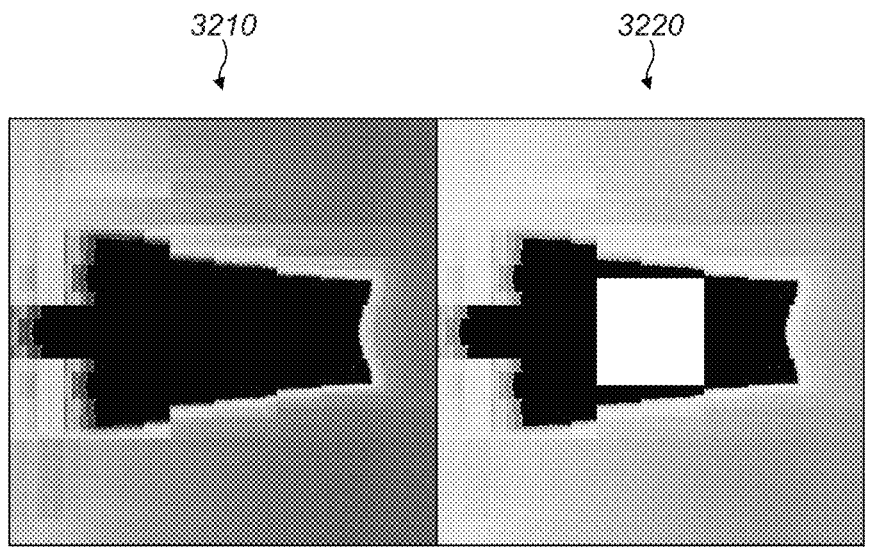
FIG. 32-34 show the regions of convergence of the logarithm and exponentiation methods without remapping.

This leaves the fractional part of the logarithm still to be exponentiated in the range $R=[-0.5, +0.5)+i[-0.5, +0.5)$ as shown in the right panel 3220 of FIG. 32, which fits into the range of convergence for the main algorithm. In FIG. 32, errors in the exponential plotted for the input to the logarithm-to-exponential process in the region [−2.0,+2.0), where the right-hand side is positive real and the lower part of the image positive imaginary. With 50 fractional bits and a similar number of iterations, the black area represents values that have converged to an accuracy greater than $2^{-45}$. The left panel 3210 shows the domain of convergence where gray is mapped to errors greater than $2^{-45}$. The right panel 3220 shows the final required convergence region R=[−0.5, +0.5)+i[−0.5, +0.5)) in white.

Discussion of the main algorithm for the fractional part of the logarithm input is described later.

Figure 33:
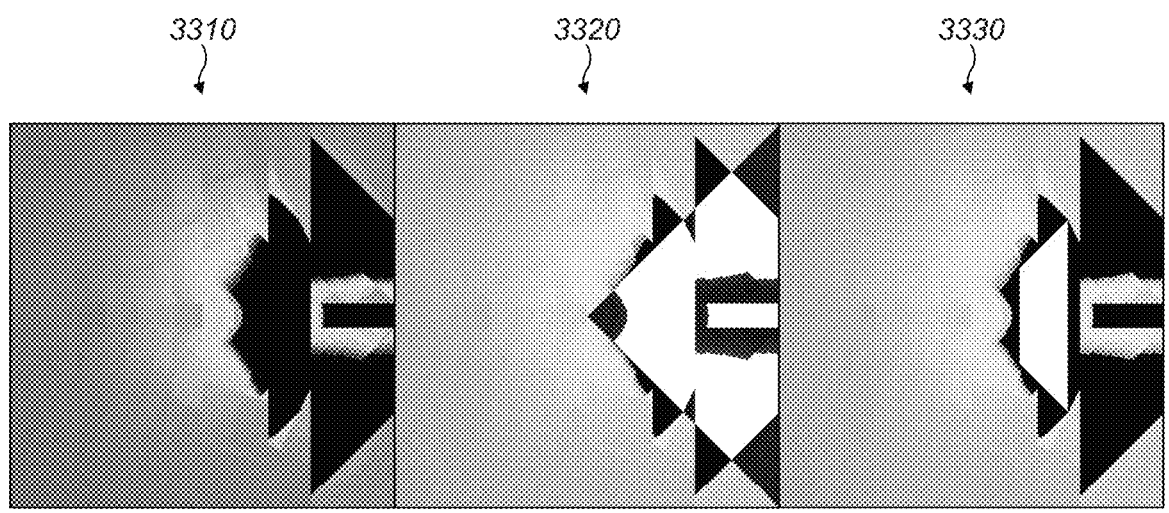

The reverse process is also achieved, taking the value with its exponentiated real and imaginary parts and reducing it to its original logarithms. To begin, we find the quadrant, offset by 45°, that the complex value belongs to. This is achieved by determining which component has the largest absolute value; whether it is real or imaginary and its sign. This locates which of these quadrants offset in angle the value belongs to. This is then used to compute a rotation to move the values into the first quadrant whose area is centered on the positive part of the real line, as shown in the center panel 3320 of FIG. 33. FIG. 33 shows errors in the exponential plotted for the input to the exponential-to-logarithm process in the region [−2.0, +2.0), where the right-hand side is positive real and the lower part of the image positive imaginary. With 50 fractional bits and a similar number of iterations, the black area represents values that have converged to an accuracy greater than $2^{-45}$. The left panel 3310 shows the domain of convergence where gray is mapped to errors greater than $2^{-45}$. The middle panel 3320 shows the quadrant centered on the real line using inverted grayscale. The right panel 3330 shows the final required convergence region R=[+0.5, +1.0)+i[−ℜ (R), +ℜ (R)) in white.

The imaginary part of the logarithm output is pre-loaded with the equivalent imaginary integer part of the output complex logarithm. Due to the 45° offset, a further test would be necessary for the complex branch cut to fall on the negative part of the real line, but if a two's complement system wrap around is used this may be ignored, as given the necessary bits the imaginary part of the logarithm measured in quadrants can be easily restricted to lie in the interval [−2.0, 2.0).

At this point as it is certain that the value lies in the first quadrant, the real part is known to be greater than or equal to the imaginary part in absolute value and the real part is known to be positive. To find the integer part of the real part of the logarithm, we can count the leading zeroes in the fixed-point representation. The value of the subtraction of this count from the number of bits in the fixed-point representation is effectively [$\log_2$ ℜ ($z_{input, \ rotated}$)]+k, where k depends on the representation of the bits and so is a representation of the integer part of the binary logarithm, which can be immediately added onto the real part of the logarithm register. The existing data, both real and imaginary, can then be shifted up by the number of bit places required to cause the real part to lie in the interval [+0.5, +1.0), as shown in the right panel of FIG. 33, which is determined by the initial count leading zeroes and the k that depends on the representation of the bits. It should be noted that while this may not be the nearest integer representation of the output real logarithm, it is integer and brings the remainder of the process into the region of convergence with the correct format.

At the end of this process, the integer part of the output complex logarithm has been determined, leaving the fractional part of the output undetermined and the input range R=[+0.5, +1.0)+i[−ℜ (R), +ℜ (R)), which fits into the range of convergence for the main algorithm. Discussion of the main algorithm for the substantially fractional part of the logarithm output will be described below.

Figure 34:
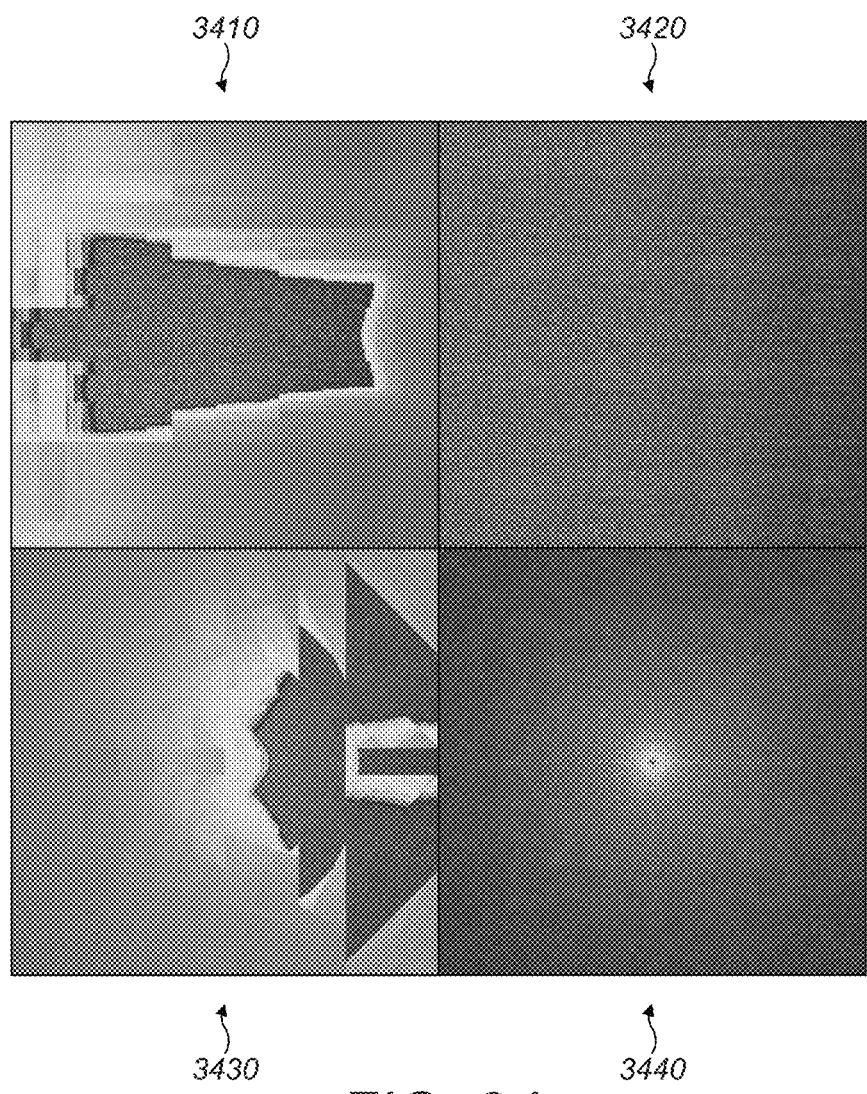

The result is that the function r+iθ↔$2^r(e^{\pi/2})^{i\theta}$ is the process now modelled as can be seen from FIG. 34. In FIG. 34, plotted errors in the exponential for the exponentiation 3410 and logarithm process 3430 domains for the sufficiently fractional parts only, alongside the range reduced counterparts that make up the final composite values for the exponentiation 3420 and logarithm 3440 processes. The noisy gray denotes areas where correct convergence causes small numerical error to dominate the error measurement, showing that the convergence has been achieved everywhere for exponentiation 3420 and logarithm 3440.

Changing the base of the result still means it has all the properties of logarithms and exponents, meaning that the real parts of logarithms can be added and subtracted to provide exponentiated multiplication and division. Equally, the angles behave the same, only that they are represented as integer multiples of a quadrants, so 4 to a rotation, a value easily manipulated in hardware logic. In their logarithm form, adding and subtracting the imaginary values is the same as rotating clockwise and anti-clockwise around zero in the complex-valued exponentiated space. For the complex values taking their combined real and imaginary parts irrespective of the fact that they are composed of different bases, adding and subtracting the real and imaginary parts, can used to implement complex multiplication and division.

These results may be trivially extended to floating-point representations as in these formats the required pre-processing is already mostly achieved by virtue of the mantissa and exponent form. If the values in base e are absolutely required and most of the time they are not, then the real part of the output logarithm may be multiplied by ln 2 and the imaginary part by π/2. Equally, to take in logarithm data in base e format, the values can be taken as reciprocals $$\left(\frac{1}{\ln 2}, \frac{2}{\pi}\right)$$

and multiplied component-wise to convert, before engaging in the initial range reduction to exponentiate with this method.

III. General Procedure

The new algorithm proceeds in a similar way to the BKM technique to find or use the fractional part of the logarithm. There is a set of values $d_n \in$ {0, 1, i, −1, −i, 1+i, 1−i, 1+i, −1−i} from which $d_n$ is chosen on each algorithm step n. Choices of which $d_n$ to use are made by comparing a truncated number with a set bit count which may be a subset of the bits from the input registers. Once a $d_n$ is selected, look-up tables of precalculated logarithms are required to balance the 1+$d_n 2^{-n}$ (bit shifting (potentially with rounding applied on the most significant unused bit) and addition/subtraction arithmetic) multiplications applied to the registers holding exponentiated values with the equivalent logarithms to be subtracted from the registers holding logarithm values. Depending whether the process is to find a logarithm or to compute exponentiation, there may be extra shifting, extra arithmetic or both in order to arrange the system into a convergent configuration. At the end of some N iterations, the desired value, either exponential or logarithm, is found to within an accuracy that depends on the number of iterations N and the number of bits used for the representation.

IV. Look-Up Tables of Logarithms

The proposed method differs from existing techniques in that these logarithms must now reflect the exponentiation as $2^r(e^{\pi/2})^{i\theta}$. Due to this, the real part of the logarithm table must now be preloaded with $\log_2\|1+d_n 2^{-n}\|$, and the imaginary part $2/\pi \arg(1+d_n 2^{-n})$ or $\Im(\log_{e^{\pi/2}}(1+d_n 2^{-n}))$, for $n=1, \ldots, N$, in the desired fixed point format.

Although we have chosen 2 and $e^{\pi/2}$ for the logarithm base, it is likely that a different choice of base may give an algorithm for the logarithm system that does not have a different first iteration. These values have been chosen because they represent a design that may achieve both processes using the same hardware. If a separate implementation using distinct hardware is to be used for the logarithm mode as from the exponentiation mode, then this may not be the best choice of base.

V. Method for the Fractional Part of the Logarithm

The core method for the new algorithm largely follows from those used by the BKM process, with some new key differences. The comparison thresholds have been derived anew to accommodate the new bases for the logarithms and exponentiation and the changed domain of convergence required for the new technique. There is also a slightly modified comparison threshold for the first iteration of the logarithm process to achieve convergence within the required domain.

VI. Exponentiation Mode

The exponentiation mode described in this section may also be modified to provide a complex multiplication with the exponential value. If this is to be achieved, this must be pre-loaded before the range reduction steps if the output is to be correct. It should also be noted that this would replace the output exponentiation value and so should be not used if this value is required. It is also feasible to store and wait to apply the solution from the integer parts of the logarithm (the value $z_{integer, output}$) to the end of the process. This may reduce the storage required for the intermediate registers in which the processing occurs, although this should be weighed against the extra requirements of storage needed for the integer parts of the solution.

Alternatively, multiplication with the final exponentiation value may be achieved in parallel by creating extra registers and ensuring that equivalent operations occur in these extra registers. In this way, the exponentiation process may complex multiply the output exponential value with almost arbitrarily many other complex values.

Assuming the fractional part of the input logarithms to be the input, the algorithm for the domain of convergence $z_{input} \in \mathbb{R}=[-0.5, +0.5)+i[-0.5, +0.5)$ is:

1. Assuming there are four basic registers, labelled $\Re(z_{log})$, $\Im(z_{log})$, $\Re(z_{exp})$ and $\Im(z_{exp})$. Alongside, there are two extra slave multiplication registers $\Re'(z_{exp})$ and $\Im'(z_{exp})$ to demonstrate how the method operates when used for auxiliary complex multiplication. The initial values of these registers are:

$$\Re(z_{log}):=2\Re(z_{input}),$$

$$\Im(z_{log}):=2\Im(z_{input}),$$

$$\Re(z_{exp}):=\Re(z_{integer\,input,output} \times z_{premultiply}),$$

$$\Im(z_{exp}):=\Im(z_{integer\,input,output} \times z_{premultiply}),$$

where $z_{premultiply}:=1.0$, if there are no requirements for pre-multiplication. The slave multiplication registers may also be similarly constructed with:

$$\Re'(z_{exp}):=\Re(z_{integer\,input,output} \times z_{premultiply}'),$$

$$\Im'(z_{exp}):=\Im(z_{integer\,input,output} \times z_{premultiply}')$$

2. Iterate through the values $1, \ldots, N$ as the index $n$:

3. Truncate $\Re(z_{log})$ to form $\Re(z_{log,\,test})$ such that it has three bits; one sign bit and two integer bits in two's complement such that the range is $[-4.0, +4.0)$ with the smallest change being 1.

4. Truncate $\Im(z_{log})$ to form $\Im(z_{log,\,test})$ such that it has three bits; one sign bit, one integer bit and one fraction bit in two's complement such that the range is $[-2.0, +2.0)$ with the smallest change being 0.5.

5. Test the 3-bit values to determine $d_n$:

$$\Re(d_n) := \begin{cases} -1, & \text{if } \Re(z_{log,\,test}) < -0b01 \text{ (or } < -1.0), \\ +1, & \text{if } \Re(z_{log,\,test}) > +0b00 \text{ (or } \geq +1.0), \\ 0, & \text{if neither,} \end{cases}$$

$$\Im(d_n) := \begin{cases} -i, & \text{if } \Im(z_{log,\,test}) < -0b01 \text{ (or } < 0.5), \\ +i, & \text{if } \Im(z_{log,\,test}) > +0b00 \text{ (or } \geq +0.5), \\ 0, & \text{if neither.} \end{cases}$$

6. Apply the multiplication to the exponential registers using shifting and arithmetic to compute:

$$\Re(z_{exp,n}) :=$$

$$\Re(z_{exp,n-1}) + \begin{cases} -2^{-n}\Re(z_{exp,n-1}) = -sra(\Re(z_{exp,n-1}), n), & \text{if } \Re(d_n) = -1, \\ +2^{-n}\Re(z_{exp,n-1}) = +sra(\Re(z_{exp,n-1}), n), & \text{if } \Re(d_n) = +1, + \\ 0, & \text{if neither} \end{cases}$$

$$\begin{cases} +2^{-n}\Im(z_{exp,n-1}) = +sra(\Im(z_{exp,n-1}), n), & \text{if } \Im(d_n) = -i, \\ -2^{-n}\Im(z_{exp,n-1}) = -sra(\Im(z_{exp,n-1}), n), & \text{if } \Im(d_n) = +i, \\ 0, & \text{if neither.} \end{cases}$$

And:

$$\Im(z_{exp,n}) := \Im(z_{exp,n-1}) +$$

$$+\begin{cases} -2^{-n}\Im(z_{exp,n-1}) = -sra(\Im(z_{exp,n-1}), n), & \text{if } \Re(d_n) = -1, \\ +2^{-n}\Im(z_{exp,n-1}) = +sra(\Im(z_{exp,n-1}), n), & \text{if } \Re(d_n) = +1, + \\ 0, & \text{if neither,} \end{cases}$$

$$\begin{cases} -2^{-n}\Re(z_{exp,n-1}) = -sra(\Re(z_{exp,n-1}), n), & \text{if } \Im(d_n) = -i, \\ +2^{-n}\Re(z_{exp,n-1}) = +sra(\Re(z_{exp,n-1}), n), & \text{if } \Im(d_n) = +i, \\ 0, & \text{if neither.} \end{cases}$$

Do the same to any auxiliary registers such as $\Re'(z_{exp})$ and $\Im'(z_{exp})$ to apply the multiplication process to these also.

7. Subtract the corresponding entry in the logarithm tables from the registers:

$$\Re(z_{log,n}) := \Re(z_{log,n-1}) - 2^n \log_2\|1 + d_n 2^{-n}\|,$$

$$= \Re(z_{log,n-1}) - sll(\text{table}_R[d_n, n], n),$$

$$\Im(z_{log,n}) := \Im(z_{log,n-1}) - 2^n(2/\pi \arg(1 + d_n 2^{-n})),$$

$$= \Im(z_{log,n-1}) - sll(\text{table}_J[d_n, n], n).$$

8. Shift the logarithm registers over to the left by one place, doubling the value of their contents.

$\Re_{(z_{log,n})}:=sll(\Re_{(z_{log,n})},1)$, $\Im_{(z_{log,n})}:=sll(\Im_{(z_{log,n})},1)$.

9. Return to step 2 for the next iteration, until N is reached, at which point the registers will contain their final values:

$R(z_{exp,N}) := R\left(z_{integer\ input,output} \times z_{premultiply} \times 2^{R(z_{input})}\left(e^{\pi/2}\right)^{i\mathcal{J}(z_{input})}\right)$, $\mathcal{J}(z_{exp,N}) := \mathcal{J}\left(z_{integer\ input,output} \times z_{premultiply} \times 2^{R(z_{input})}\left(e^{\pi/2}\right)^{i\mathcal{J}(z_{input})}\right)$, And:

$R'(z_{exp,N}) := R\left(z_{integer\ input,output} \times z_{premultiply'} \times 2^{R(z_{input})}\left(e^{\pi/2}\right)^{i\mathcal{J}(z_{input})}\right)$, $\mathcal{J}'(z_{exp,N}) := \mathcal{J}\left(z_{integer\ input,output} \times z_{premultiply'} \times 2^{R(z_{input})}\left(e^{\pi/2}\right)^{i\mathcal{J}(z_{input})}\right)$.

Having appreciated the form of the process, it is easy to find other testing procedures that are convergent, even sometimes in the required domain, by forming $\Re(z_{log,\ test})$, $\Im(z_{log,\ test})$ or both using different number of bits or different comparison values, although we have endeavored to reduce complexity by specifying the required value tests in the simplest known form.

VII. Logarithm Mode

The logarithm mode described in this section may also be modified to provide a complex division with the input value. If this is to be achieved, it can only occur in parallel by creating extra registers and ensuring that equivalent operations occur in these extra registers. This contrasts with the auxiliary multiplication, where the original register could be overloaded, which cannot be achieved here because the modification of the exponentiation register in this mode would prevent convergence of the algorithm. However, using auxiliary registers can circumvent this, allowing the logarithm process to, if desired, produce complex-valued division of almost arbitrarily many other complex values with the value input to this process as denominator.

1. Assuming the fractional part of the output logarithms to be the output, the algorithm for the domain of convergence $z_{input} \in R=[+0.5, +1.0)+i[-\Re(R), +\Re(R))$ is:

2. Assuming there are four basic registers, labelled $\Re(z_{log})$, $\Im(z_{log})$, $\Re(z_{exp})$ and $\Im(z_{exp})$. Alongside, there are two extra slave division registers $\Re'(z_{exp})$ and $\Im'(z_{exp})$ to demonstrate how the method operates when used for auxiliary complex division. The initial values of these registers are:

$\Re_{(z_{log})}:=\Re_{(z_{integer\ output,output})}$, $\Im_{(z_{log})}:=\Im_{(z_{integer\ output,output})}$, $\Re_{(z_{exp})}:=2(\Re_{(z_{input})}-1.0)$, $\Im_{(z_{exp})}:=2\Im_{(z_{input})}$, The slave division registers may also be similarly constructed with:

$\Re'_{(z_{exp})}:=\Re_{(z_{numerator}\div z_{integer\ output,input})}$, $\Im'_{(z_{exp})}:=\Im_{(z_{numerator}\div z_{integer\ output,input})}$ Noting that neither the doubling or the 1.0 is applied to the registers $\Re'(z_{exp})$ and $\Im'(z_{exp})$.

2. Iterate through the values 1, . . . , N as the index n:

3. Truncate $\Re(z_{exp})$ to form $\Re(z_{exp,\ test})$ such that it has five bits; one sign bit, one integer bit and three fraction bits in two's complement such that the range is [−2.0, +2.0) with the smallest change being 0.125.

4. Truncate $\Im(z_{exp})$ to form $\Im(z_{exp,\ test})$ such that it has five bits; one sign bit, two integer bits and two fraction bits in two's complement such that the range is [−4.0, +4.0) with the smallest change being 0.25.

5. Test the two 5-bit values (with modified comparisons for the first iteration) to determine $d_n$:

$R(d_n) := \begin{cases} +1, & \text{if } R(z_{exp,test}) < -0b0110 \text{ (or } < -0.75\text{)}, \\ \text{or} & \text{if } n = 1 \wedge R(z_{exp,test}) \leq -0b0110 \text{ (or } < -0.625\text{)}, \\ -1, & \text{if } R(z_{exp,test}) > +0b0001 \text{ (or } \geq +0.25\text{)}, \\ 0, & \text{if neither}, \end{cases}$ $\mathcal{J}(d_n) := \begin{cases} +i, & \text{if } \mathcal{J}(z_{exp,test}) < -0b0110 \text{ (or } < -0.25\text{)}, \\ \text{or} & \text{if } n = 1 \wedge \mathcal{J}(z_{exp,test}) \leq -0b0110 \text{ (or } < -0.125\text{)} \\ -i, & \text{if } \mathcal{J}(z_{exp,test}) > +0b0001 \text{ (or } \geq +0.25\text{)}, \\ \text{or} & \text{if } n = 1 \wedge \mathcal{J}(z_{exp,test}) > +0b0001 \text{ (or } \geq +0.125\text{)} \\ 0, & \text{if neither}. \end{cases}$ 6. Apply the multiplication to the exponential registers using shifting and arithmetic to compute:

$R(z_{exp,n}) := R(z_{exp,n-1}) +$ $+ \begin{cases} -2^{-n}R(z_{exp,n-1}) = -sra(R(z_{exp,n-1}), n), & \text{if } R(d_n) = -1, \\ +2^{-n}R(z_{exp,n-1}) = +sra(R(z_{exp,n-1}), n), & \text{if } R(d_n) = +1, \\ 0, & \text{if neither}, \end{cases}$ $+ \begin{cases} +2^{-n}\mathcal{J}(z_{exp,n-1}) = +sra(\mathcal{J}(z_{exp,n-1}), n), & \text{if } \mathcal{J}(d_n) = -i, \\ -2^{-n}\mathcal{J}(z_{exp,n-1}) = -sra(\mathcal{J}(z_{exp,n-1}), n), & \text{if } \mathcal{J}(d_n) = +i, \\ 0, & \text{if neither}. \end{cases}$ And:

$\mathcal{J}(z_{exp,n}) := \mathcal{J}(z_{exp,n-1}) +$ $+ \begin{cases} -2^{-n}\mathcal{J}(z_{exp,n-1}) = -sra(\mathcal{J}(z_{exp,n-1}), n), & \text{if } R(d_n) = -1, \\ +2^{-n}\mathcal{J}(z_{exp,n-1}) = +sra(\mathcal{J}(z_{exp,n-1}), n), & \text{if } R(d_n) = +1, \\ 0, & \text{if neither}, \end{cases}$ $+ \begin{cases} -2^{-n}R(z_{exp,n-1}) = -sra(R(z_{exp,n-1}), n), & \text{if } \mathcal{J}(d_n) = -i, \\ +2^{-n}R(z_{exp,n-1}) = +sra(R(z_{exp,n-1}), n), & \text{if } \mathcal{J}(d_n) = +i, \\ 0, & \text{if neither}. \end{cases}$ Do the same to any auxiliary registers such as $\Re'(z_{exp})$ and $\Im'(z_{exp})$ to apply the division process to these.

7. Add $d_n$ to $\Re(z_{exp,\ n})$ and $\Im(z_{exp,\ n})$:

$\Re_{(z_{exp,n})}:=\Re_{(z_{exp,n})}+\Re_{(d_n)}$, $\Im_{(z_{exp,n})}:=\Im_{(z_{exp,n})}+\Im_{(d_n)}$.

Do not add this to $\Re'(z_{exp})$ and $\Im'(z_{exp})$.

8. Shift the exponential registers over to the left by one place, doubling the value of their contents.

$\Re_{(z_{exp,n})}:=sll(\Re_{(z_{exp,n})},1)$, $\Im_{(z_{exp,n})}:=sll(\Im_{(z_{exp,n})},1)$.

Do not double the values of $\Re'(z_{exp})$ and $\Im'(z_{exp})$.

9. Subtract the corresponding entry in the logarithm tables from the registers:

$\Re_{(z_{log,n})}:=\Re_{(z_{log,n-1})}-2^n \log_2\|1+d_n 2^{-n}\|,=\Re_{(z_{log,n-1})}-sll(\text{table}\Re [d_n,n],n),$ $\Im_{(z_{log,n})}:=\Im_{(z_{log,n-1})}-2^n(2/\pi \arg(1+d_n 2^{-n})),=\Im_{(z_{log,n-1})}-sll(\text{table}\Im [d_n,n],n).$ 10. Return to step 2 for the next iteration, until N is reached, at which point the registers will contain their final values:

$\Re_{(z_{log,N})}:=\log_2\|\Re_{(z_{input})}+i\Im_{(z_{input})}\|,$ $\Im_{(z_{log,N})}:=2/\pi \arg(\Re_{(z_{input})}+i\Im_{(z_{input})}),$ And:

$\Re'_{(z_{exp,N})}:=\Re_{(z_{numerator}\div(z_{integer\ output,input}\times z_{input}))},$ $\Im'_{(z_{exp,N})}:=\Im_{(z_{numerator}\div(z_{integer\ output,input}\times z_{input}))}.$ Having appreciated the form of the process, it is possible to find other testing procedures that are convergent, even sometimes in the required domain, by forming $\Re(z_{exp,\ test})$, $\Im(z_{exp,\ test})$ or both using different number of bits or different comparison values, although we have endeavored to reduce complexity by specifying the required value tests in the simplest known form.

VIII. Redundant Number Systems

The algorithm, like the BKM method, is ideal for supporting techniques that slow the local flow of data, allowing for integration into high speed logic implemented in hardware. Using a redundant number system scheme such as carry-save for the arithmetic steps, coupled with the reduced number of bits presented for comparison on each iteration allows for an algorithm such as is presented here to have a high-speed, low-area implementation that is ideal for inclusion into integrated circuit designs. Benefits of such an implementation would include being able to reach higher clock speeds, while scaling well to operands with larger numbers of bits, making this design ideal for fabricating low-cost, modern solutions to problems involving manipulation of complex values.

For ease of intuition, rounding has been neglected in the foregoing description of the algorithm and should not be interpreted as an implication that correct rounding has not been considered in this invention. It should be clear that capitalizing on the most significant bit not directly used in any arithmetic operation to achieve a result with reduced error through the application of rounding, when applied at each step may increase the accuracy of the results described herein.

IX. Higher-Radix Approaches

In a similar way to other algorithms that evaluate in a per-bit fashion, the steps may be merged to create a method that computes multiple bits at once. This is termed a higher radix algorithm, as the output is treated as having a different base than 2, meaning that one digit from the new higher base is calculated per step. The drawback of this is that the choices for the look-up tables and shifts would also have to be merged, creating a larger set of choices for the algorithm to work through per iteration.

X. Real Algorithm

Many systems may benefit from using just the real part of the algorithm described herein. For instance, the sigmoidal logistic function, often used by neural network algorithms, may be generated by first determining the real 2' or if pre-multiplied ex using the exponentiation process. Then, adding one and dividing a preset constant by this value is possible, or continuing to use the E-mode followed by L-mode described by the original paper may produce the logistic function as:

$$L(x) = \frac{k}{1+e^{-(ax+b)}},$$

but the numerator k and further modifiers a and b remain configurable.

XI. Showing Convergence

Figure 35:
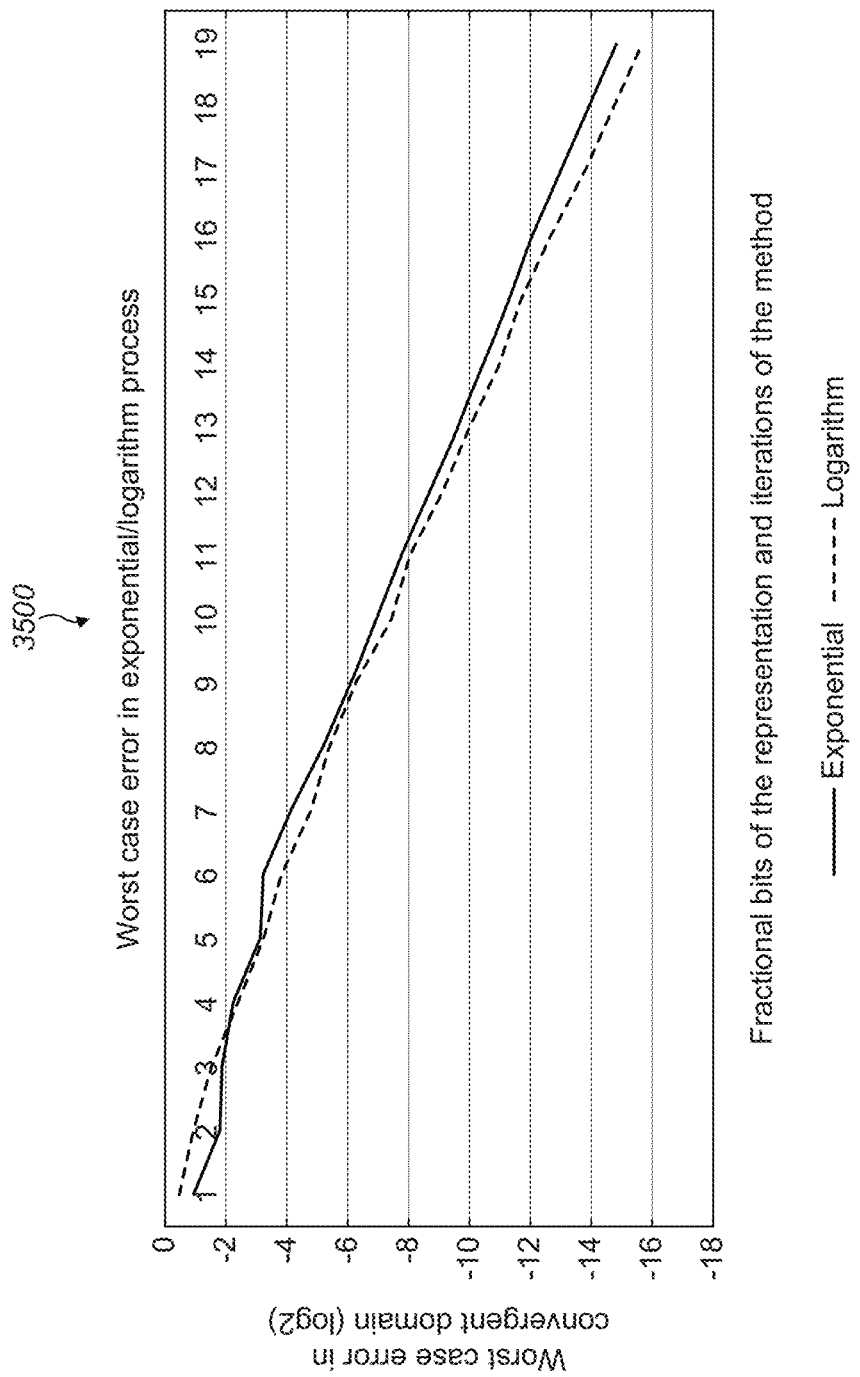
FIG. 35 show a convergence graph of the logarithm and exponentiation methods.

In FIG. 35, convergence of the exponential and logarithm methods is shown by the graph 3500. FIG. 35 shows testing each possible value in the necessarily convergent domain yields the worst case $\log_2$ error graphed here. The graph summarises the worst case behaviour from over one trillion complex test values (each real and imaginary value in the fractional domain that is remapped into has been tested for the number of iterations shown). To make the graphs comparable, the logarithmic result was translated into its exponentiated form before being tested for error. This ensures that the method is convergent for this many significant bits. This error may be reduced further by adding full rounding into the multiplication. The graph shows that as the precision and iterations increase, the error decreases similarly, showing convergence.

This graph 3500 show the absolute error of the worst case from all possible cases in the domain of convergence shrinking at a similar rate to the number of bits in the tables and iterations in the process. This reveals that the algorithm successfully converges linearly in bits of precision to the correct solution for all possible correct inputs for this number of bits of fixed point data.

XII. Potential Claims

1. A method for the simultaneous conversion of an input 'logarithm' complex number into a resulting ' exponential' complex number where:
a. the modulus of the resulting complex number consists of two raised to a real power of the real input complex number part and;
b. the argument of the resulting complex number consists of two raised to an integer power rotations multiplied by the real value of the imaginary input complex number part.

2. A method for the simultaneous conversion of an input ' exponential' complex number into a resulting 'logarithm' complex number where:
a. the real binary logarithm of the real modulus of the input complex number forms the real part of the resulting complex number and;
b. the real number of two raised to an integer power rotations expressed in the argument of the input complex number forms the imaginary part of the resulting complex number.

3. The method of claim 1 or 2 wherein the conversion is achieved substantially through bit shifting, comparisons and arithmetic on a binary representation of the complex number.

4. The method of claim 1 wherein a reduction in input and output range is performed by processing values corresponding substantially to a rounding of the components of the input complex number separately to a further part.

5. The method of claim 2 wherein a reduction in input and output range is performed by processing values corresponding substantially to a rounding of the components of the output complex number separately to a further part.

6. The method of claim 1 wherein the output complex value may be initialised with a value not equal to one so that the application of the iterations will modify a non-unity value to compute a complex multiplication by the value originally intended to be output.

7. The method of claim 1 wherein further complex values are instantiated such that operations applied to the output complex value may also be applied to these further values, yielding a multiplication of these further complex values by the complex value originally intended to be output.

8. The method of claim 2 wherein further complex values are instantiated such that operations applied to the input complex value may also be applied to these further values, yielding a division of these further complex values by the complex value input.

9. The method of claim 1 wherein a redundant number system is used to implement the process of repeated arithmetic applied to the extant complex values.

10. The method of claim 2 wherein a redundant number system is used to implement the process of repeated arithmetic applied to the extant complex values.

11. A device designed to perform any method of claims 1 through 10.

12. A data processor configured to perform any method of claims 1 through 10.

7. ACOUSTIC FIELDS BUILT FROM THE KRYLOV SUBSPACE OF A QUADRATIC PROBLEM

This disclosure describes a method to manipulate a quadratic problem when expressed as an eigensystem to produce a reduced rank basis set for inclusion into a linear system. By using a reduced rank basis an optimally information preserving set of (potentially reduced) basis functions may be automatically derived for inclusion into a complex-valued linear system to find the optimal complex-valued re-weightings of such basis functions to achieve a set of aims as described by a number of test functions.

The derivation of the reduced set of basis functions and how their inclusion into the appropriate stages of the implementation of an acoustic field linear optimization problem will be described.

I. Linear Control Regions

A linear control region, which is defined as an operator that performs an integral with an linear acoustic quantity, such as pressure, with a complex valued weighting function, $w(\chi)$, $\chi=\{x, y, z\}$:

$$f_p = \int\int\int_\Omega \overline{w(\chi)} \cdot p(\chi)\, dx\, dy\, dz,$$

may be used to evaluate an acoustic field. It should be noted that the complex conjugate is used to maximize function evaluation when $w(\chi)$ is paired with similar phase distributions in the acoustic quantity. Any approximation to this integral (such as sampling) can be used or indeed this may be used to approximate any linear operator over the field of acoustic pressure. A further integral may be constructed to optimize a control region using a vector particle velocity (wherein each vector component is complex-valued due to the harmonic motion of the field), given it is also linear, wherein:

$$f_v = \int\int\int_\Omega \overline{w(\chi)} \cdot u(\chi)\, dx\, dy\, dz,$$

with u the particle velocity of the medium, and w a three-dimensional vector field in which each dimension is complex-valued, which serves as a weighting function with the same purpose as above. In this way, different patterns of acoustic quantities may be evaluated in a linear fashion, wherein a particular phase of the result will maximize the objective function when phases align with the 'template' created by the scalar or vector function in w.

It also should be noted that $w(\chi)$ may be largely zero (or comprised of zero vectors) to create a single evaluation of multiple seemingly disjoint regions. Any integral approximation (such as sampling) can be used as this formulation can extend to any linear operator over the field of a linear acoustic quantity.

II. Quadratic Problems and Eigenproblems

A phased array may be described by a series of complex valued coefficients that controls each transducer. Driving an array of acoustic transducers at a fixed frequency with such an input x vector to maximise an acoustic quantity encoded in a matrix M may be expressed as a linear algebra problem, so that the intention is to:

maximize $x^H M x$
subject to $x^H x = 1$,
and $x \in \mathbb{C}^n$.

This may be solved by taking the dominant eigenvector of the matrix M, as the statement of the problem is also the definition of an eigenvector, here x. Building the matrix M may be achieved by first considering the linear acoustic quantities emitted by each transducer as a basis function in the global space of the acoustic quantity in question. This is a way to achieve the maximization of pressure and other acoustic quantities at a single point, described by an absolute position, $\chi$. However, using the described control region integral, the $q(\chi)$ that governs the acoustic quantities emitted into the field of each individual transducing element may be exchanged for $f(\chi)$, yielding the column vector:

$$f = \begin{bmatrix} f_1(\chi) \\ \vdots \\ f_n(\chi) \end{bmatrix},$$

By invoking linearity, the complex activation values driving each of the transducers may be multiplied leading to the vector:

$$m = \begin{bmatrix} x_1 \cdot f_1(\chi) \\ \vdots \\ x_n \cdot f_n(\chi) \end{bmatrix},$$

where n is the number of transducers. Given that this m is the result of a linear operator operating on a linear field, it may be Hermitian transposed and multiplied by itself to generate a quadratic form. Finally, $$m^H m = x^H M x = x^H f f^H x.$$

By modifying the weighting function w(χ) and solving for the eigenvectors of the matrix M, a variety of different beams, surfaces and other acoustic phenomenon may be created and maximized, producing optimally actuated regions in the acoustic field.

The null space generation technique discussed previously ("Eigensystem solutions for quadratic problems in mid-air haptic systems") may also be used to extend this method to describe acoustic levitation, as well as allowing for null steering and the formation of mid-air texture by introducing null points into the field at positions to describe structure. It should be noted that this process increases the rank of the matrix, so simplification is not possible should this be used.

Equally, multiple optimizations may be carried out by adding together M matrices for a number of control regions. This may also include matrices that represent control points. This generates a matrix that has increased rank, so some simplification methods are not possible in the case that this is used.

III. Reduced Rank Approximation to a High Rank Matrix

The key point is that a high-rank matrix may be intentionally created so that a reduced-rank approximation may be generated. For example, a system that has many hundreds of individual points may be automatically regrouped such that very few are described by independent basis functions, creating the realization of a basis set that appears to be higher dimensional than it is to increase fidelity, reduce complexity and allow basis functions to be created according to need automatically.

Existing approaches generate a new basis function for each control point, or control region. By creating an eigensystem for the optimization of each control point or region and summing them, or adding in nulls, the eigensystem gains rank. It is possible through the repeated process off adding basis function matrices and/or nulls, that a high degree of rank is obtained by the final matrix. The linear system, due to constraints on resources, may only be able to process at most n basis functions using at most m test functions. The high degree of rank of this optimization matrix may be in this case n' where n" optimisation matrices for generating individual basis functions have been merged together through addition. Using this approach, an otherwise impossible situation wherein n'>n and/or n">n, may be reduced to a problem that is expressed in a reduced basis set with n basis functions that is solvable with this system that has finite processing capabilities.

This reduced basis set is found by computing the Krylov subspace which substantially occupies the same matrix sub-space as the n most dominant eigenvectors of the final matrix that is composed of multiple optimisations for basis functions. The Krylov subspace may be found using a standard technique such as the Arnoldi iteration, wherein a dominant eigenvector is found and then removed from the remaining matrix and then this is applied in a repeated manner until n such eigenvectors are found.

IV. Mixed Approach

This approach whereby basis functions are extracted from high-rank matrices may be mixed and matched with the existing specific basis function approach. For instance, two control regions or points may be designated must-have and added into the basis set input to the linear system. Then, the remaining basis functions, given that they may be specified by quadratic optimizations and thus optimization matrices of their own, can be added to a single matrix which is then deconstructed using this Krylov sub-space method to find the most dominant n−2 eigenvectors to make up the remaining number of the set of basis functions input to the linear system. In this way, the two basis functions that are specified up front are guaranteed as they are imported directly into the linear system, but the remaining functions of the set are approximated. This system may be taken even further, wherein a set number of basis functions may be specified and taken from disjoint sets of basis functions which are each described by an optimization matrix of high rank and then a set number of basis sets taken. A further technique that could be used to derive reduced basis functions is to continue to take basis functions from a matrix until a power threshold is crossed. This threshold may be different for each matrix made up from conjoined basis sets and therefore yield eigenvectors of different power, where the power of each eigenvector is described by the magnitude its corresponding eigenvalue, and in this way allow eigenvectors may be produced by selecting eigenvector that are calculated from each matrix based on the product of a real priority value and the corresponding eigenvalue magnitude.

8. LINEAR SYSTEMS SOLUTION USING TEST FUNCTIONS

A method to 'test' whether the basis function set achieves certain goals that is defined separately from the basis function set would be of value. The quantitative evaluation of whether these goals are achieved is supplied to the optimization and this is used to generate desired properties in the acoustic field that are defined by these test functions.

The test functions and their role in the complex-valued linear system optimization will be described.

I. Linear Control Regions

A linear control region, which is defined as an operator that performs an integral with an linear acoustic quantity, such as pressure, with a complex valued weighting function, w(χ), χ={x, y, z}:

$$f_p = \iiint_\Omega \overline{w(\chi)} \cdot p(\chi)\, dx\, dy\, dz,$$

may be used to evaluate an acoustic field. It should be noted that the complex conjugate is used to maximize function evaluation when w(χ) is paired with similar phase distributions in the acoustic quantity. Any approximation to this integral (such as sampling) can be used or indeed this may be used to approximate any linear operator over the field of acoustic pressure. A further integral may be constructed to optimize a control region using a vector particle velocity (wherein each vector component is complex-valued due to the harmonic motion of the field), given it is also linear, wherein:

$$f_v = \iiint_\Omega \overline{w(\chi)} \cdot u(\chi)\, dx\, dy\, dz,$$

with u the particle velocity of the medium, and w a three-dimensional vector field in which each dimension is complex-valued, which serves as a weighting function with the same purpose as above. In this way, different patterns of acoustic quantities may be evaluated in a linear fashion, wherein a particular phase of the result will maximize the objective function when phases align with the 'template' created by the scalar or vector function in w.

It also should be noted that w(χ) may be largely zero (or comprised of zero vectors) to create a single evaluation of multiple seemingly disjoint regions. Any integral approximation (such as sampling) can be used as this formulation can extend to any linear operator over the field of a linear acoustic quantity.

II. Basis Function Set

Given a set of n basis functions as input, m test functions may be used through a linear system to find the optimal linear combination of the n basis functions to achieve the desired objective evaluation of the m test functions. These m test functions may be take the form of linear control region evaluations. Using the forms of the objective $f$ as given above these would be:

$$\omega(x) = \sum_{q=1}^{N} x_q \overline{f}_q,$$

or they could be evaluated through the single control point definition as:

$$\omega(x) = p(\chi) = \sum_{q=1}^{N} x_q \overline{p_q(\chi)},$$

where the overline denotes complex conjugate, χ is three-dimensional position, q parameterises all transducer elements and x is the transducer activation which is multiplied by the conjugate of the pressure field of the transducer. The equivalent form for a control point defined by particle velocity may also be used as an evaluator, albeit with a defined normal direction:

$$\omega(x) = u(x; \chi) \cdot \hat{n}(\chi) = \sum_{q=1}^{N} x_q \overline{u_q(\chi) \cdot \hat{n}(\chi)},$$

where any transducer q which is pointing in the wrong direction may be also omitted (have its contribution set to zero when $\hat{\delta}(\chi) \cdot \hat{n}(\chi) < 0$).

In both single control point definitions, the existing approach can be viewed as a special single point integral evaluation with unit weighting function case of the control region evaluation. The objective function here is then simply the acoustic quantity with no extra side effects.

III. Finding the Dominant Eigenvector

By evaluating each of the m basis functions using each of the n test functions, a rectangular matrix that is complex-valued is arrived at. As before, the dominant eigenvector denotes the combination of the m basis functions that best spans the space defined by the n test functions. However, as this is not necessarily a square matrix, the singular value decomposition is more appropriate, but then the only required eigenvector is the one that is dominant. A square Hermitian matrix may be constructed whose dominant eigenvector represents the elements of dominant combination of the system basis functions. The eigensystem is then described by:

$$\begin{bmatrix} 0 & \begin{bmatrix} \omega_1(x_1) & \cdots & \omega_1(x_n) \\ \vdots & \ddots & \vdots \\ \omega_m(x_1) & \cdots & \omega_m(x_n) \end{bmatrix} \\ \begin{bmatrix} \overline{\omega_1(x_1)} & \cdots & \overline{\omega_m(x_1)} \\ \vdots & \ddots & \vdots \\ \overline{\omega_1(x_n)} & \cdots & \overline{\omega_m(x_n)} \end{bmatrix} & 0 \end{bmatrix} \begin{bmatrix} a_1 \\ \vdots \\ a_m \\ b_1 \\ \vdots \\ b_n \end{bmatrix} = \lambda \begin{bmatrix} a_1 \\ \vdots \\ a_m \\ b_1 \\ \vdots \\ b_n \end{bmatrix}$$

where $b_1, \ldots, b_n$, describe coefficients whose phase generates a covering of the parameter space of the m test functions. The dominant eigenvector therefore has components $b_1, \ldots, b_n$, which describe the best covering of the space achievable with a single combination vector, and whose phase therefore optimizes this covering.

It should be noted that even in the case that the number of tests functions is equivalent to the number of basis functions, so m=n, the existing eigensystem approach may not necessarily be applicable. This is due to the fact that the matrix may no longer be Hermitian and therefore the direct application of the Rayleigh-Ritz method to this matrix without completing the above step may cause the method to fail to converge to the dominant eigenvector.

The dominant eigenvector should be used for phase information in the event that the phase data is not specified or is incomplete. The eigenvector may, on the end of each iteration be, modified to strip the amplitude data, averaged to zero in phase, limited in phase progression from the previous solution in a separate time-step or have one set of phase solutions for some basis functions held with existing and constant phase relationships while the complement of this set is optimized with phases between themselves and the stationary set of existing phases. In this way, this rectangular matrix system may be used to achieve an effect similar to the existing eigensystem approach which is specialized for the situation in which the functions that generate the basis set are the same as the functions used to evaluate the objective of the basis set.

IV. Linear System Solution

The complex-valued linear system now has a modified role, that of finding the set of basis functions that best replicate given values of the test functions. Here the linear system that must be used takes the form of a rectangular matrix:

$$\begin{bmatrix} \omega_1(x_1) & \cdots & \omega_1(x_n) \\ \vdots & \ddots & \vdots \\ \omega_m(x_1) & \cdots & \omega_m(x_n) \end{bmatrix} \begin{bmatrix} z_1 \\ \vdots \\ z_n \end{bmatrix} = \begin{bmatrix} x_1 \\ \vdots \\ x_m \end{bmatrix}.$$

As the matrix is rectangular, it may be that the number of the test functions is greater than the number of basis functions, resulting in a complex-valued least-squares system, or the number of test functions is less than the number of basis functions, resulting in a complex-valued least norm system. In either case, a standard decomposition may be used to find the solution vector, whose interpretation is that each component of the solution vector is the coefficient to be applied to each of the basis functions which cause the acoustic field when tested to express the given values of the test functions.

These test functions may express acoustic pressure or directional particle speed at a point, or a mixture of pressures and direction particle speeds across a region in space. Any combination of these functions may then make up the m test functions, which are solved for in the final step of the linear system.

Once the coefficients for the basis functions are known, the final values to actuating the transducers may be expanded as:

$$x = Az^H = \sum_{j=1}^{n} x_j \bar{z}_j$$

The input signals, give an assumption of a single monochromatic carrier frequency (which may be more or less valid due to changing circumstance) may be constructed by the application of components of this x to each transducer.

9. CONCLUSION

The various features of the foregoing embodiments may be selected and combined to produce numerous variations of improved haptic systems.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover, in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art. The term "coupled" as used herein is defined as connected, although not necessarily directly and not necessarily mechanically. A device or structure that is "configured" in a certain way is configured in at least that way, but may also be configured in ways that are not listed.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

I claim:

1. A method of adjusting the output of an ultrasonic phased array comprising:
   determining a position of interest and a desired output at the position of interest;
   calculating a maximum output from the ultrasonic phased array at the position of interest; and
   scaling the desired output using a scaling factor so that the desired output does not exceed the maximum output.

2. The method as in claim 1, wherein the desired output changes over time.

3. The method as in claim 1, wherein the maximum output is determined by a solver function.

4. The method as in claim 1, wherein the maximum output is pre-computed and stored in memory as a function of position relative to the ultrasonic phased array.

5. The method as in claim 2, wherein the position of interest changes over time and the maximum output changes in response to the change of the position of interest.

6. The method as in claim 5, wherein the scaling factor can be adjusted over time.

7. The method as in claim 6, wherein the scaling factor is filtered.

8. The method as in claim 7, wherein the filtering uses a recursive filter.

9. A method of adjusting output of an ultrasonic phased array comprising:
   determining at least two positions of interest and a desired output at each of the at least two positions of interest;
   calculating a maximum output from the ultrasonic phased array at each of the at least two positions of interest; and
   scaling at least one of the desired outputs using a scaling factor so that the at least one of desired outputs does not exceed the maximum output at the least one of the desired outputs.

10. The method as in claim 9, wherein the desired output changes over time.

11. The method as in claim 9, wherein the maximum output is determined by a solver function.

12. The method as in claim 9, wherein the maximum output is pre-computed and stored in memory as a function of position relative to the ultrasonic phased array.

13. The method as in claim 10, wherein the position of interest changes over time and the maximum output changes in response to the change of the position of interest.

14. The method as in claim 13, wherein the scaling factor can be adjusted over time.

15. The method as in claim 14, wherein the scaling factor is filtered.

16. The method as in claim 15, wherein the filtering uses a recursive filter.

* * * * *